(12) United States Patent
Townley et al.

(10) Patent No.: US 6,302,916 B1
(45) Date of Patent: Oct. 16, 2001

(54) POLYURETHANE AND SO FORTH CONTAINING JOINTS

(75) Inventors: Charles O. Townley, Port Huron; Kurt C. Frisch, Grosse Ile; Aisa Sendijarevic, Troy, all of MI (US)

(73) Assignee: BioPro, Inc., Port Huron, MI (US)

( * ) Notice: Subject to any disclaimer, the term of this patent is extended or adjusted under 35 U.S.C. 154(b) by 0 days.

(21) Appl. No.: 09/472,391

(22) Filed: Dec. 23, 1999

Related U.S. Application Data

(60) Provisional application No. 60/113,575, filed on Dec. 24, 1998, and provisional application No. 60/123,613, filed on Mar. 10, 1999.

(51) Int. Cl.[7] .................................. A61F 2/30; A61F 2/02
(52) U.S. Cl. ..................................... 623/23.58; 623/23.61
(58) Field of Search .......................... 623/23.58, 23.61, 623/23.59, 23.62

(56) References Cited

U.S. PATENT DOCUMENTS

| | | | | |
|---|---|---|---|---|
| 4,645,503 | * | 2/1987 | Lin et al. | 623/23.58 |
| 4,645,509 | * | 2/1987 | Poggi et al. | 623/55 |
| 4,662,887 | * | 5/1987 | Turner et al. | 623/23.58 |
| 4,728,520 | * | 3/1988 | Ashman et al. | 623/23.58 |
| 4,743,632 | * | 5/1988 | Marinovic | 623/23.58 |
| 5,053,274 | | 10/1991 | Jonas | 428/332 |
| 5,366,508 | * | 11/1994 | Brekke | 623/23.58 |
| 5,376,120 | * | 12/1994 | Sarver et al. | 623/23.58 |
| 5,522,895 | * | 6/1996 | Mikos | 623/23.58 |
| 5,643,641 | | 7/1997 | Turchan et al. | 427/595 |
| 5,786,057 | * | 7/1998 | Lyden et al. | 428/52 |
| 5,827,904 | * | 10/1998 | Hahn | 623/23.58 |
| 6,116,911 | * | 9/2000 | Biermann et al. | 623/23.58 |

OTHER PUBLICATIONS

Auger et al., *Proc. Inst. Mech. Eng.*, H–207, 1993, pp. 25–33.
Axelrood et al., *Rubber Age*, 88, 1960, pp. 465–471.
Drews et al., *Soc. Biomaterials Trans.*, 25th Ann. Mtg., 1999, p. 601.
Kohler et al., *J. Am. Chem. Soc.*, 49, 1927, pp. 3181–3188.
McClure et al., *Proc. Inst. Mech. Eng.*, H–210, 1996, pp. 89–93 (Abstract).
McGovern et al., *Soc. Biomaterials Trans.*, 25th Ann. Mtg., 1999, p. 452.
Rapp, *Orthopaedics Today*, Jan./Feb. 1998, pp. 1 & 10.
Townley, *Ceramic Trans.*, 48, 1995, pp. 23–34.
Townley et al., U.S. provisional patent appl. 60/113575 filed Dec. 24, 1998.
Townley et al., U.S. provisional patent appl. 60/123613 filed Mar. 10 1999.
Various authors, *Soc. Biomaterials Trans.*, 24th Ann. Mtg., Apr. 22–26, 1998: Jacobs, p. XLVII; Goodman, p. XLVIII; Ramamurti et al., p. 5; Goodman et al., p. 58; Hsu et al., p. 72; Labow et al., p. 74; Lee et al., p. 114; McCloskey et al., p. 133; Tanzi et al., p. 176; Archambault et al., p. 251; Santerre et al., p. 254; Weisberg et al., p. 305; Martin et al., p. 306; Tang et al., p.363, Tang et al., p.371; White et al., p. 385; Wang et al., p. 393; Huang et al., p.398; Clineff et al., p. 445; Amstutz et al., p. 447; Lee et al., p. 515; Jahangir et al., p. 519; Cohen et al., p. 523.

* cited by examiner

*Primary Examiner*—Paul J. Hirsch
(74) *Attorney, Agent, or Firm*—Christopher John Ruoy

(57) ABSTRACT

An article of manufacture for load bearing medical use such as a joint implant suitable for total joint replacement. The article comprises a polyurethane-containing component and is monolithic with respect to polyurethane-containing component(s). The joint for long term load applications is structurally an articulated joint and the polyurethane component provides a surface for articulation with the polyurethane.

20 Claims, 47 Drawing Sheets

HIP ACETABULAR CUP (SECTION)

LAYER OF SURGICAL CEMENT
BONE
FEMORAL HEAD (MAY BE IMPLANT)
PU CUP

A: Polyol was 50% PTMO650+50%PTMO1000;
B: Polyol was 80% PTMO650+20%PTMO1000;
TMP=0: Extender was 1,4-BD only;
TMP=5% Extender was 95% 1,4-BD+5%TMP

TOUGHNESS OF
POLYURETHANE ELASTOPLASTICS

A: Polyol was 50% PTMO650 + 50% PTMO 1000;
B: Polyol was 80% PTMO650 + 20% PTMO1000;
TMP=0: 1, 4-BD only; TMP=5%: 95% 1, 4-BD + 5%TMP THE EFFECT OF ISOCYANATE INDEX ON TENSILE STRENGTH OF POLYURETHANE ELASTOPLASTICS BASED ON PPDI PREPOLYMER OF 50% PTMO650 AND 50% PTMO1000

TMP=0: 1, 4-BD only;
TMP=5%: 95% 1, 4-BD + 5% TMP.

HIP ACETABULAR CUP (SECTION)

KNEE TIBIAL TRAY LINER

POLYURETHANE AND SO FORTH CONTAINING JOINTS

CROSS-REFERENCE CLAIMS OF PRIORITY

This claims the benefit under 35 USC 119(e) of provisional application Nos. 60/113,575 filed Dec. 24, 1998 and 60/123,613 filed Mar. 10, 1999. The specifications of those U.S. patent applications are incorporated herein by reference.

FIELD

The present invention concerns a polyurethane-containing, load-bearing prosthetic joint implant for use in total joint replacement arthroplasty. Further or alternatively, the joint or component of it may contain a polyurethane-urea, polyurea and/or polyisocyanurate, and so forth composition, or analog thereof.

BACKGROUND

In the current conventional practice of total joint replacement, the concave surface of an ultra high molecular weight polyethylene (UHMW-PE) implant mates and articulates with the convex surface of a hard metallic or ceramic component. For example, in enarthrodial joints such as the hip, a metal or ceramic ball is articulated in match with an UHMW-PE acetabular cup; in ginglymus type joints such as the knee, the hard distal femoral replacement component articulates with a mated UHMW-PE tibial implant. Although UHMW-PE, which was developed and introduced for general use by Dr. John Charnley of England in the late 1960s, has proven to be exceptionally durable, this material is, nonetheless, vulnerable to an unfavorably high rate of wear that may result in a premature failure of the procedure. For the most common total joint coupling currently in use, i.e., cobalt-chrome alloy on UHMW-PE, the polyethylene wear rate is typically on the order of 0.1 to 0.3 mm annually, resulting in the proliferation of billions of wear particles per year. Over the subsequent years, the massive over-loaded accumulation of particulate wear debris, including a substantive percentage of submicron sized particles, gains access to the bone-prosthetic interface and induces an adverse foreign body reaction associated with phagocytic activity and the attendant release of bone resorptive chemical mediators (periprosthetic osteolysis). Structural bone loss due to debris-induced periprosthetic osteolysis is now commonly cited as a major etiological factor in implant loosening and failure of joint replacement procedures. See, e.g., Jacobs, *Soc. Biomaterials Trans.,* April 1998, p. XLVII. See also, Goodman, Id., p. XLVIII; Ramamurti et al., Id., p. 5; Goodman et al., Id., p. 58; Clineff et al., Id., p. 445; Amstutz et al., Id., p. 447. But see, Townley, *Ceramic Transactions,* Vol. 48, pp. 23–34, 1995 (structure of implant to physiologically stress load remaining bone stock may play part in ameliorating or precluding initial loosening to hinder or preclude osteolysis).

Appropos the present invention, nevertheless, of known art from other researchers, it has been reported extensively that polyurethane or polyurethane-containing polymers have been successfully employed as biocompatible implants for the replacement of tendons and for other body structures such as arteries, veins and so forth. See, e.g., Hsu et al., *Soc. Biomaterials Trans.,* April 1998, p. 72; Labow et al., Id., p. 74; Lee et al., Id., p. 114; McCloskey et al., Id., p. 133; Tanzi et al., Id., p. 176; Archambault et al., Id., p. 251; Santerre et al., Id., p. 254; Weisberg et al., Id., p. 305; Martin et al., Id., p. 306; Tang et al., Id., p. 363; Tang et al., Id., p. 371; White et al., Id., p. 385; Wang et al., Id., p. 393; Huang et al., Id., p. 398; Lee et al., Id., p. 515; Jahangir et al., Id., p. 519; Cohen et al., Id., p. 523. Of course, polyurethanes and polyurethane elastomers are well known as structural components and for other uses outside the field of medicine as well. See, e.g., Jonas, U.S. Pat. No. 5,053,274; Axelrood & Frisch, *Rubber Age,* Vol. 88, pp. 465–71, 1960.

In a recent preliminary study, it has been additionally reported that six patients received a knee hemi-arthroplasty for unicompartmental osteoarthritis in Norway from the surgical team of Engebretsen et al., utilizing a flowable, prepolymerized polyurethane polymer, which was molded in vivo and subsequently allowed to polymerize to a hardened state to replace only the degraded articular surface of the pathologically involved tibial plateau. See, Rapp, *Orthopaedics Today,* January/February 1998, pp. 1, 10. However, a polyurethane-containing implant, or for that matter any other plastic type implant material that is contrived to replace only one side of an arthritically degraded and rough bony articulation (hemi-arthroplasty a la the Norwegian method) in opposition to the mirror-imaged equal roughness of the unreplaced joint surface is generally known to be exceptionally vulnerable to rapid abrasive wear degradation and failure of the procedure early on following resumption of weight bearing. Utilizing a plastic material of any sort that articulates in opposition to a bony or cartiligenous surface is not considered to be a viable procedure.

Many years ago, over a span of two years (1960–1961) Charles O. Townley, M.D., utilized a similar in vivo "cured" polyurethane polymer to replace the acetabulum in eleven patients with crippling, severely advanced osteoarthritis of the hip joint. In those cases, however, the polyurethane-containing acetabular implant was used in conjunction with a metallic femoral component to provide a total articular joint replacement. While all of the patients sustained an exceptionally good, pain-free result early on, i.e., over a postoperative follow up time ranging from two to three years, the procedures subsequently failed due to fragmentation of the polyurethane acetabular implant under the duress of normal weight-bearing activities. Looking back upon it, that was an apparent reflection of the primitive nature and structural inadequacy of the polyurethane polymer available for use then, and, the inability to replicate, in vivo, the level of polymerization required to produce a more satisfactorily durable, high density, load-bearing implant. Nonetheless, the early encouraging results of this initial introduction to the concept of a metal-on-plastic total joint arthroplasty strongly supported the rationality of the procedure as a viable mode of treatment, awaiting only the development of a more durable polymer replacement material. Although Charnley's subsequent introduction of in vitro polymerized, high density polyethylene later on in the late 1960s appeared to be the solution to the problem and has, indeed, while becoming an accepted mainstay in the art, extended the life expectancy of total joint procedures for many fruitful years of normal pain free function, the extensive long term clinical experience with this material has demonstrated its time related wear limitations and the associated propensity for latent complications as heretofore cited.

Thus, the current material of choice for prosthetic "socket" sides of joints such as the hip, shoulder, knee, and so forth is UHMW-PE. However, in addition to the foregoing considerations, UHMW-PE cannot be heat-sterilized, and is vulnerable to time-related, on-shelf degradation. Furthermore, it is a rigid plastic material, which is subject to wear and deformation under complex stresses, and to stresscracking on long term exposure to fluids. Accordingly, there is a need for another suitable plastic material for this application which should result in prolonged longevity in wear and resistance to degradation.

More recently, McGovern et al., *Soc. Biomaterials Trans.,* 25th Annual Meeting (1999) page 452, reported on thermo-mechanical properties of polyurethane elastomers used as coating and bearing materials; and Drews et al., Id., at 601, reported on the fabrication of a cushion bearing, elastomeric polyurethane composite acetabular cup. Therein, these reported that certain low modulus polyurethanes or polyurethane elastomers had been proposed for total joint arthroplasty since they encourage fluid film lubrication or provide enhanced tribological conditions, which was a "cushion foam bearing" acetabular cup having a low modulus (20 MPa) polyurethane layer introduced into the joint space. See, Auger et al., "Friction and lubrication in cushion form bearings for artificial hip joints," *Proc. Inst. Mech. Eng.,* H-207 (1993) at pages 25–33. However, the cushion foam bearing only has a certain low modulus polyurethane as a layer for articulation in a multilayered composite. As stated in Drews et al., while these materials display promising viscoelastic and tribological properties, they do not possess the fatigue strength needed for long-term bearing implant applications. See also, for example, McClure et al., "Determination of lubricating film thickness for permeable hydrogel and non-permeable polyurethane layers bonded to a rigid substrate with particular reference to cushion form hip joint replacements," *Proc. Inst. Mech Eng.,* H-210 (1996) at pages 89–93.

It would be desirable to overcome/ameliorate such problems. It would be desirable to fulfill such a longstanding lack and long felt need in the art.

OBJECT AND SUMMARY OF THE INVENTION

The present invention is directed to the singular objective of making available a more durable, load-bearing, biocompatible implant, particularly one with structural characteristics which provide excelling resistance against both the proclivity for friction-induced wear degradation and the potential for cold flow deformation, predominant major factors that determine the survivorship longevity of a total joint replacement procedure.

Appropos of this objective, particular application of the generally remarkable technological advances in the evolving art of polymer fabrication over the span of four decades or so subsequent to Dr. Townley's initial short term, unfavorable experience has resulted in the development of an inordinately superior, in vitro polymerized, load-bearing polyurethane type material which has been demonstrated to transcend the structural characteristics of the highest grade of UHMW-PE that is available for current use, specifically relative to the susceptibility to deformation and friction-induced wear. Characteristics of the particular compositions aside for the time being, as significant as they may be, of great significance is the ability to produce the material in vitro through processing conditions not possible to achieve in vivo: for instance, producing a polyurethane end product of the highest achievable quality, in general, requires an application of tremendous levels of pressure and heat over an extended period of polymerization curing, for example, an in vivo untenebale compression force of up to 20,000-psi in conjunction with a sustained physiologically intolerable material temperature on the order of one hundred to one hundred fifty degrees Celsius (212–322 degrees Fahrenheit). Although, as heretofore cited, polyurethane has been studied and employed extensively for many years as a replacement implant to successfully reconstitute many other diseased body organs, with the exception of Dr. Townley's short lived experience in the early 1960s with the use of an apparent inappropriately "cured" and structurally inferior product and the polyurethane lubrication layer containing cushion foam bearing, it is believed that a polyurethane-containing component has not heretofore been utilized in total joint replacement components; in any case, ex vivo, implantable monolithic polyurethane total joint replacement components are believed to be heretofore unknown, and polyurethane total joint replacement components of any sort having requisite structural integrity are believed to be heretofore unknown.

Accordingly, in fulfillment of the foregoing, the present invention provides a polyurethane-containing, load-bearing prosthetic joint or component therefor, especially one for use in total joint replacement arthroplasty, said joint or component being monolithic with respect to polyurethane component(s) and/or being manufactured ex vivo for in vivo implantation and/or having requisite structural integrity for long-term load bearing joint implant applications; further or as an alternative, the joint or component therefor may contain a polyurethaneurea, polyurea and/or polyisocyanurate, or analog thereof, including halogenated compositions. The joint may include such polyurethane and/or so forth component and another hard, structural component such as metal, ceramic, and so forth, for articulation with said joint component in a total replacement joint implant.

Significantly, by the invention, problems in the art are ameliorated if not overcome. More particularly, embodiments of the invention have excellent properties in longevity of use and resistance to degradation, which may exceed those of even the material of choice from the second millennium, UHMW-PE. Moreover, unlike UHMW-PE, the polyurethane and so forth type joint or joint component of the invention can be heat-sterilized, and be less vulnerable to time-related, on-shelf degradation. In addition, other deficiencies found in UHMW-PE may be ameliorated.

Numerous further advantages attend the invention.

DRAWINGS

The drawings form part of the specification hereof. With respect to the drawings, the following is briefly noted:

Figure 26:
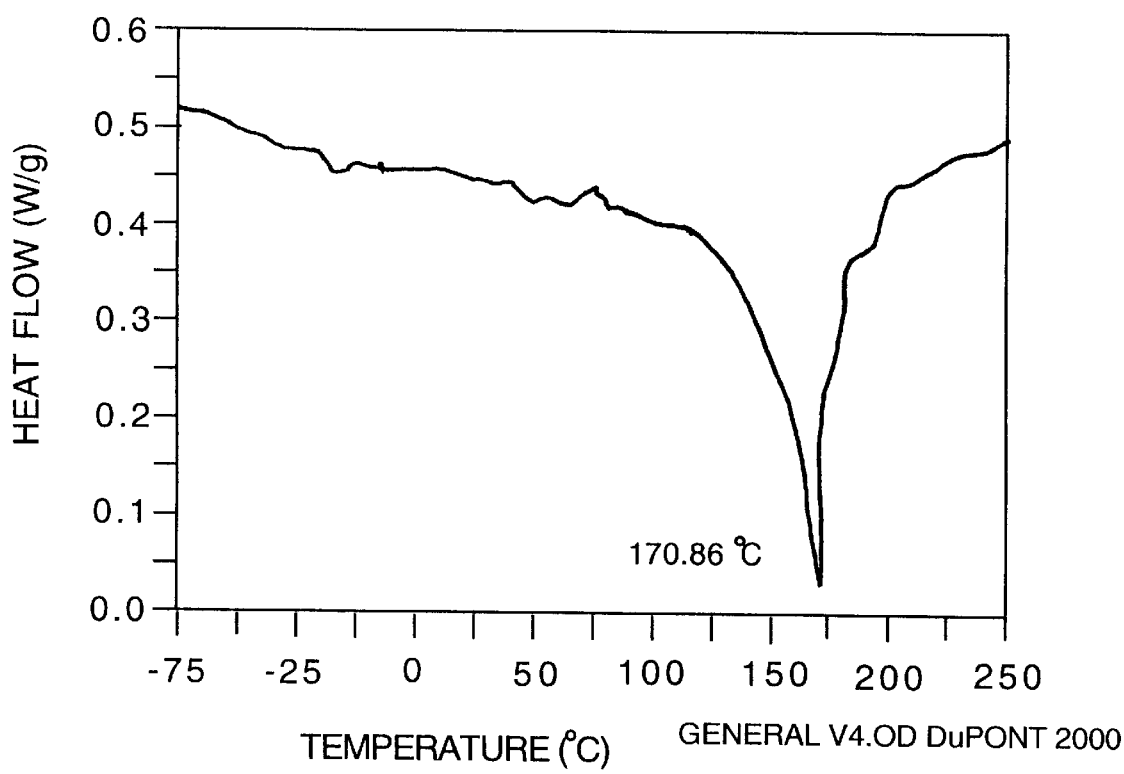

FIG. 26 is a differential scanning calorimetry (DSC) graph of a sample of 80% PTMO-650, 1,4-butandiol (1,4-BD) only, isocyanate index (II): II-102. Note, additional data by graph: hard segment (HS) 65%; dibutyltin dilaurate catalyst (T-12) 0.002%; 4,4'-methylene bis(phenyl isocyanate) (PPDI) prepolymer, plus 4,4'-diphenylmethane diisocyanate (MDI); 10.3 milligram (mg) sample at a 10-degree C per minute scan (10-deg./min.) under nitrogen.

Figure 27:
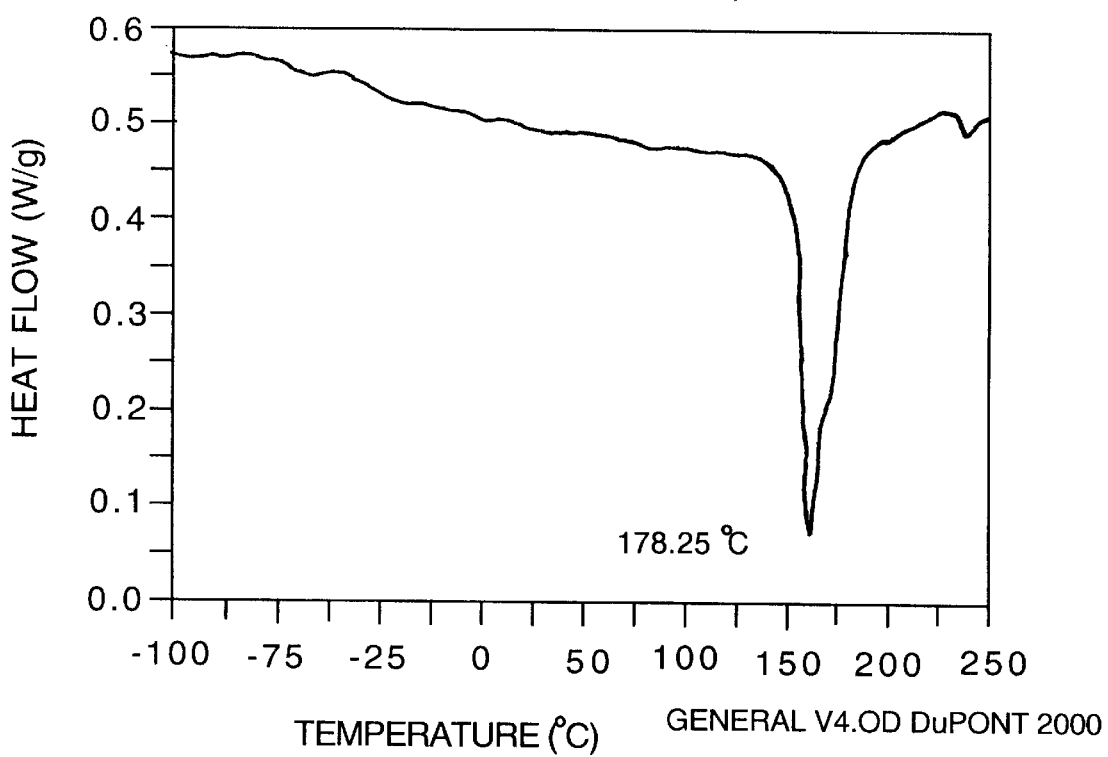

FIG. 27 is a DSC graph of a sample of 80% PTMO-650, 95% 1,4-BD: II-102. Note, additional data by graph.

Figure 28:
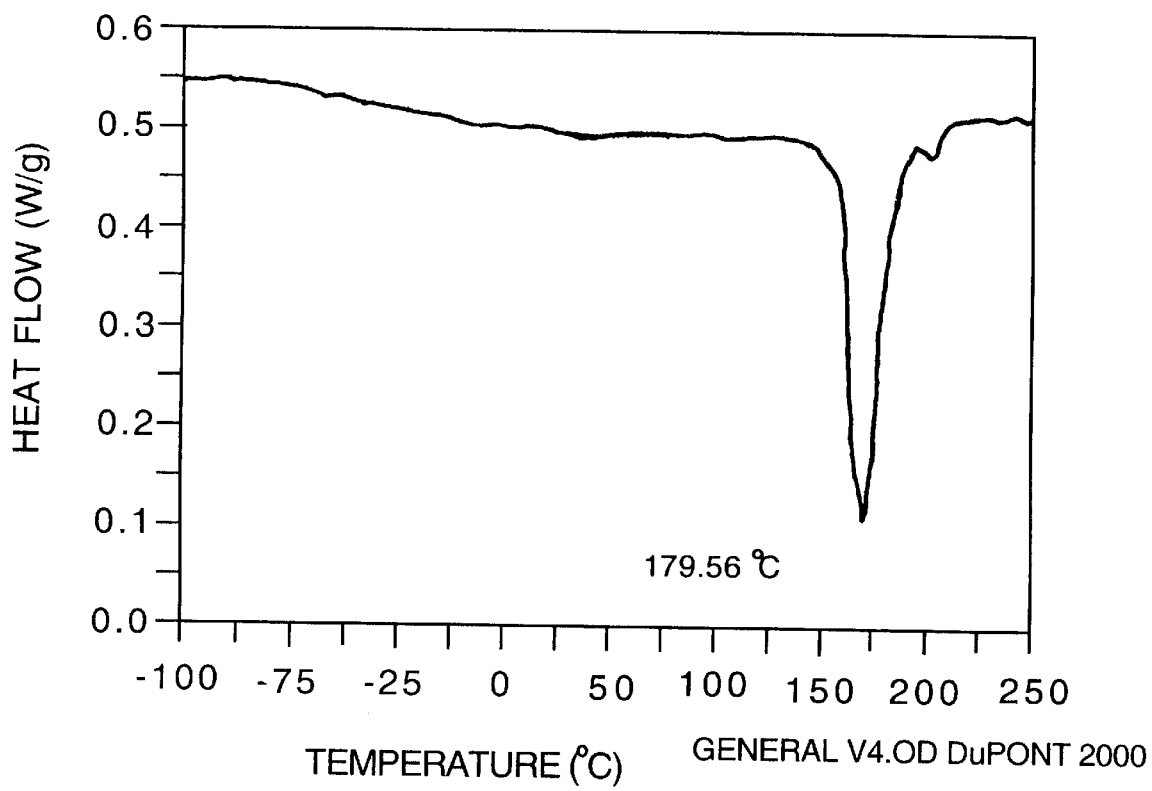

FIG. 28 is a DSC graph of a sample of 50% PTMO-650, 1,4-BD only: II-102. Note, additonal data by graph.

Figure 29:
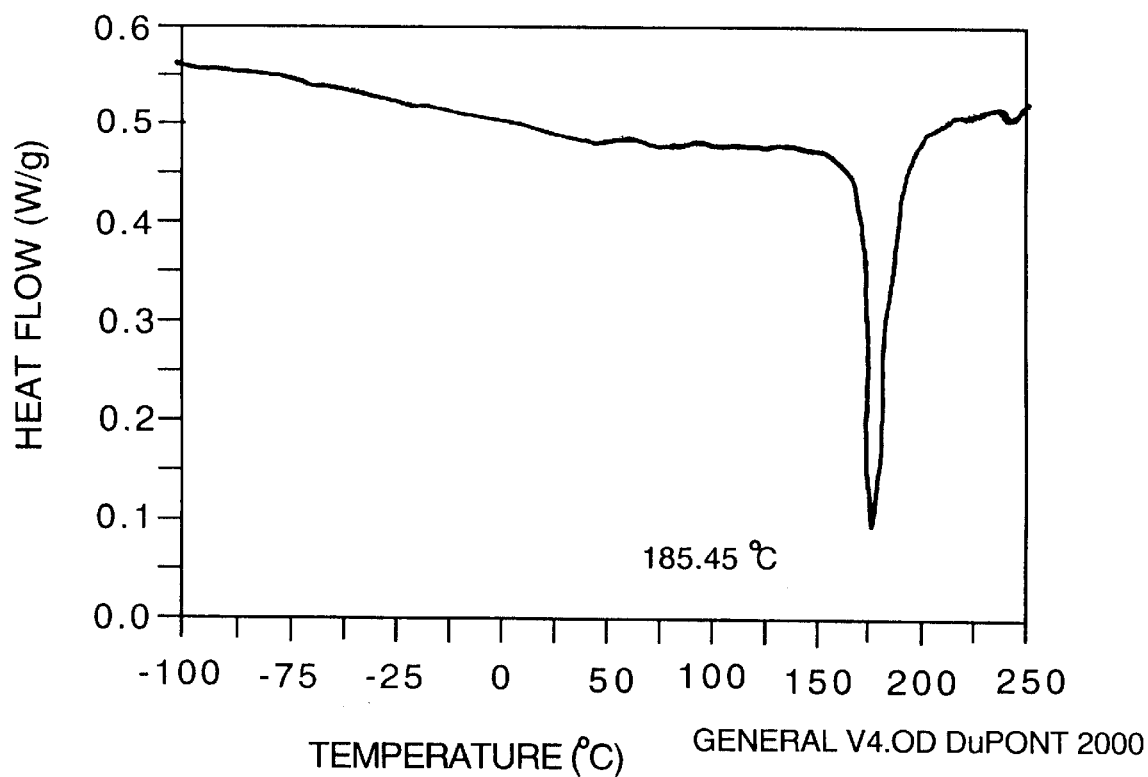

FIG. 29 is a DSC graph of a sample of 50% PTMO-650, 95% 1,4-BD: II-102. Note, additonal data by graph.

Figure 30:
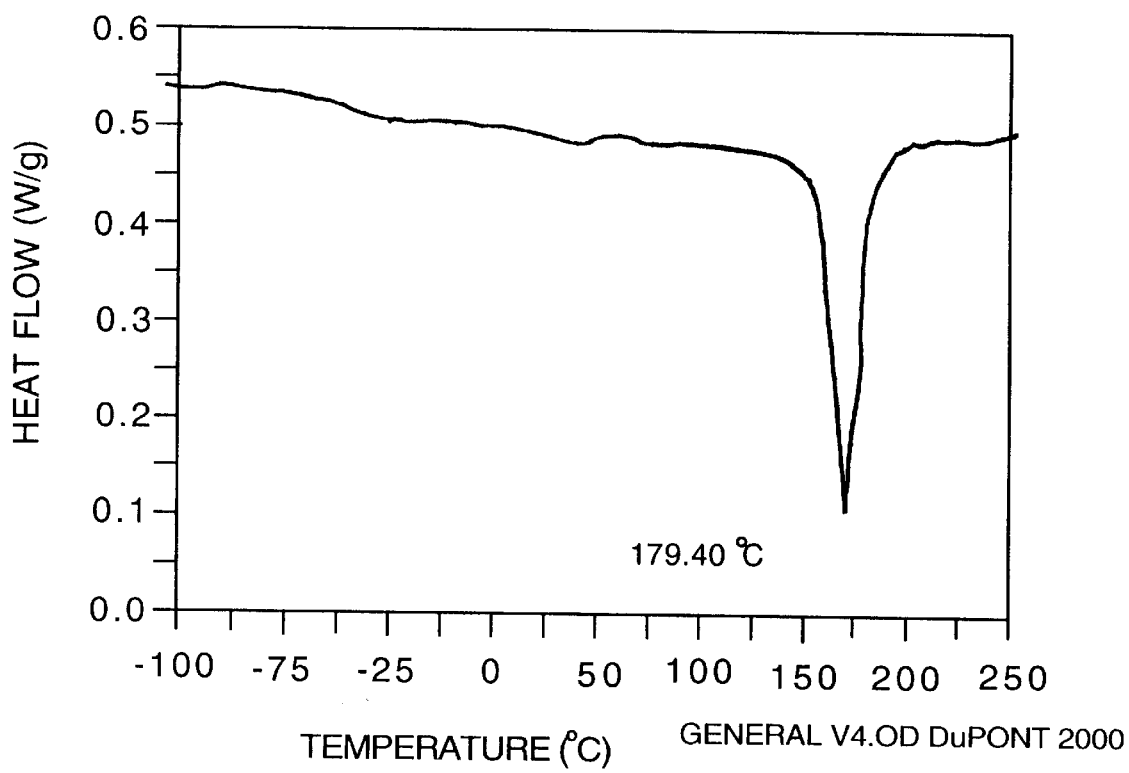

FIG. 30 is a DSC graph of a sample of 50% PTMO-650, 1,4-BD only: II-105. Note, additonal data by graph.

Figure 31:
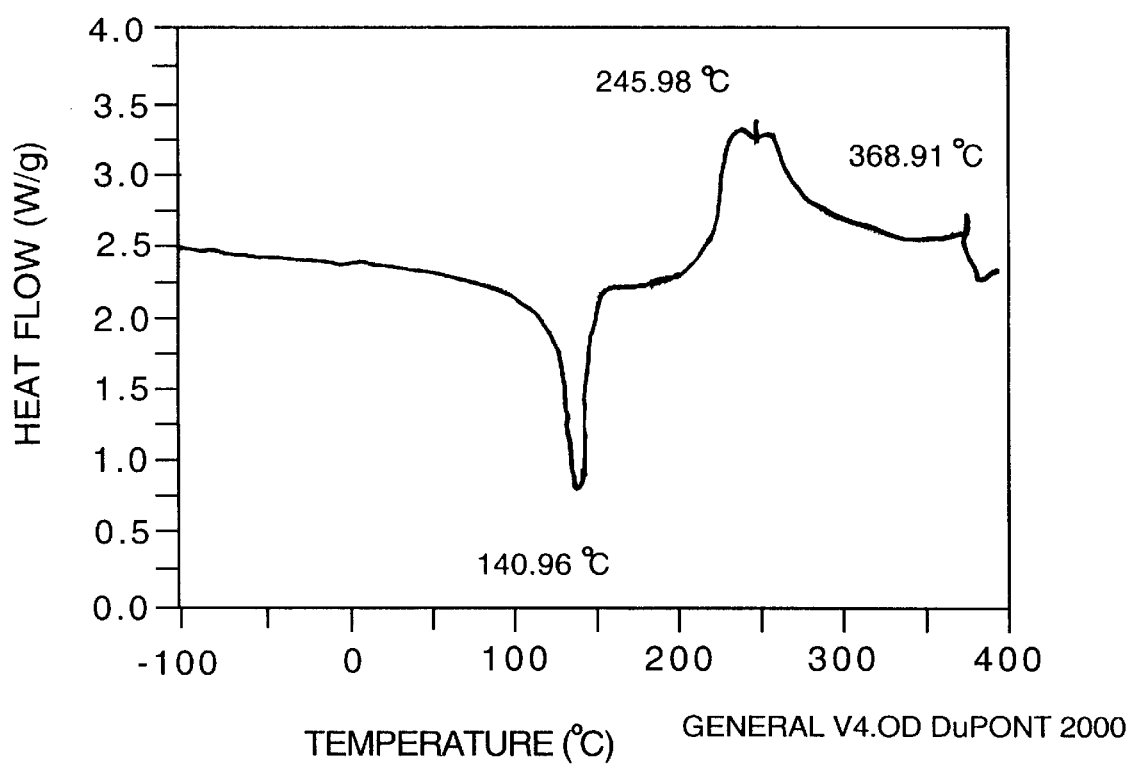

FIG. 31 is a DSC graph of a comparative sample of unfilled high density polyethylene. Note, additonal data about graph.

Figure 32:
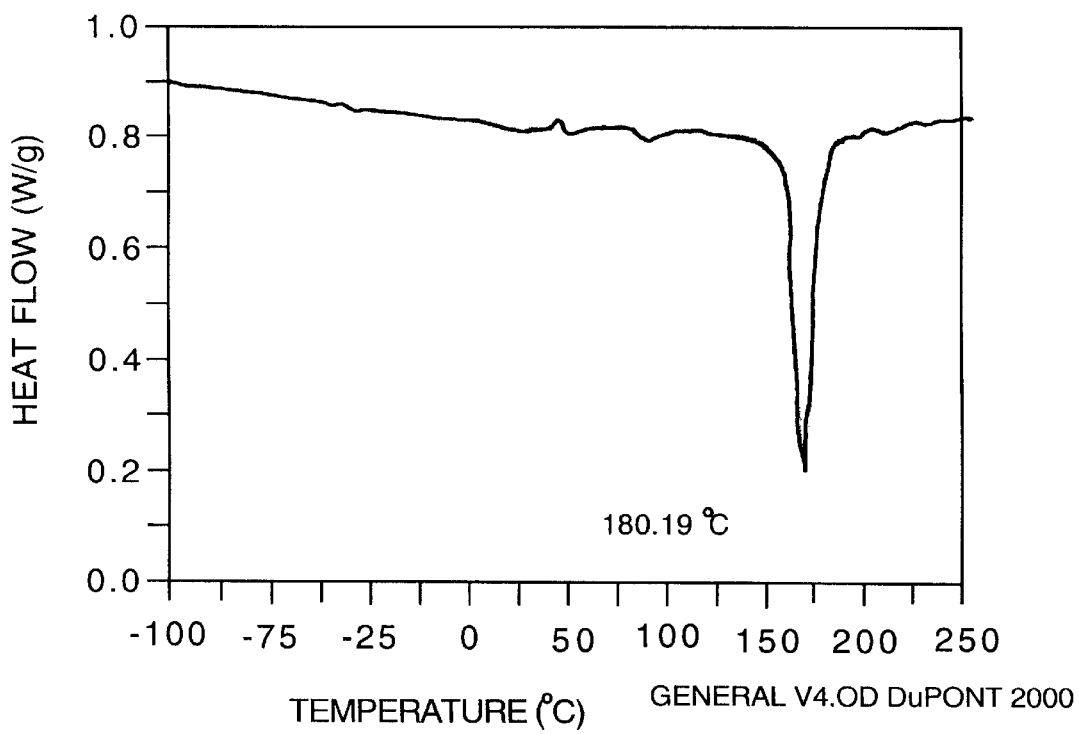

FIG. 32 is a DSC graph of a sample of 50% PTMO-650, 95% 1,4-BD: II-105. Note, additonal data by graph.

Figure 33:
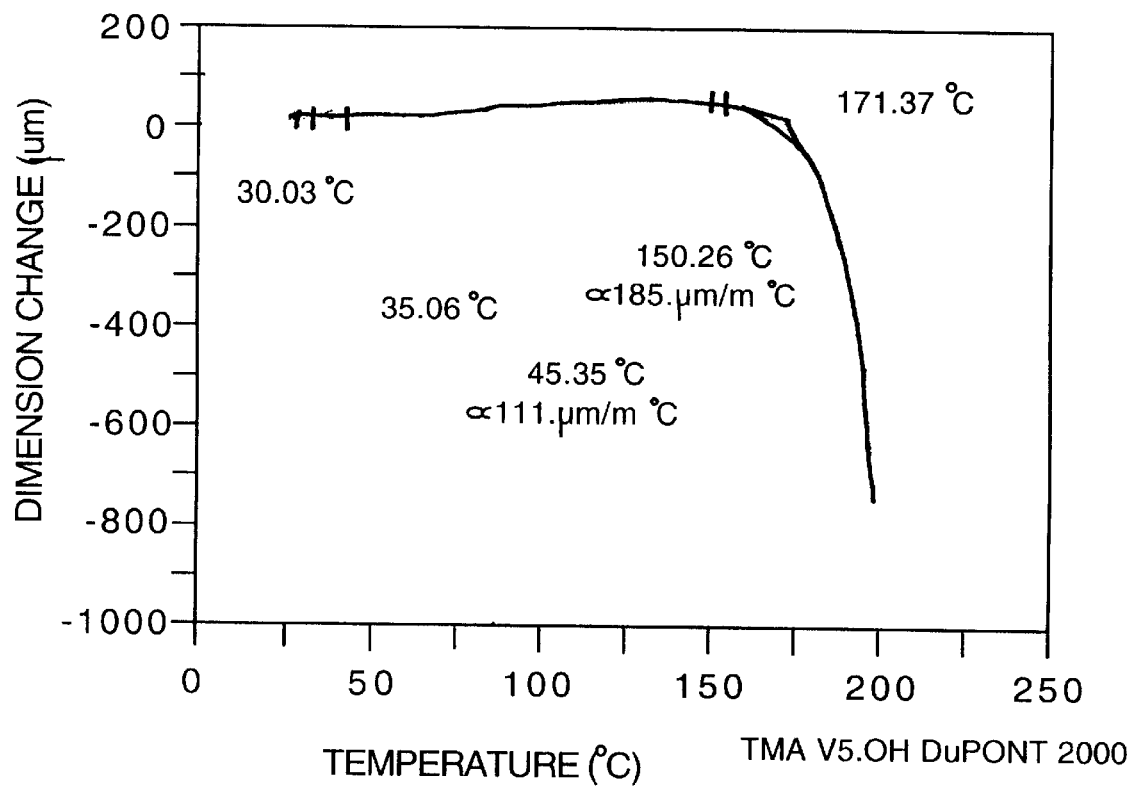

FIG. 33 is a thermo-mechanical analysis (TMA) graph of a sample of 80% PTMO-650, 1,4-BD only: II-102. Note, additonal data by graph: 80% PTMO-650, 1,4-BD only: II-102; 1.884 millimeter (mm) PPDI prepolymer+MDI/80% PTMO-650+PTMO-1000, T-12 0.002%, HS 65% sample analyzed at 10-deg./min.

Figure 34:
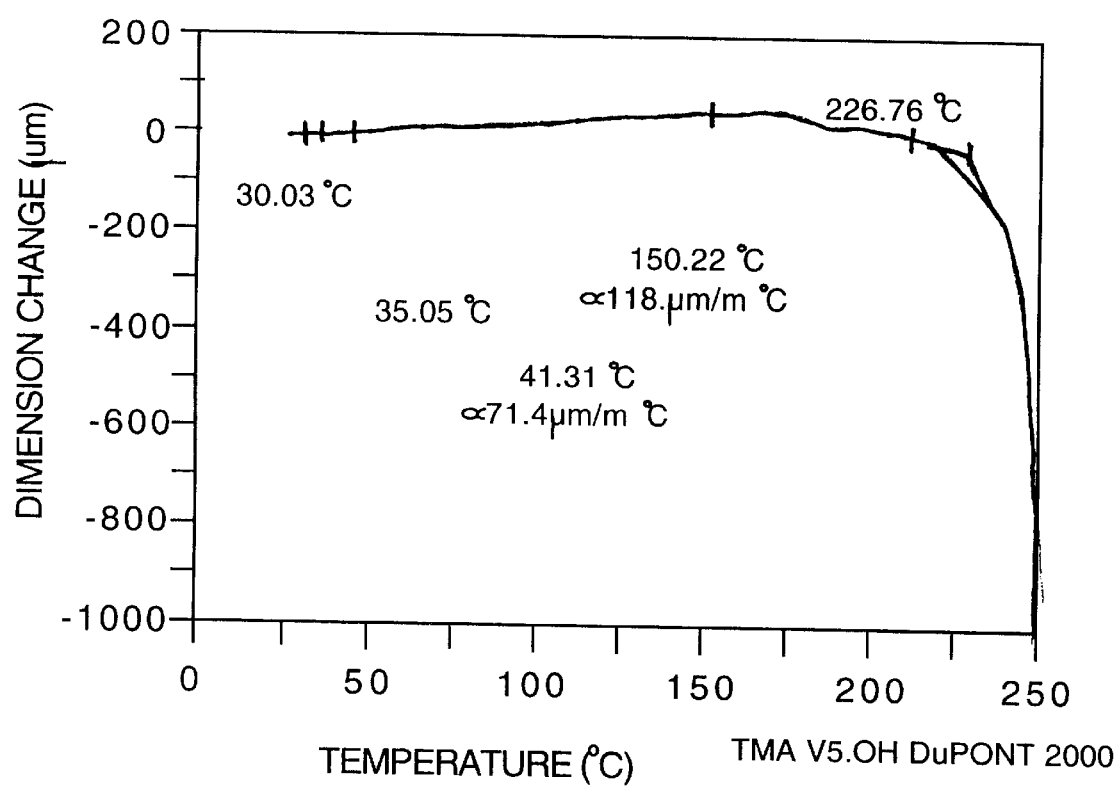

FIG. 34 is a TMA graph of a sample of 80% PTMO-650, 95% 1,4-BD: II-102. Note, additional data by graph.

Figure 35:
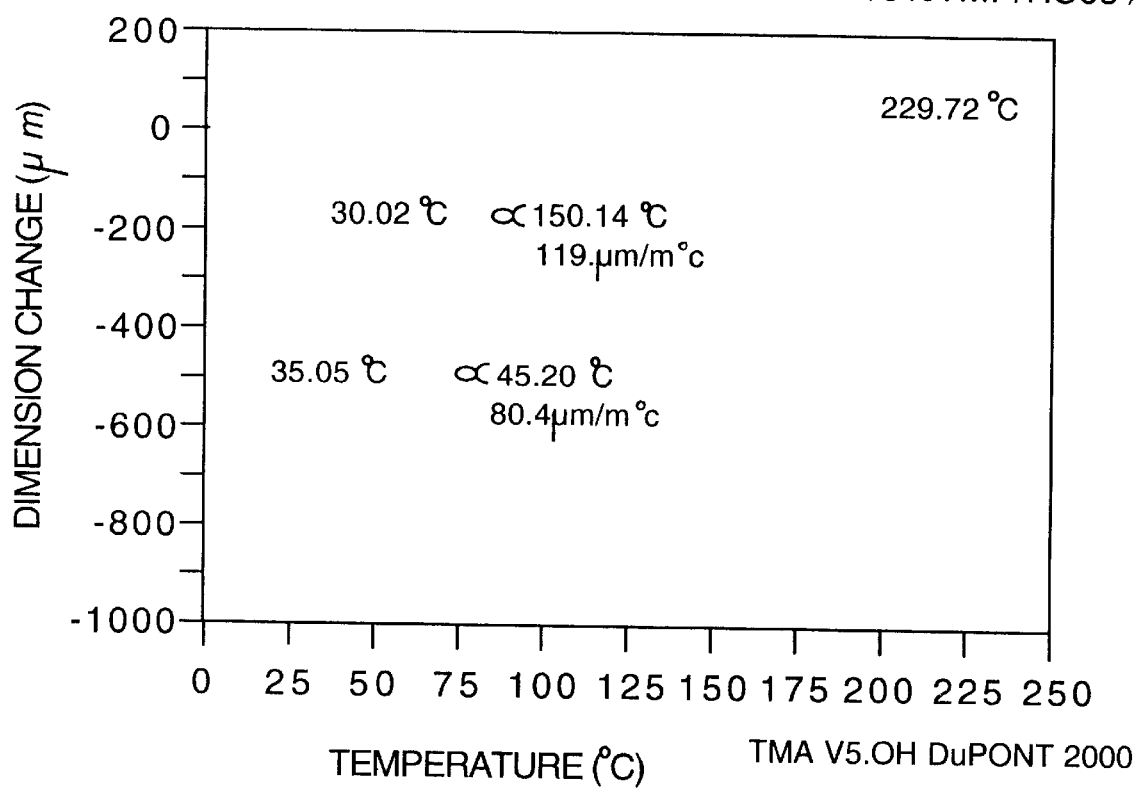

FIG. 35 is a TMA graph of a sample of 50% PTMO-650, 95% 1,4-BD: II-102. Note, additional data by graph.

Figure 36:
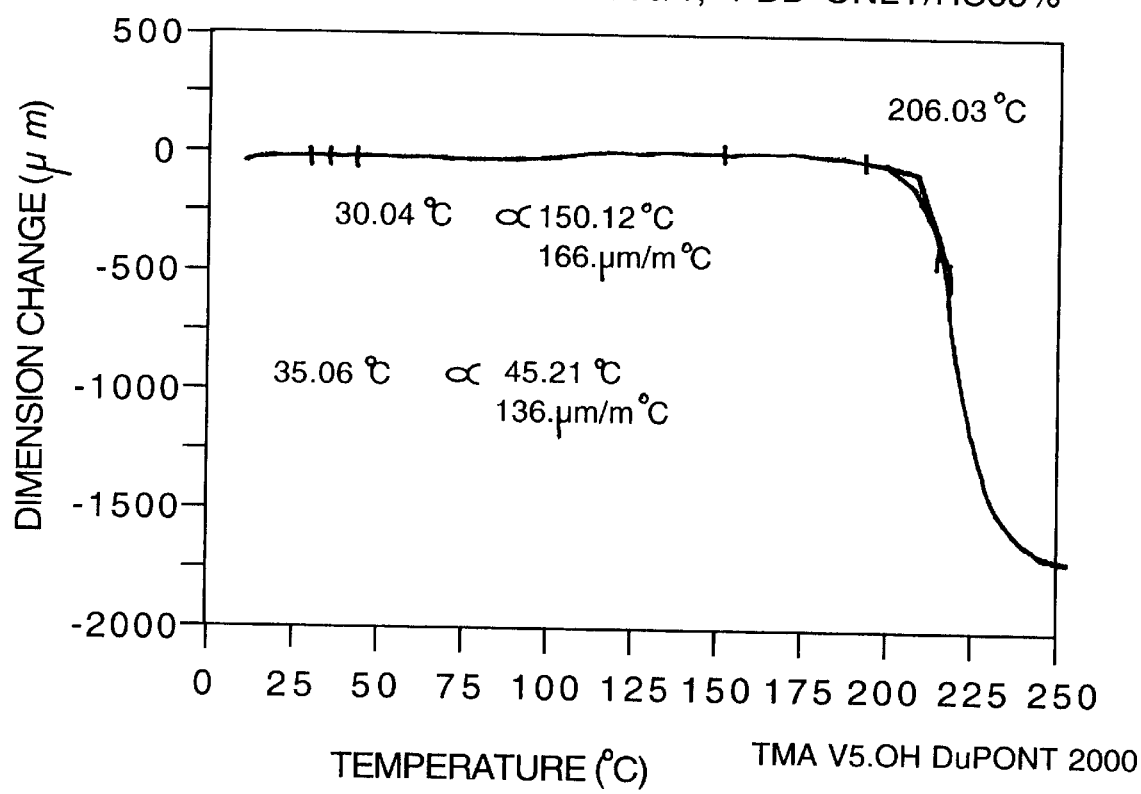

FIG. 36 is a TMA graph of a sample of 50% PTMO-650, 1,4-BD only: II-102. Note, additional data by graph.

Figure 37:
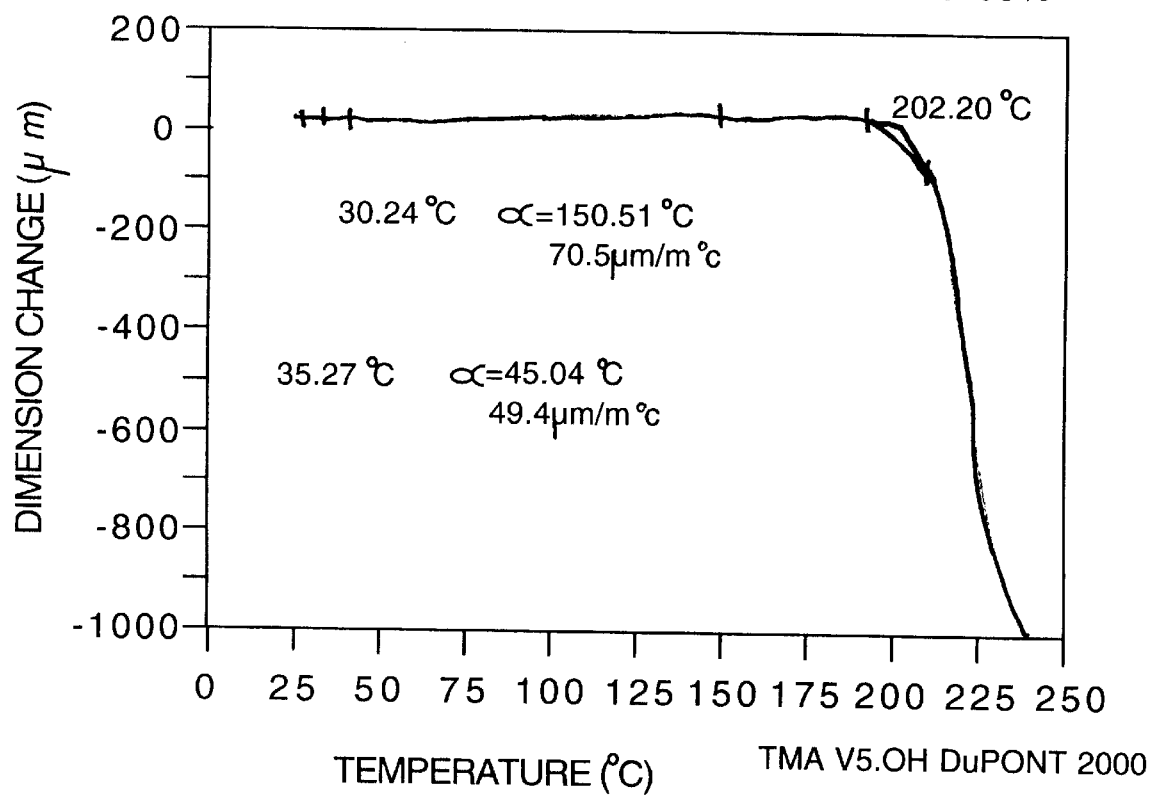

FIG. 37 is a TMA graph of a sample of 50% PTMO-650, 1,4-BD only: II-105. Note, additional data by graph.

Figure 38:
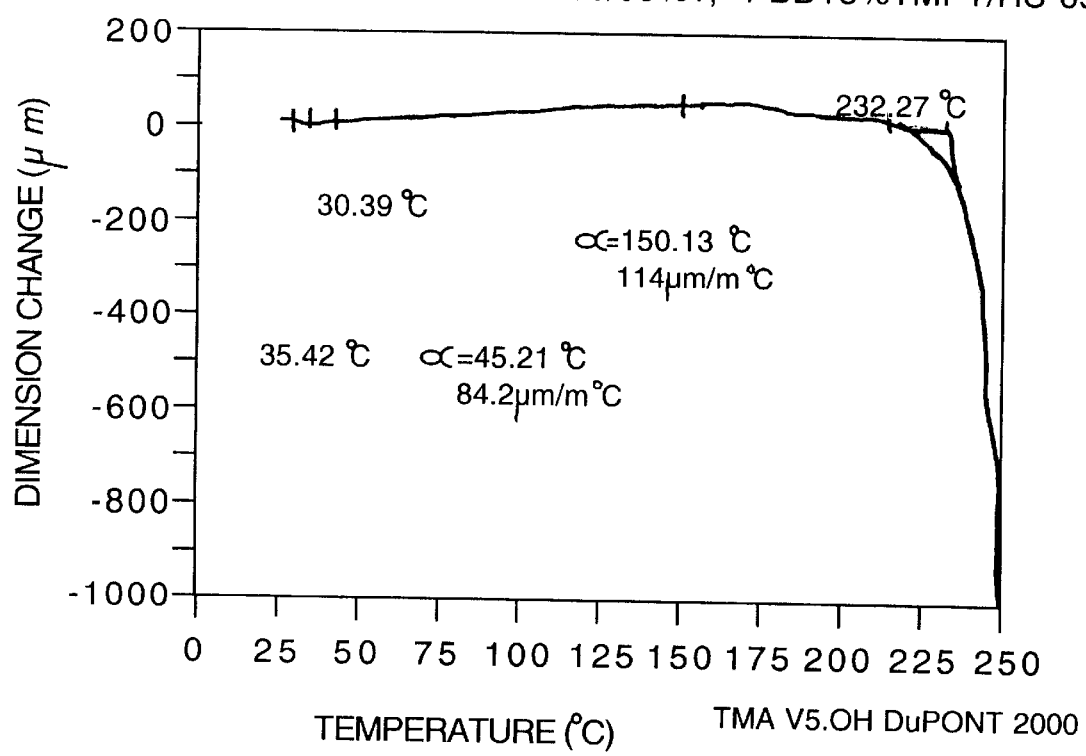

FIG. 38 is a TMA graph of a sample of 50% PTMO-650, 95% 1,4-BD: II-105. Note, additional data by graph.

Figure 39:
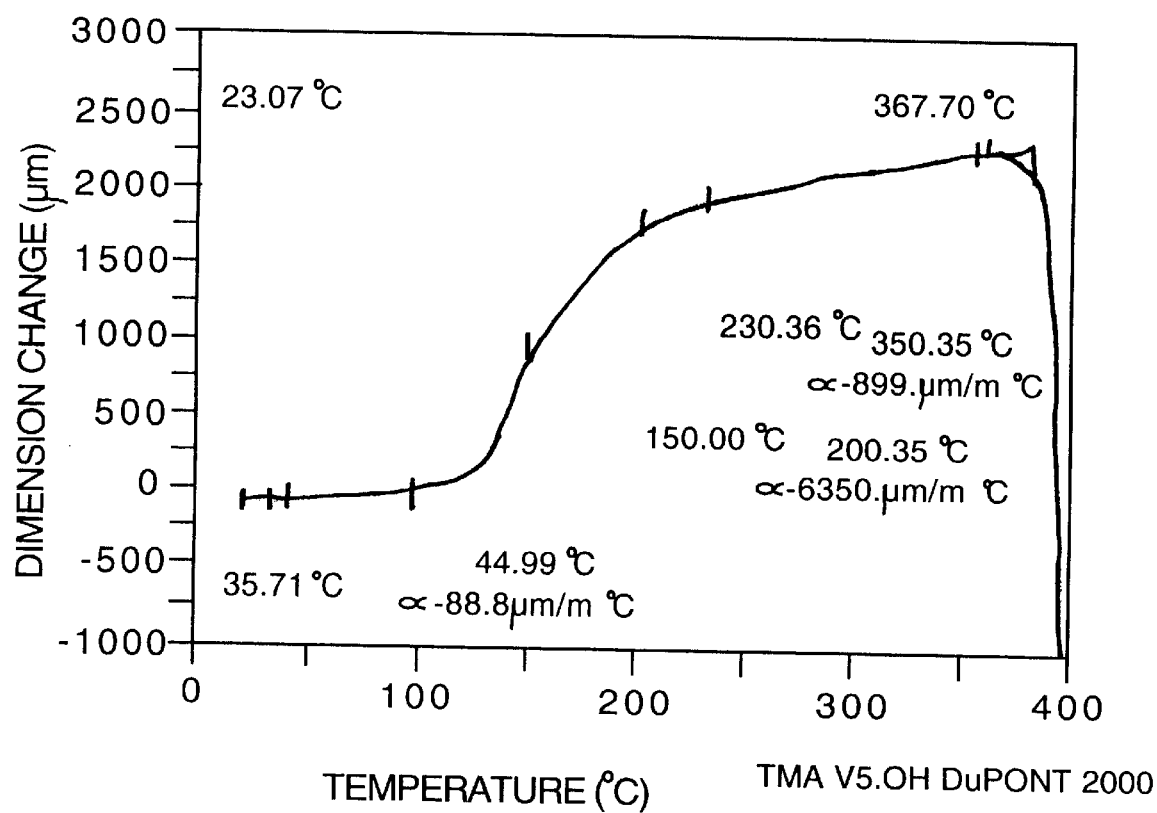

FIG. 39 is a TMA graph of a comparative sample of unfilled high density polyethylene. Note, additional data about graph.

Figure 40:
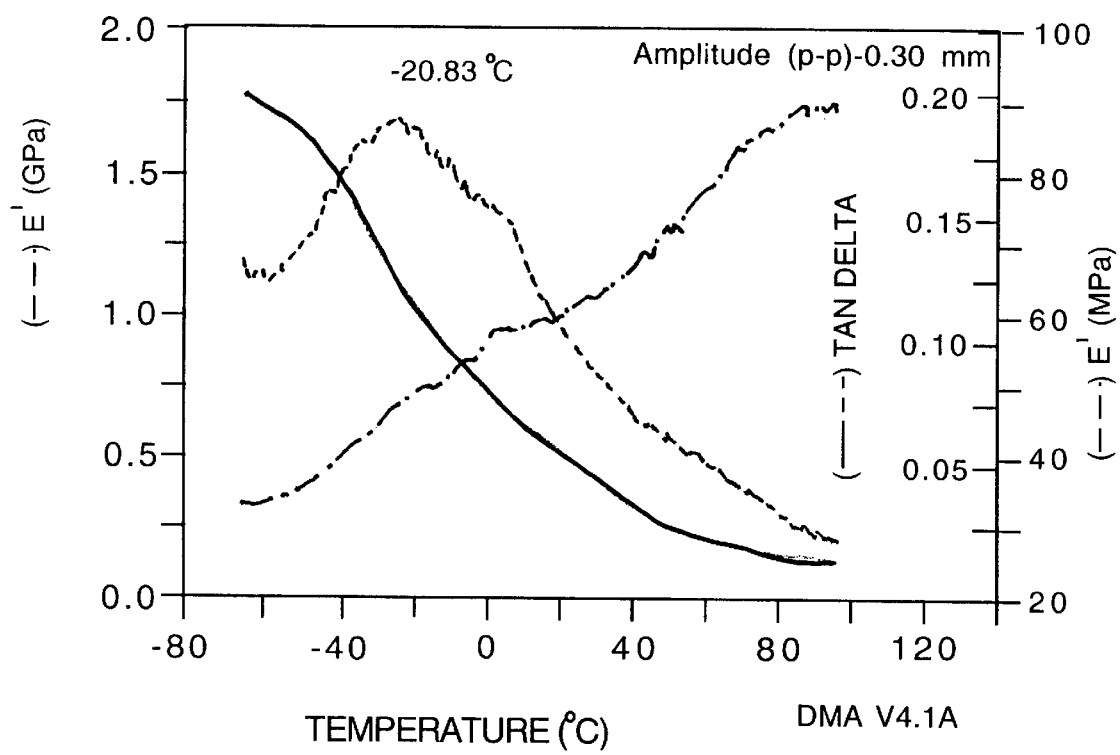

FIG. 40 is a dynamic-mechanical analysis (DMA) graph of a sample of 80% PTMO-650, 1,4-BD only; II-102. Note, additional data by graph: 26.42×13.36×1.02 mm PPDI prepolymer+MDI/80% PTMO-650+20% PTMO-1000, T-12 0.02%, HS 65% sample analyzed from −60 degrees C to one hundred degrees C at 5-deg./min.

Figure 41:
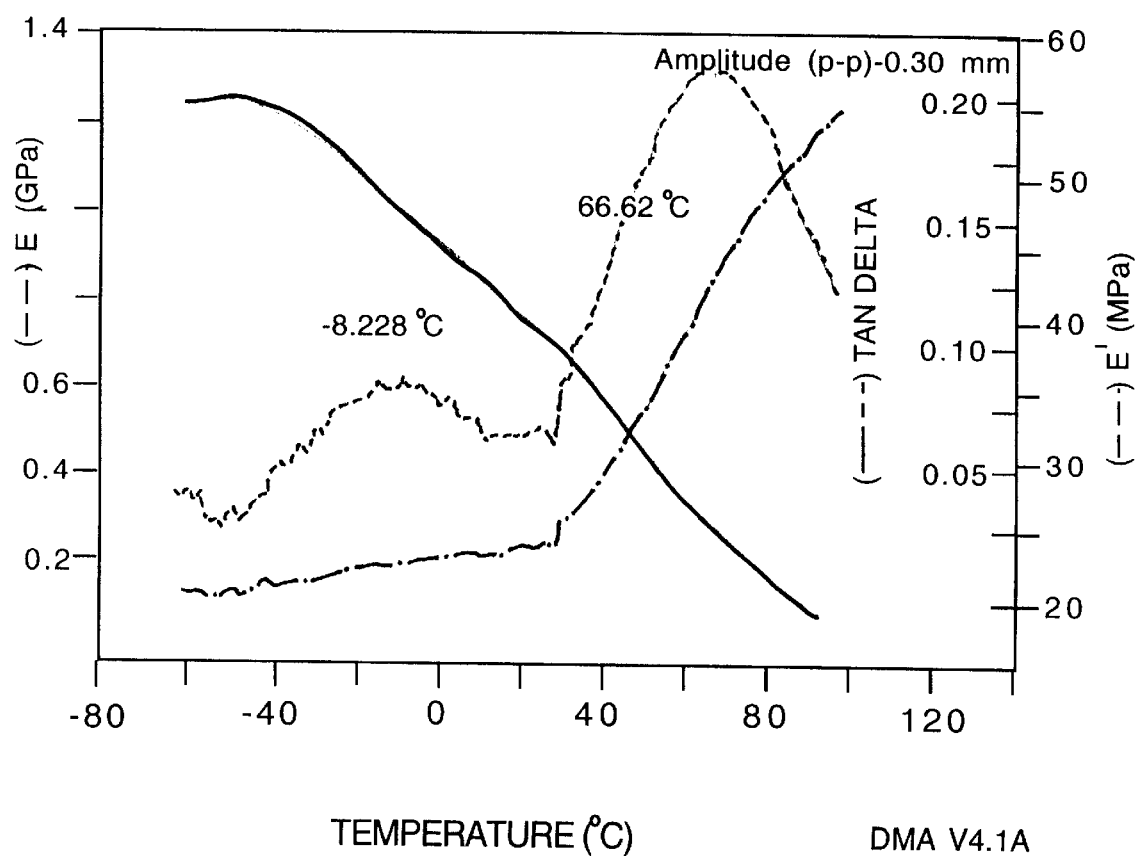

FIG. 41 is a dynamic-mechanical analysis (DMA) graph of a second compariative UHMW-PE sample. Note, additional data about graph.

Figure 42:
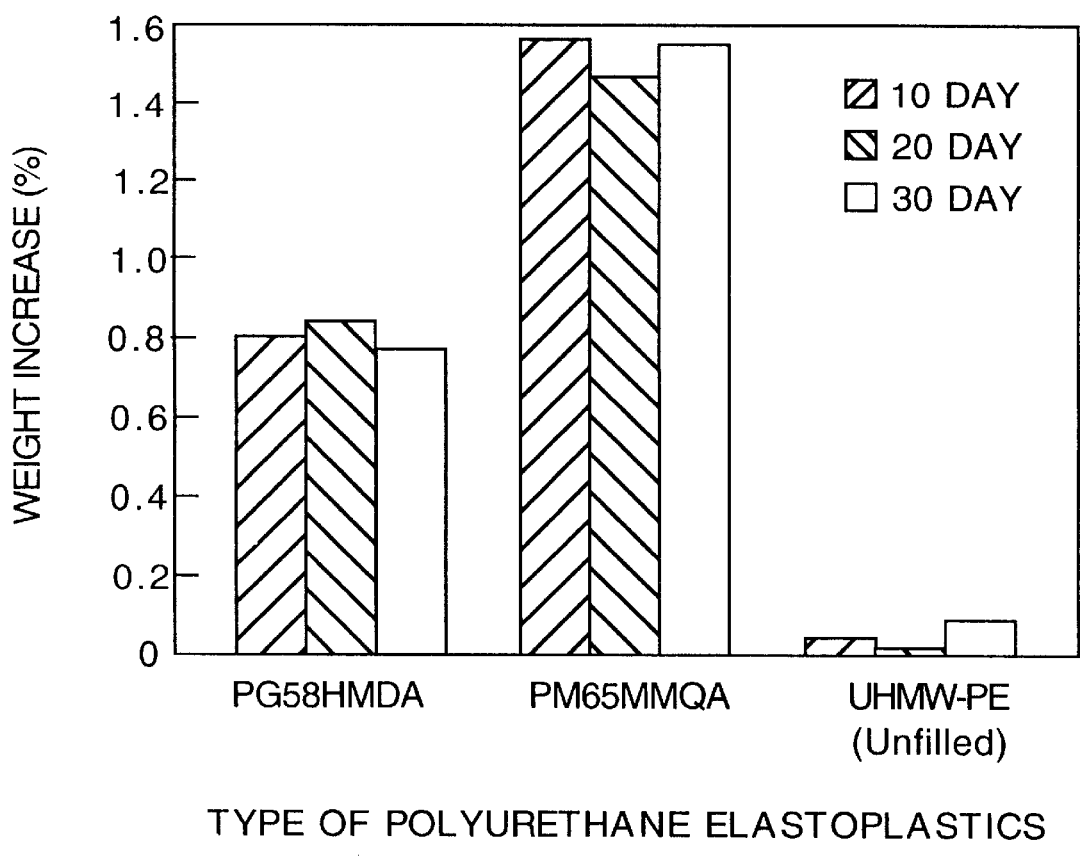

FIG. 42 is a bar graph of effect of saline immersion at forty degrees C on weight change of certain polymers of the invention, with unfilled UHMW-PE comparative.

Figure 43:
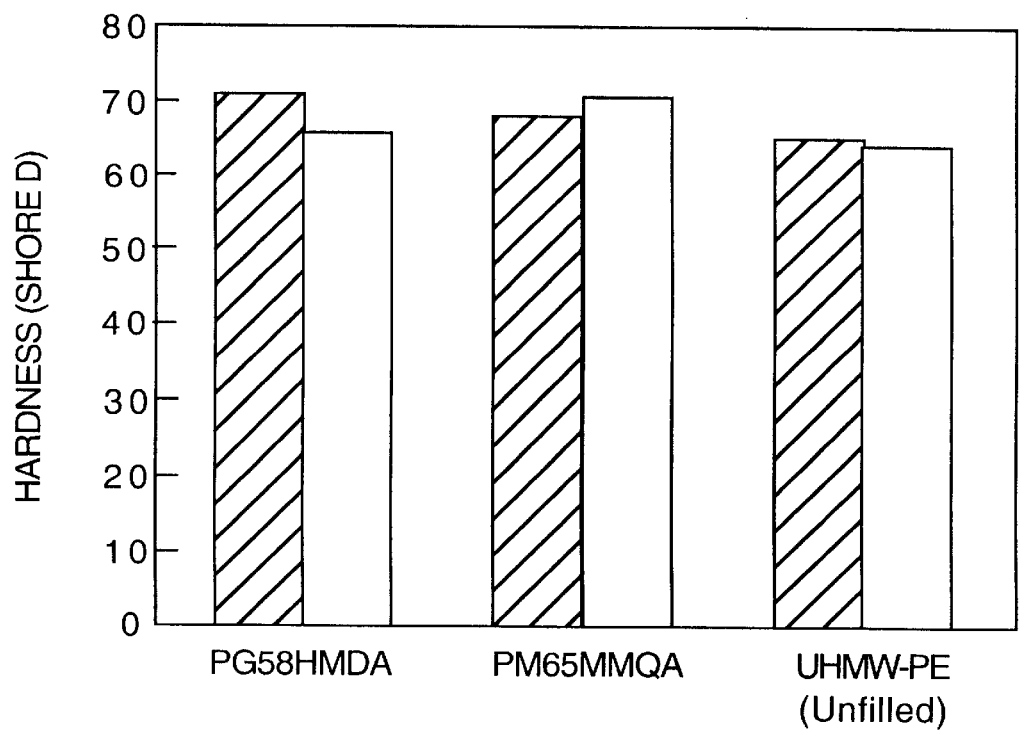

FIG. 43 is a bar graph of effect of saline immersion at forty degrees C on hardness of certain polymers of the invention, with unfilled UHMW-PE comparative.

Figure 44:
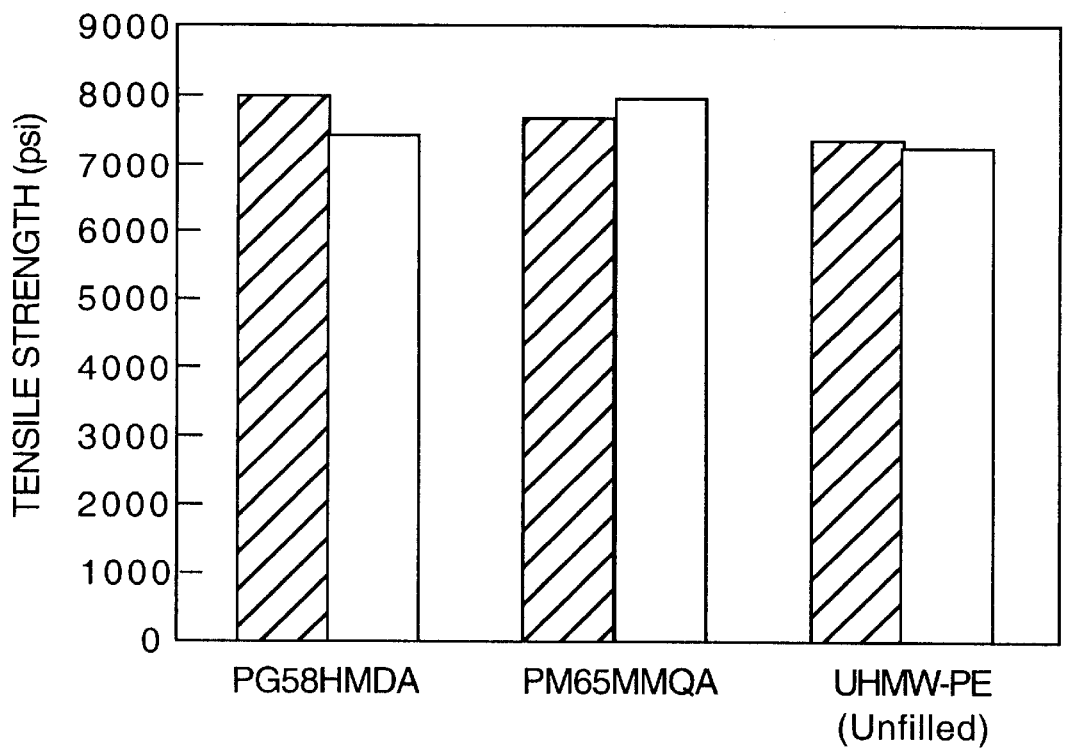

FIG. 44 is a bar graph of effect of saline immersion at forty degrees C on tensile strength of certain polymers of the invention, with unfilled UHMW-PE comparative.

Figure 45:
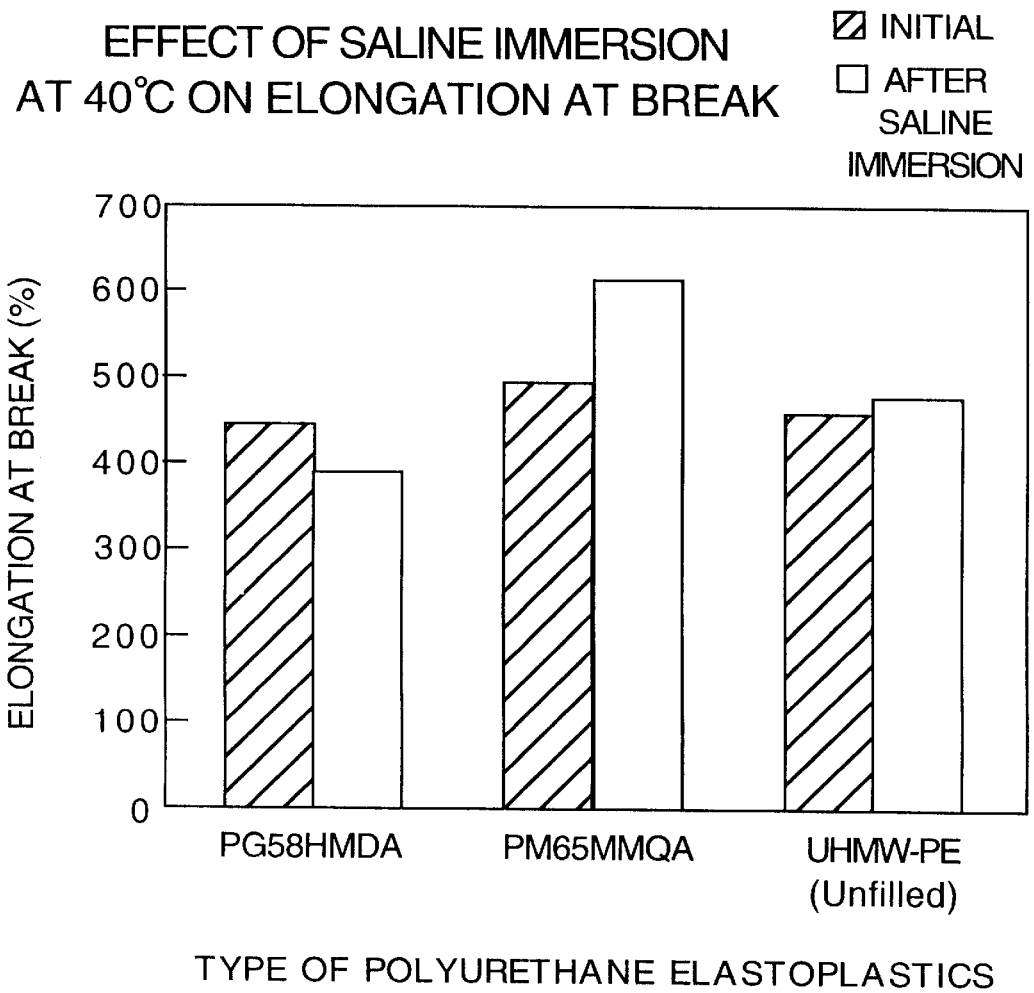

FIG. 45 is a bar graph of effect of saline immersion at forty degrees C on elongation at break of certain polymers of the invention, with unfilled UHMW-PE comparative.

Figure 46:
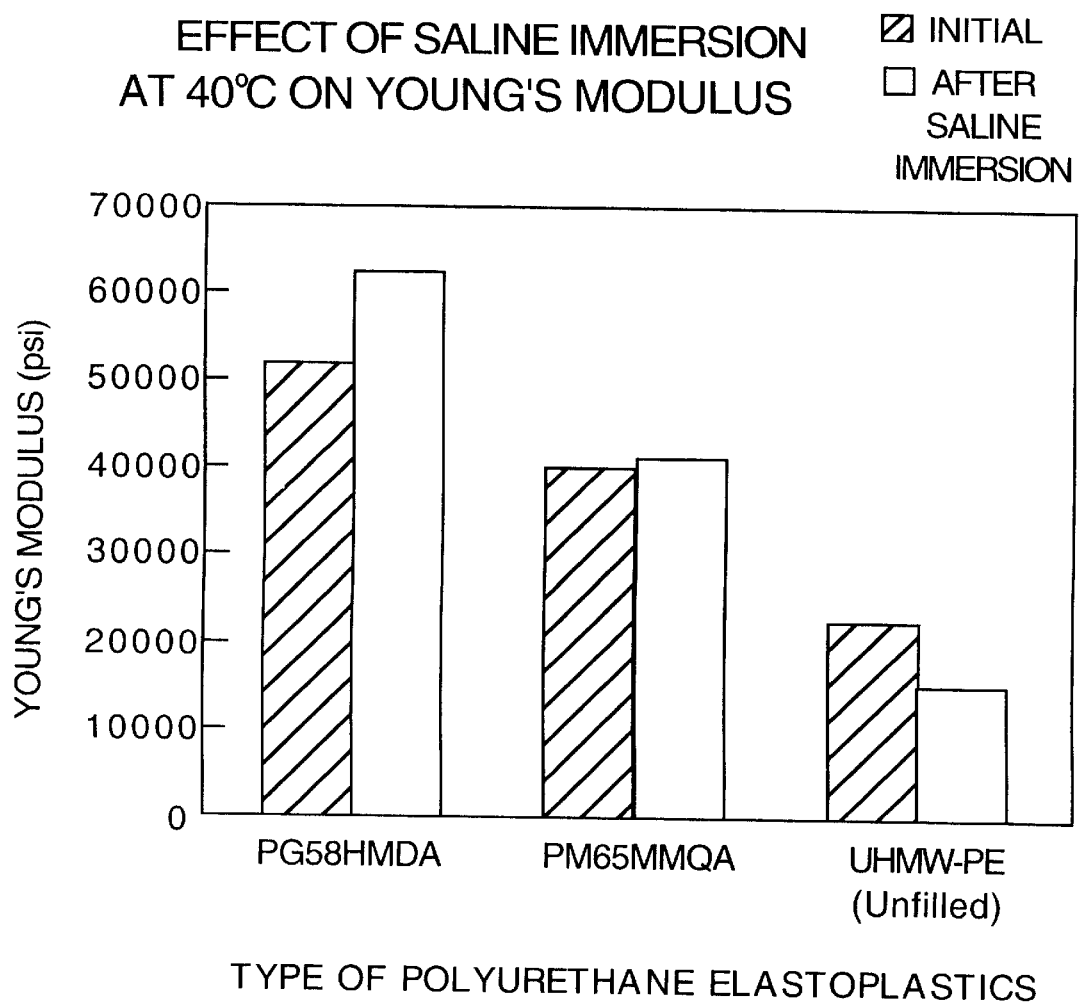

FIG. 46 is a bar graph of effect of saline immersion at forty degrees C on Young's modulus of certain polymers of the invention, with unfilled UHMW-PE comparative.

FIG. 47 presents views of some joint components of the invention, containing (acetabular cup) or being (tibial tray) a monolithic load-bearing joint implant component.

ILLUSTRATIVE DETAIL

The invention can be further understood through the present detail, which may be read in view of the drawings. Such is to be taken in an illustrative and not necessarily limiting sense.

The joint of the invention is a load-bearing joint. The joint may be employed as a prosthesis or implant. Preferably, the joint includes an articulating surface component made of a suitable polyurethane (PU), and desirably, the component has a concave articulating surface. For example, the joint may be a hip replacement implant with the articulating surface component a polyurethane acetabular cup, or the joint may be a knee replacement implant with the articulating surface component a polyurethane tibial tray liner. Thus, in general, it is desirable to employ the polyurethane or its substitute component as a convex-part-receiving, articulating surface. See, FIG. 47.

Typically, in general, the articulating surface component is softer than the component with which it is mated. For example, a hip replacement head may be made of metal with the acetabular cup of the polyurethane; knee replacement condyles may be made of metal with the tibial tray liner of the polyurethane or its substitute. Generally, bone on plastic contact is undesirable.

Although frequent reference is made to polyurethane as comprising the joint of the invention, it is to be understood that a suitable substitute for the polyurethane may be made in the practice of the invention. For instance, as substitutes may be mentioned polyureas, polyurethaneureas and polyisocyanurates, and analogs thereof such as polythioureas and so forth. Halogenated polyurethane type compositions, especially fluorinated ones, may be employed in the present invention.

Accordingly, the polyurethane may be any polymer which consists of polyurethane molecule or which contains polyurethane segments chemically bonded to other type(s) of substance(s) to include polymer(s) or polyurethane portions melded physically to other type(s) of substance(s) to include polymer(s). The PU-substitutes are defined analogously. It is to be understood, however, that the polyurethane and its substitutes, when cured, must have the necessary physical properties to function adequately as a load-bearing joint. Thus, for example, over an extended time there should be no significant breaking up or disintigration of the same in use of the joint.

In general, in the practice of the invention, the polyurethane, polyurea, polyurethaneurea, polyisocyanurate or analog may comprise a reaction product of an isocyanate and an organic compound having at least two active hydrogen (AH) moieties, optionally with other component(s). For the purposes of this invention, an "active hydrogen moiety" refers to a chemical moiety which contains a hydrogen atom residue, which, because of its position in the molecule, displays significant activity according to the Zerewitnoff test. Ref., Kohler et al., *J. Am. Chem. Soc.,* 49, 3181–88 (1927). Polyurethanes are preferred and comprise a reaction product of an isocyanate and a polyol. Beneficial polyurethanes for employment in the practice of the invention include elastomeric polyurethanes. Accordingly, the polyurethane, as an illustrative example, may be formulated from a system such as that which follows:

In general, an A-side (isocyanate side) includes an isocyanate or the like compound, having a plurality of isocyanate moieties. Beneficially, the isocyanate compound is aliphatic, cycloaliphatic or aromatic. Some examples of isocyanate compounds include 1,6-hexamethylene diisocyanate; 4,4'-methylene bis(cyclohexyl isocyanate) (H12MDI); isophorene diisocyanate; 1,4-cyclohexyl diisocyanate (CHDI); toluene diisocyanate (TDI) (2,4- or mixture of 2,4- and 2,6-isomers); 4,4'-methylene bis(phenyl isocyanate) (PPDI) and other MDI-family members such as a mixture of 4,4'- and 2,4'-MDI or mixtures of 4,4'-, 2,4'- and 2,2'-MDI; para-phenylene diisocyanate; 1,5-naphthalene diisocyanate; substituted MDIs (CM3, OCM3, etc.) including poly(methylene)poly(phenylene) polyisocyanate (PMDI) and carbodiimide-modified MDI; MDI-containing quasi-prepolymers, polymeric MDI with NCO-functionality about 2.1–3.0; adducts of isocyanates to polyols including trimethylolpropene plus TDI:

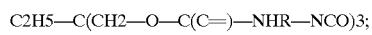

C2H5—C(CH2—O—C(C=)—NHR—NCO)3;

trimerization products of isocyanates:

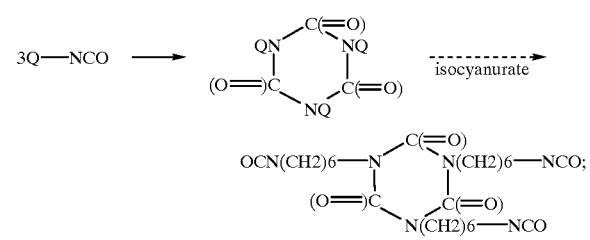

biuret adduct of 1,6-MDI (with R being C(=O)—O(CH2) 6-NCO):

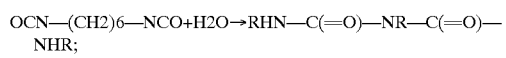

OCN—(CH2)6—NCO+H2O→RHN—C(=O)—NR—C(=O)—NHR;

and so forth and the like.

In general, a B-side (polyol side), which typically is to be mixed with the A-side to form the polyurethane employed in the present invention, includes a polyol. Although reference is made frequently herein to the polyol, which generally is employed to make polyurethanes of the joint of the invention, it is to be understood that a suitable substitute for or augmentation to the polyol may be made in the practice of the invention. For instance, as an alternative or augmentation, suitably stable amino and/or mercapto containing compounds may serve in the B-side with or without the polyol as the AH-moiety containing organic compound. In turn, the polyol or its substitute may be considered to be an oligomeric poly-AH organic compound. Beneficially, as an illustration, the polyol has a six-carbon or higher chain length, for example, for the polycarbonate polyols, and about a six hundred to three thousand, preferably about six hundred fifty to two thousand nine hundred, unit molecular weight. Desirably, the polyol is hydrolytically stable, and provides for good if not better mechanical properties in the final cured product. Examples of polyols include macropolyols such as of polyethers; polyesters; polyadipates; polysuccinates; products of glycols with dibasic acids such as adipic acid, succinic acid, and so forth; polycaprolactones:

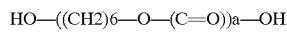

HO—((CH2)6—O—(C=O))a—OH polycarbonates and especially poly(carbonate) diols such as poly(1,6-hexanediol) carbonate:

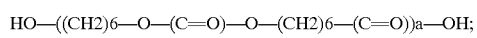

HO—((CH2)6—O—(C=O)—O—(CH2)6—(C=O))a—OH;

poly(1,4-cyclohexanediol) carbonate:

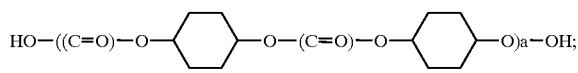

poly(1,4-butanediol) carbonate; acrylic based glycols/polyols; epoxy-based glycols/polyols; poly(oxyalkylene) glycols and polyols including those such as poly(oxytetramethylene) glycols (polytetramethylene ether glycols or poly-THF):

poly(oxyethylene) glycols and polyols:

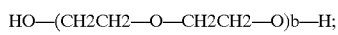

poly(oxypropylene) glycols and polyols:

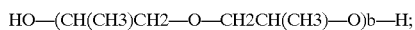

glycerol; trimethylolpropane; penteretythritol; sorbitol; sucrose; adducts of propylene oxide; adducts of propylene and ethylene oxides; and/or other aliphatic, cycloaliphatic or aromatic hydrocarbon-based polyol. In the foregoing general formulae, "a" is about four or greater, preferably about six or greater; and "b" is about four to a hundred or so. As an example of another subgenera of AH-moiety-containing compounds which may be employed in the B-side are hindered terminal amino polymethylenes such as of the general formula:

wherein "c" is about from two or twenty to four hundred or five hundred, and "R" is a sterically hindering group, e.g., t-butyl. A mixture of polyols and/or other AH-moiety-containing compounds may be employed. For instance, polyurethane elastoplastics may be prepared based on the poly(carbonate) diols, combinations of poly(oxytetramethylene) glycols and/or fluorinated diols, which can have good saline resistance, and machined, for example, to acetabular cups, tibial tray liners, and so forth, in the practice of the present invention. One or more chain extender(s) may be, and desirably is(are), present in the B-side. The chain extender can be a monomeric di-AH-moiety-containing compound or mixture thereof. The AH-moiety chain extender compounds may include compounds with primary and/or secondary amino, hydroxyl and/or mercapto moieties. Beneficially, the AH-moiety is hydrolytically stable. Short chain diols, generally of from three to twelve or so carbons per carbon chain, including primary and/or secondary amines, alkanolamines, and thiols are possible chain extenders. Examples of chain extenders may include 1,3-propanediol, 1,4-butanediol, 1,6-hexanediol, dimethylcyclohexyldiol, 1,4-bis-hydroxydiethyl hydroquinone (HQEE), ethylenediamine, 1,2-propanediamine (racemic or enantiomerically enriched/pure), 1,3-propanediamine, 1,4-propanediamine, 1,6-propanediamine, piperazine, 2-methylpiperazine, ethanolamine, diethanolamine, 1,2-ethanedithiol, and so forth and the like. In general, whereas the macropolyol or the like provides for soft segments, the presence of the chain extender provides for hard segments in the final product. In other words, elastomeric portions help overcome brittleness. Cross-linking (thermosetting) compositions may be provided as by addition of the 1,1,1-trimethylolpropane compound in a suitable amount to obtain a slightly cross-linked elastomeric polyurethane. Accordingly, the polyurethane base product, which is to be machined to produce the final joint or joint component of the present invention, may be slightly cross-linked, which may provide for favorable compression properties, or it may be thermoplastic. In addition, a catalyst may be present in the B-side if needed or desired. For instance, the catalyst may be a Lewis acid type catalyst. In general, the catalyst can include a metal or organometallic catalyst such as a tin-containing catalyst such as stannous octoate, dibutyltin dilaurate, diethyltin dilaurate, and so forth and the like. An antioxidant, for example, a hindered phenol such as O-tert-butylphenol, and so forth and the like, may be employed in the practice of the present invention as well.

Prepolymer mixtures may be employed. For instance, a prepolymer mixture which is commercially available may be advantageously employed in the practice of the invention.

In general, stoichiometry of the A-side/B-side contact is that sufficient for the desired product. So as to avoid foaming, reactants, especially those containing the AH-moieties and/or otherwise hygroscopic, may be dried before contact, for example, by dry heating under vacuum.

Preferably, no fillers nor dyes are present.

Any suitable method of contact, reaction and curing of the so-called A-side and B-side components may be employed. For instance, the one-shot, quasi-prepolymer or prepolymer method may be employed, as well as may be reaction injection molding, extrusion, compression molding, and so forth. These are well known to any person skilled in the art. Processing curing may be carried out in a mold at any suitable temperature, say at from sixty to one hundred fifty degrees C for one hour or so, with post processing curing at a temperature from about one hundred to one hundred fifty degrees C for five to a hundred, say, sixteen to seventy-two, hours or so.

The components are selected to assure good dynamic mechanical properties, flex-fatigue resistance, abrasion resistance, and, as well, biocompatibility. The polyurethane, or other analogous plastic, produced may be considered to be elastomeric. The PU also may be considered to be thermoplastic, and as such it may be termed a "TPU." Slightly cross-linking of the polyurethane again may provide for favorable compression properties, and so forth. The joint can exhibit excellent hardness and stress strain properties which equal or exceed those of UHMWPE.

The polyurethane type material may be machined after reaction processing and/or curing to provide the joint or joint component. In general, it cuts or machines well.

The following examples further illustrate the invention. Therein, in general, parts and percentages are set forth by weight unless otherwise specified or ascertained by the surrounding context as would be understood in the art.

EXAMPLE SET 1

I. EXPERIMENTAL

A. Chemicals:

Chemicals employed are listed in Table 1. Polyols and chain extenders were dried under a vacuum of 1–3 mmHg at seventy degrees Celsius overnight prior to employment. The isocyanates were employed as received from the suppliers, and the isocyanate content was determined by the well known di-n-butylamine method.

TABLE 1

Materials

| Designation | Chemical Identification | Eq. Wt. | Supplier |
|---|---|---|---|
| PTMO 650 | Poly(oxytetramethylene) glycol | 335.5 | DuPont |
| PTMO 1000 | Poly(oxytetramethylene) glycol | 494.5 | DuPont |
| Adiprene LFP X950A | Reaction product of polyether polyol with PPDI ($C_{NCO}$ = 5.46 ≈ 5.52%) | | Uniroyal Chemical |
| 1,4-BD | 1,4-Butanediol | 45 | GAF Corporation |
| MDI (Mondur M) | 4,4'-Diphenylmethane diisocyanate | 125 | Bayer AG |
| $H_{12}$ MDI (Desmodur W) | Methylene bis(4-cyclohexyl isocyanate) | 131 | Bayer Co. |
| PPDI | Para-phenylene diisocyanate | | DuPont |
| T-12 | Dibutyltin dilaurate | | Air Products |
| Irganox 565 | Antioxidant | | Ciba Geigy Corporation |

Preparation of TPU Elastomers

Prepolymer Method

Several types of NCO-prepolymers were prepared starting from aromatic (MDI and PPDI) and cycloaliphatic ($H_{12}$MDI) isocyanates. In addition, elastoplastics were prepared by using commercial PPDI-prepolymer Adiprene LFP X950A (NCO %=5.46).

The procedure for the prepolymer preparation depends somewhat on the type of isocyanate used in the prepolymer preparation. The NCO-terminated prepolymer based on PPDI and PTMO 650 (or PTMO 1000) was prepared as follows: PPDI (flaked) was placed in a 1-L glass reaction kettle which was equipped with a stirrer under a continuous flow of nitrogen. PTMO 650 was heated at 60° C. and added under mixing to the PPDI. The reaction exotherm temperature started to rise close to 90° C. which was maintained for about 50 minutes. The theoretical NCO % was reached at about the same time. Afterwards the temperature of the prepolymer started to decrease. The prepolymer is a liquid at 60° C. but is a solid at room temperature.

In the second step, a specified amount of the prepolymer and free isocyanate were mixed and heated to 110° C. to homogenize. The mixture was transferred to the reactor and degassed for two hours under vacuum at 80° C. Afterwards, the temperature was decreased to 60° C., 1,4-BD (previously degassed) was added and the reaction mixture shortly degassed before transferring to the mold. The mold covered with Teflon sheets was placed into a Carver press which was preheated to 125° C. When gelation occurred (as determined by string formation), the mold was compressed at ~20,000 psi at 125° C. for one hour. Finally, the mold was placed in an oven at 125° C. for 24 hours for postcuring.

The NCO-terminated prepolymer based on MDI and PTMO 650 at an NCO/OH equivalent ratio of 2/1 were prepared by using the following procedure: MDI (previously melted at 70° C.) was place in a 1 L glass reaction kettle which was equipped with a stirrer under a continuous flow of nitrogen. The reactor was heated utilizing a heating mantle. When the temperature of the isocyanate reached 60° C., PTMO 650 was slowly added into the reactor. Since the reaction of PTMO with MDI was very fast and very exothermic, in order to maintain the temperature at 65–75° C., the speed of addition of the polyol was important. When the exothermic reaction decreased, the temperature was maintained at ~70° C. Periodic samples were withdrawn during the reaction to determine the —NCO concentration. After the theoretical NCO % value was reached, the reaction was stopped by cooling and the prepolymer was stored in a sealed glass bottle under nitrogen. In the second step, a specified amount of the prepolymer (preheated at 80–90° C.) was weighed into a 250 ml plastic cup. The chain extender or chain extender/T-12 mixture (preheated at 80–90° C.) was added to the prepolymer. All the components were then mixed vigorously for ~30 seconds. The mixture was then poured into a mold covered with Teflon sheets and placed into a Carver press. When gelation occurred, the mold was compressed at 20,000 psi at 105° C. for 1 hour. Finally, the mold was placed in an oven at 105° C. for 24 hours for postcuring.

The NCO-prepolymer based on H12MDI and respective elastomers were prepared by using the procedure similar to MDI elastomers. The specific curing conditions are specified in Table 7.

Preparation of TPUs by the One Shot Method

The polyol, chain extender and catalyst T-12(if added), preheated at 100° C., were weighed in a 250-ml plastic cup and mixed using a high speed laboratory mixer for one minute. Isocyanate (H12MDI or MDI) was added to the mixture; MDI was previously melted at 70° C. All the components were then mixed vigorously and then transferred to the mold. The MDI-based resin system was very reactive (gel time was 20–30 seconds) and hence, the mixing time was only a few seconds. The H12MDI polyurethane system was less reactive exhibiting a longer gel time. At the gel time, the resin system was compression molded at 20,000 psi in a Carver press at 105° C. for 1 hour and then the polyurethane sheet was post-cured in an oven at 105° C. (if different it is specified in the corresponding tables).

Figure 1:
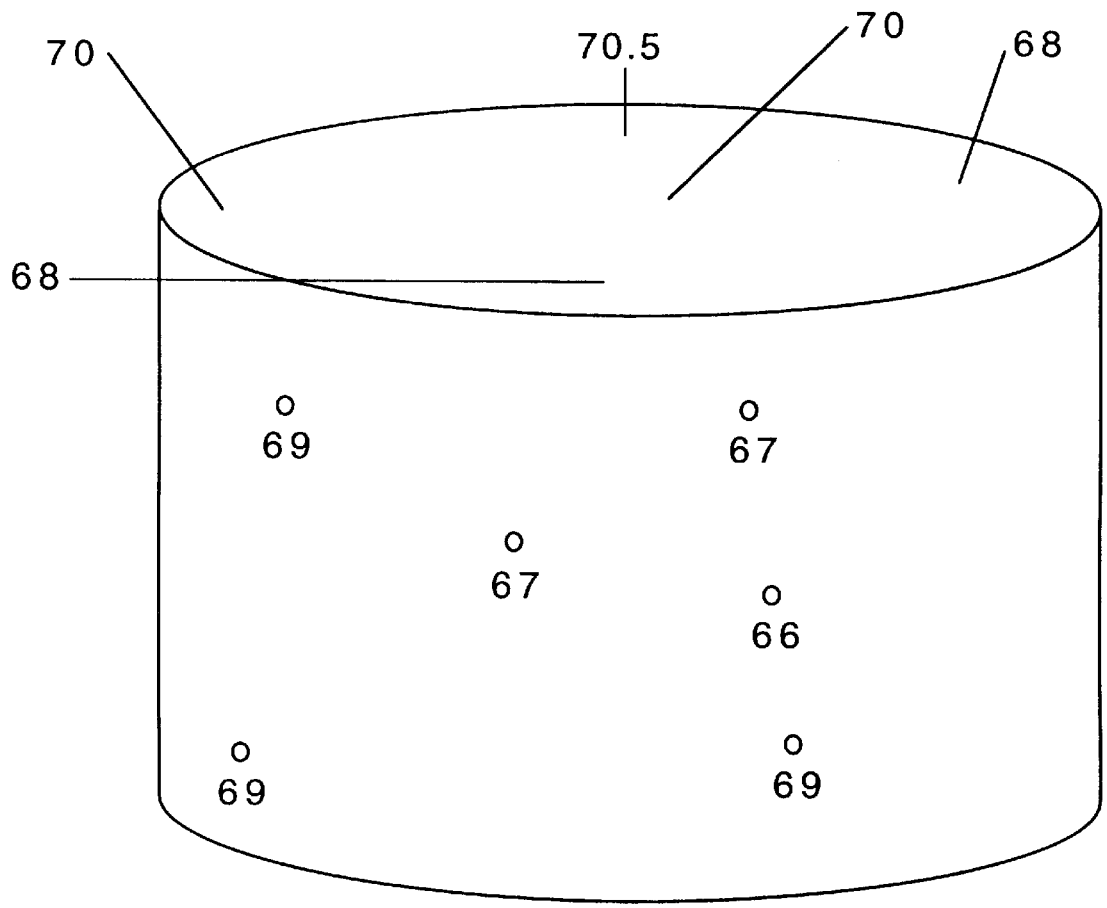
FIG. 1 is a perspective view of a polyurethane elastomer cylinder for making joint components of the invention, the same illustrating hardness values therein.

Molded cylindrical polyurethane samples were prepared by using the resin system based on Adiprene LFP X950 A/MDI/1,4-BD at 65% hard segment concentration. The degassed resin system was poured into a metallic cylindrical mold with an internal cavity of diameter=1.3 inches and height=1.6 inches, compressed in a Carver press and cured at 125° C. for 24 hours. A drawing of the molded electroplastic sample with the hardness (Shore D) measured at different spots on the same surface is shown in FIG. 1.

The UHMW-PE samples were prepared by remelting a cylindrical slice of UHMWE-PE in a carver press at 200° C.

Evaluation of the Properties of Elastoplastics

The following properties of polyurethane elastoplastics and UHMW-PE were tested:

Hardness, Shore D(ASTM D-2240-75)

Stress-strain properties, RT and 40° C. (ASTM D-412-68)

Flexural modulus (ASTM D-790)

Abrasion resistance(Taber Abrader)

Izod impact (ASTM D-256)

The glass transition temperature was measured by using the dynamic mechanical analysis (DMA) and softening by using thermo-mechanical analysis.

The resistance in saline solution was measured by immersing the elastoplastics in a saline solution and measuring the weight change periodically.

II. RESULTS AND DISCUSSION

MDI-Based Polyurethane Elastoplastics

MDI-polyurethane elastoplastics were prepared by using a one shot and the prepolymer method at the hard segment concentrations of 65 and 70% (Tables 2 and 3). Poly (oxytetramethylene)glycols. PTMO 650 and PTMO 1000 were utilized as a flexible segments and 1,4-BD as a chain extender. The properties of elastoplastics prepared by the one shot and prepolymer method at 65% hard segment concentration were similar. The molecular weight of the flexible segment (PTMO 650 versus PTMO 1000) also effected the properties of elastoplastics (Table 3); a tougher material was obtained with PTMO 650. Based on this screening study, MDI-elastoplastics with PTMO 650 flexible segment at 65% hard segment concentration, prepared by using the one shot method at 65% hard segment concentration exhibited the best combination of properties.

The properties of MDI/PTMO650/1,4-BD elastomers along with UHMW-PE are shown in Table 4. The abrasion resistance (abrading wheels H-22, the wheel loading 500 g, 4000 cycles) measured under quite severe conditions was found to be very low for UHMW-PE (1.5%) and about 10% for aromatic isocyanate PU elastomers. However, there is a question whether the abrasion resistance is this test relates to smear problems in joint application since the contact surfaces are smooth. The tensile strength of PU elastoplastics at the same hardness was similar to that of UHMW-PE, but the elongation at break of PU elastoplastics was higher by 20% and more. The tensile strength and elongation at break of PU elastoplastics changed slightly with temperature, as expected. The room temperature hardness of elastoplastics decreased slightly when measured at 40° C. (Tables 5 and 6). In contrast, the elongation at break of UHMW-PE decreased from 409% at RT to 211% at 40° C., indicating a significant change in the material. The toughness (area under the stress-strain curve) was somewhat higher for MDI and MDI/PPDI elastoplastics at both RT and 40° C. than that of UHMW-PE (Tables 4 and 6). The Young's modulos of UHMW-PE was high 74610 psi, higher than that of aromatic elastoplastics. However, it should be taken into consideration that this type of polyethylene is filled with calcium carbonate. The notched impact resistance (Izod impact) of elastoplastics was measured by using a load up to 200 pounds. None of the samples, containing aromatic and cycloaliphatic isocyanates were broken, indicating very good impact resistance properties.

Figure 2:
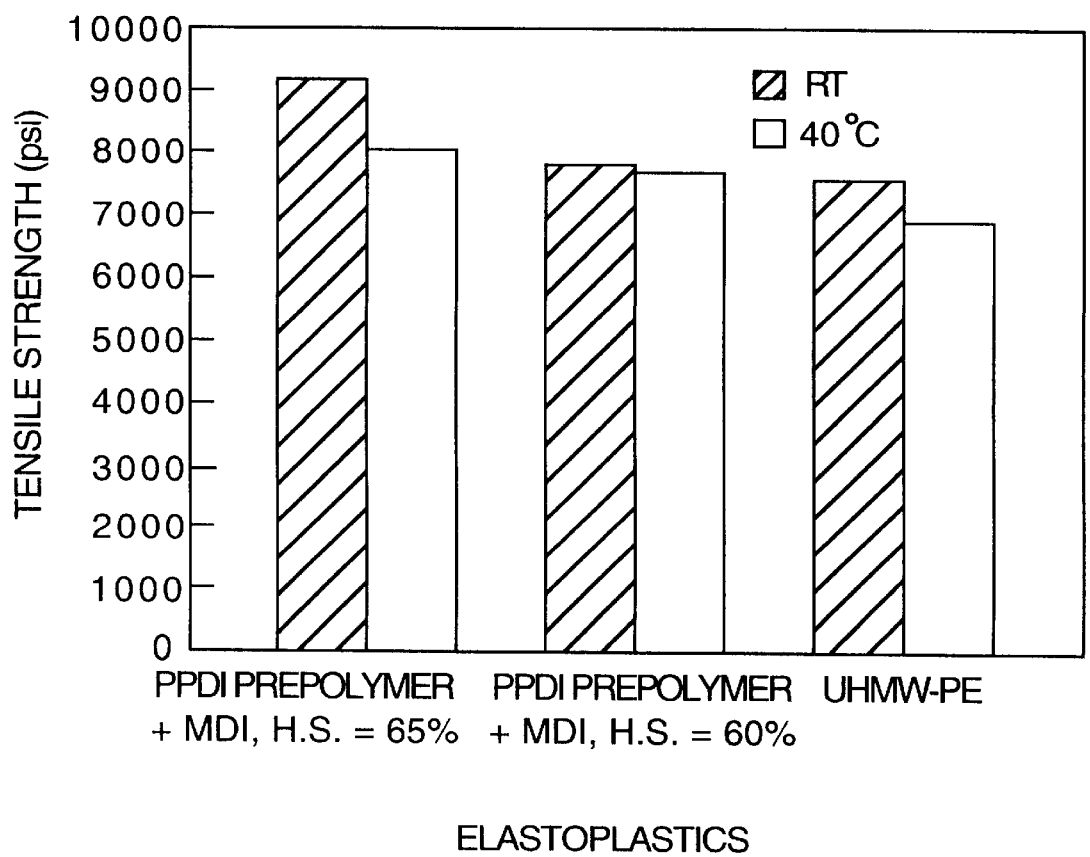
FIG. 2 is a bar graph of the effect of temperature on ultimate tensile strength of polyurethane elastoplastics of and/or employed in the invention, with UHMW-PE control.
Figure 3:
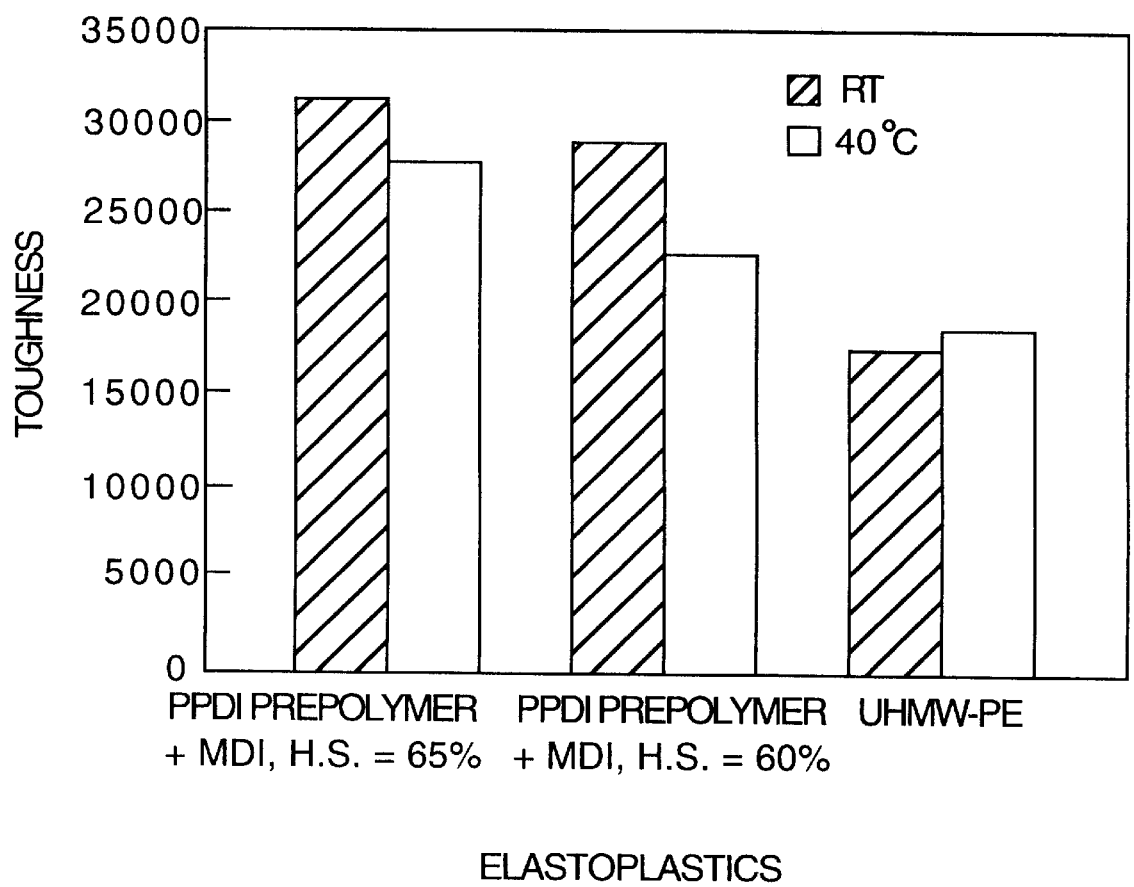
FIG. 3 is a bar graph of the effect of temperature on toughness of polyurethane elastoplastics of and/or employed in the invention, with UHMW-PE control.
Figure 4:
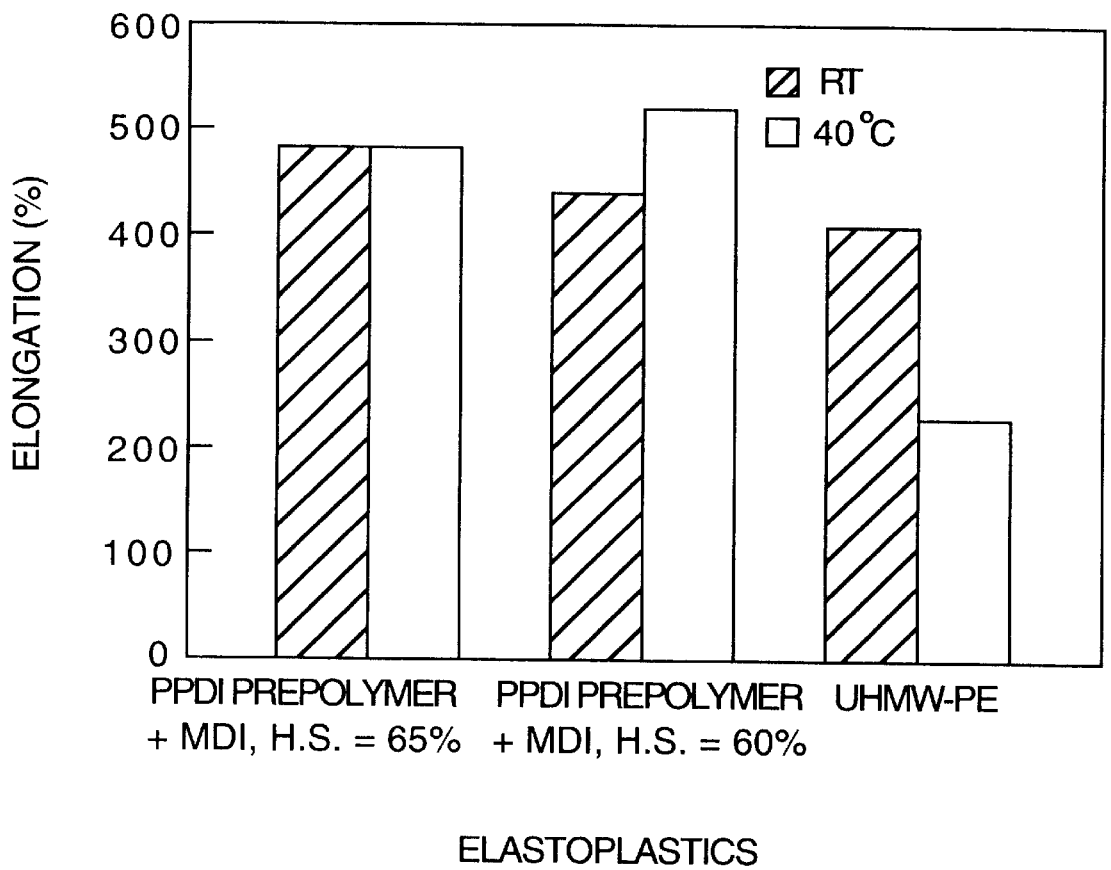
FIG. 4 is a bar graph of the effect of temperature on elongation at break of polyurethane elastoplastics of and/or employed in the invention, with UHMW-PE control.

Aromatic isocyanate elastoplastics were also prepared from a commercial prepolymer, Adiprene LFP X950, MDI and 1,4-BD at a hard segment concentration of 60 and 65% (Table 5). Adiprene LFP X950A is a commercial prepolymer presumably made from PPDI and and PTMO 1000. The hardness of these elastoplastics was 67 and 68 Shore D, similar to the hardness of UHMW-PE. These materials exhibited very good physico-mechanical properties; e.g. the tensile strength of elastoplastic prepared at 60% hard segment concentration was 7171 psi at relatively high elongation at break 565%. The elongation at break increased only slightly be heating to 40° C. (645%), while with UHMW-PE it decreased from 409 to 211%. The Taber abrasion resistance of PPDI/MDI elastoplastics was similar to that of MDI-elastoplastics. The preparation of the PPDI-based elastoplastics has been extended by using the prepolymer of PPDI and PTMO 650 (NCO% 9.42) prepared in our laboratory. The formulation and properties of elastoplastics based on PPDI/PTMO 650 are shown in Table 6. Two elastoplastic samples were prepared by reacting PPDI/PTMO650 prepolymer and free MDI with 1,4-BD at two hard segment concentrations, 60 and 65%. The tensile strength, Young's modulus and toughness significantly improved by increasing the hard segment concentrations from 60 to 65%. The last sample exhibited outstanding properties. The tensile strength was 9339 psi and the elongation at break was still very good, 484%. The toughess, which is the area under the stress-strain curve was 31642 psi at RT as compared to 18170 psi found for the UHMW-PE. It is expected that higher toughness should correlate with higher shear and compressive modulus which are some of the forces encountered in joints. The properties of PPDI/PTMO650 elastoplastic change little by heating from RT to 40° C. (FIGS. 2–4). The molecular weight of the flexible segment of the PPDI-prepolymer affected significantly the properties of elastoplastics which were prepared at the same hard segment concentration. The tensile strength, Young's modulus, yield strength and toughness were all higher when prepared with PTMO 650 as compared to PTMO 1000 (Table 5 and 6), similarly as with MDI-elastoplastics. The elastoplastic prepared from PPDI/PTMO650 and free PPDI at 50% hard segment concentration exhibited similar hardness but lower stress-strain properties as compared to the samples prepared from the same prepolymer and free MDI.

H12MDI-Based Elastoplastics

The formulations, curing conditions and properties of H2MDI-based elastoplastics are shown in Table 7. The effects of the curing conditions (temperature and time) on the properties of elastoplastics were studied. The best properties were obtained when the materials were cured (1 hour) and postcured at 110° C.(24 hours). These elastoplastics were prepared at 70% hard segment concentration, resulting in a hardness range of 69–73 Shore D. The abrasion resistance (as measured by Taber abrader) of H12MDI elastoplastics was somewhat better than that of MDI and MDI/PPDI elastoplastics, as expected. The tensile strength at RT was very good, similar to HPVM-PE material; however it changed more by heating to 40° C. than the aromatic isocyanate PU and UHMW-PE (18170 psi). The toughness of H12MDI-elastoplastics decreased significantly from 19904 to 13681 psi when the temperature increased from RT to 40° C. The toughness of aromatic isocyanate elastoplastics was significantly higher and could be attributed to their symmetric structure, while H12MDI is a mixture of genometric isomers. The Young's modulus of H12MDI-elastoplastics at RT was excellent; however it decreased sharply at 40° C.

The flexural modulus of two elastoplastic samples based on H12MDI, prepared at two isocyanate indices was measured at RT and the following values were obtained: 89660 psi (at isocyanate index 102) and 72620 psi(at isocyanate index 100). The flexural modulus of MDI/PTMO65O/1,4-BD elastoplastics was 54680 psi and 53310 psi for UHMW-PE.

Resistance in Saline Solution

Figure 5:
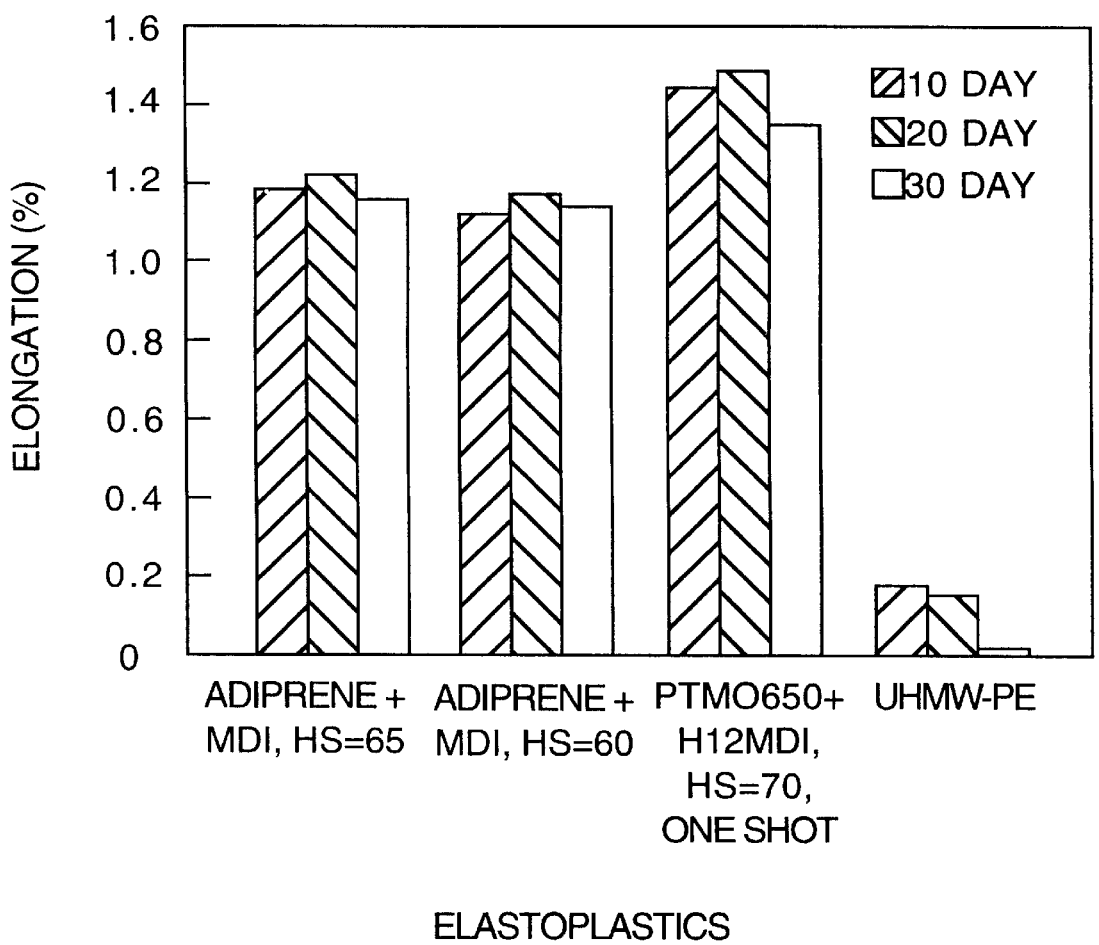
FIG. 5 is a bar graph of the effect of saline immersion at forty degrees Celsius on weight change of polyurethane elastoplastics of and/or employed in the invention, with UHMW-PE control.
Figure 6:
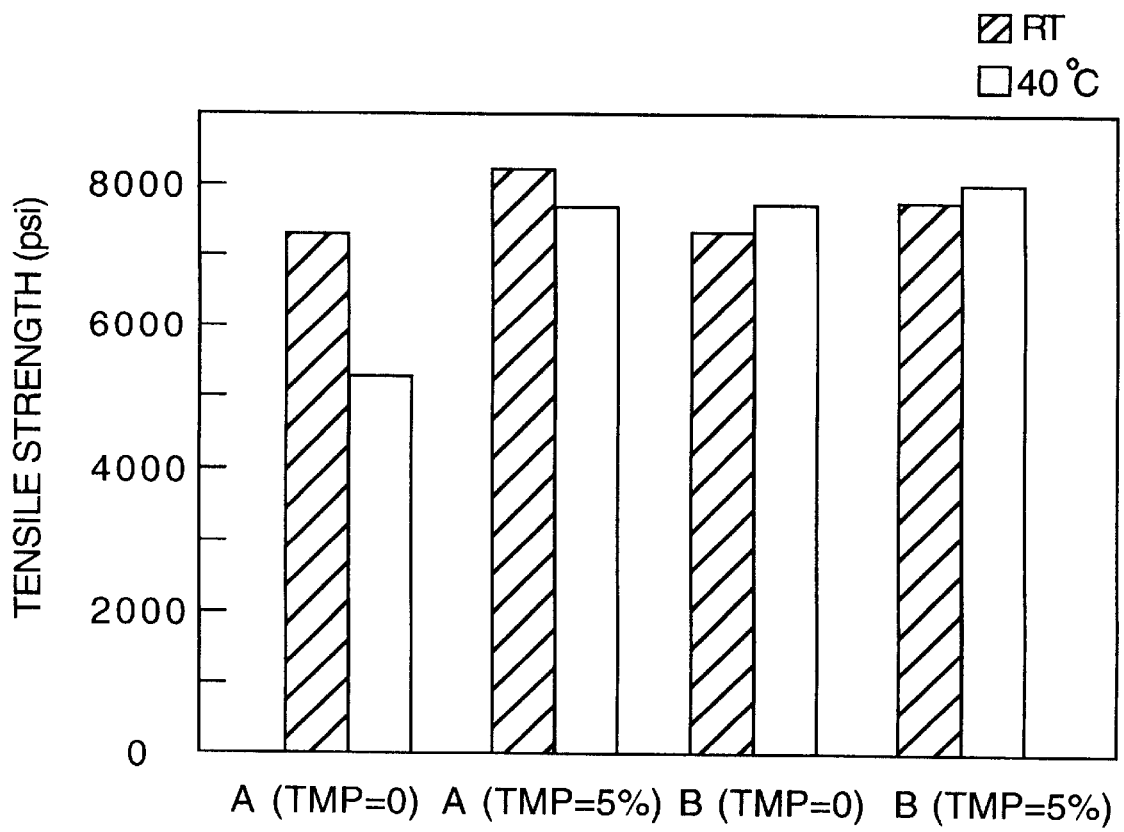
FIG. 6 is a bar graph of the tensile strength of polyurethane elastoplastics of and/or employed in the invention.
Figure 7:
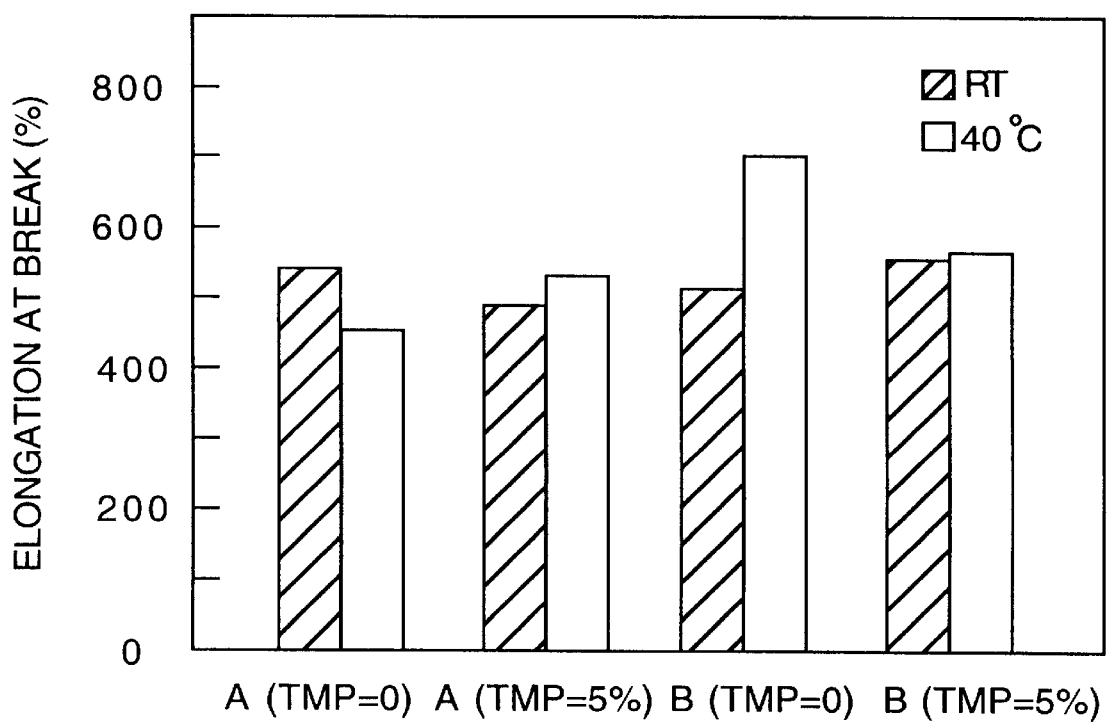
FIG. 7 is a bar graph of the elongation of polyurethane elastoplastics of and/or employed in the invention.
Figure 8:
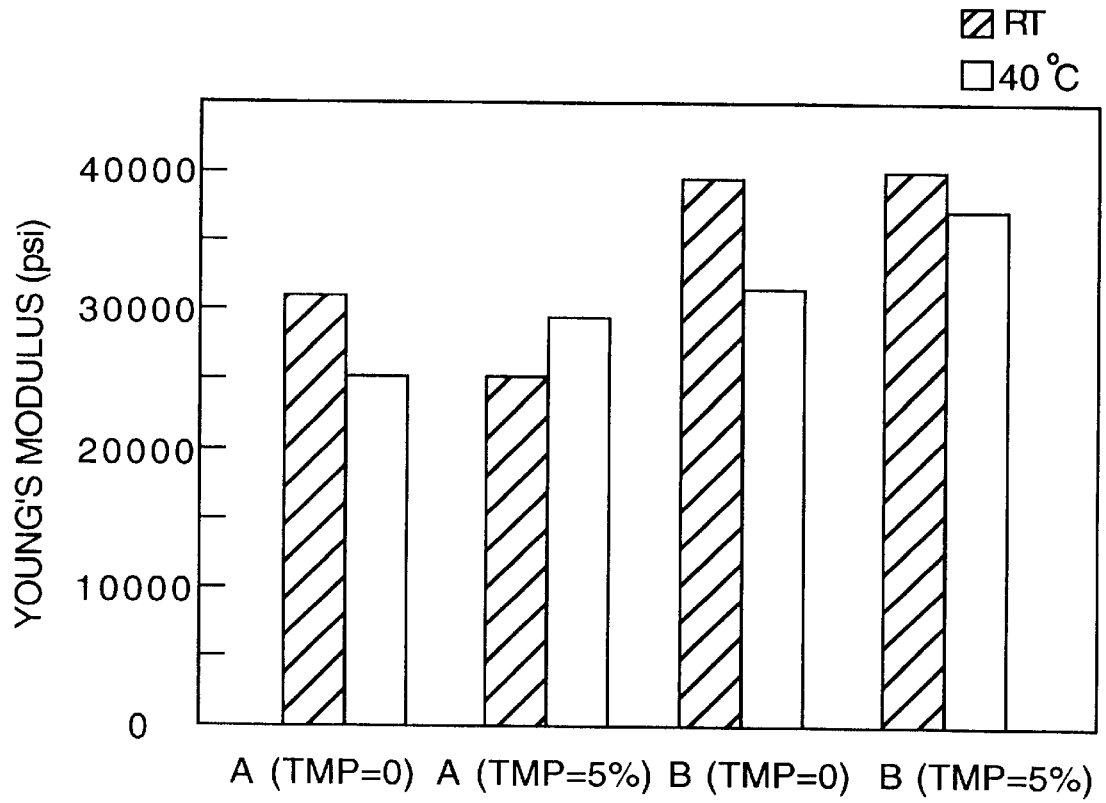
FIG. 8 is a bar graph of Young's Modulus of polyurethane elastoplastics of and/or employed in the invention.
Figure 9:
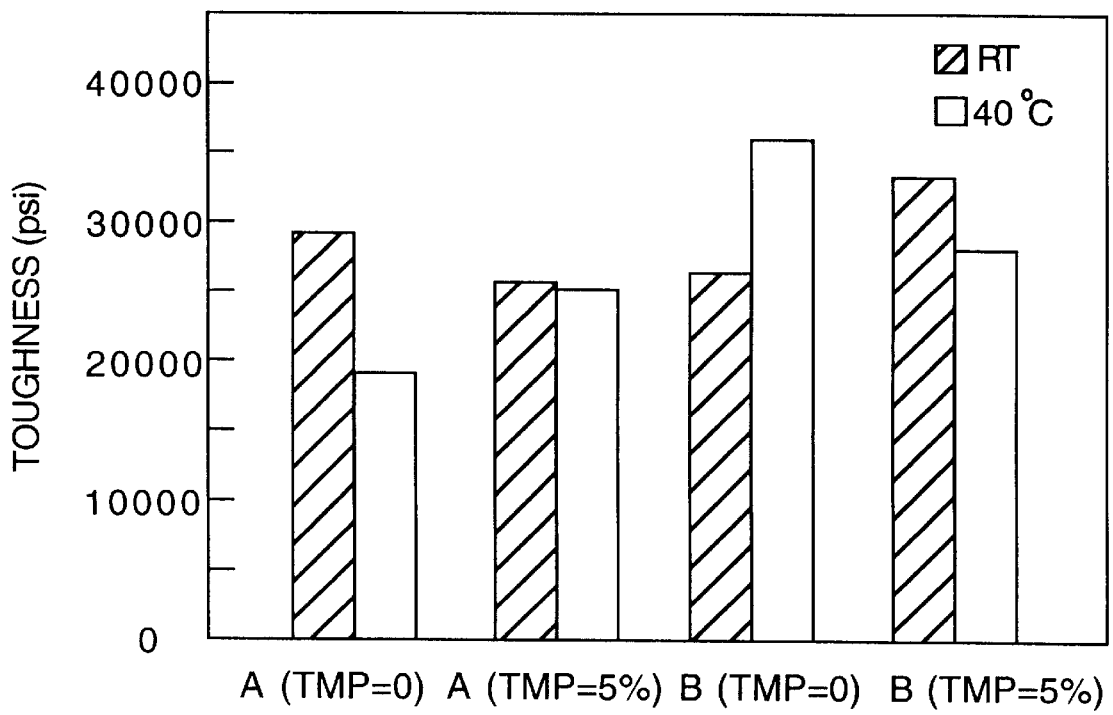
FIG. 9 is a bar graph of the toughness of polyurethane elastoplastics of and/or employed in the invention.
Figure 10:
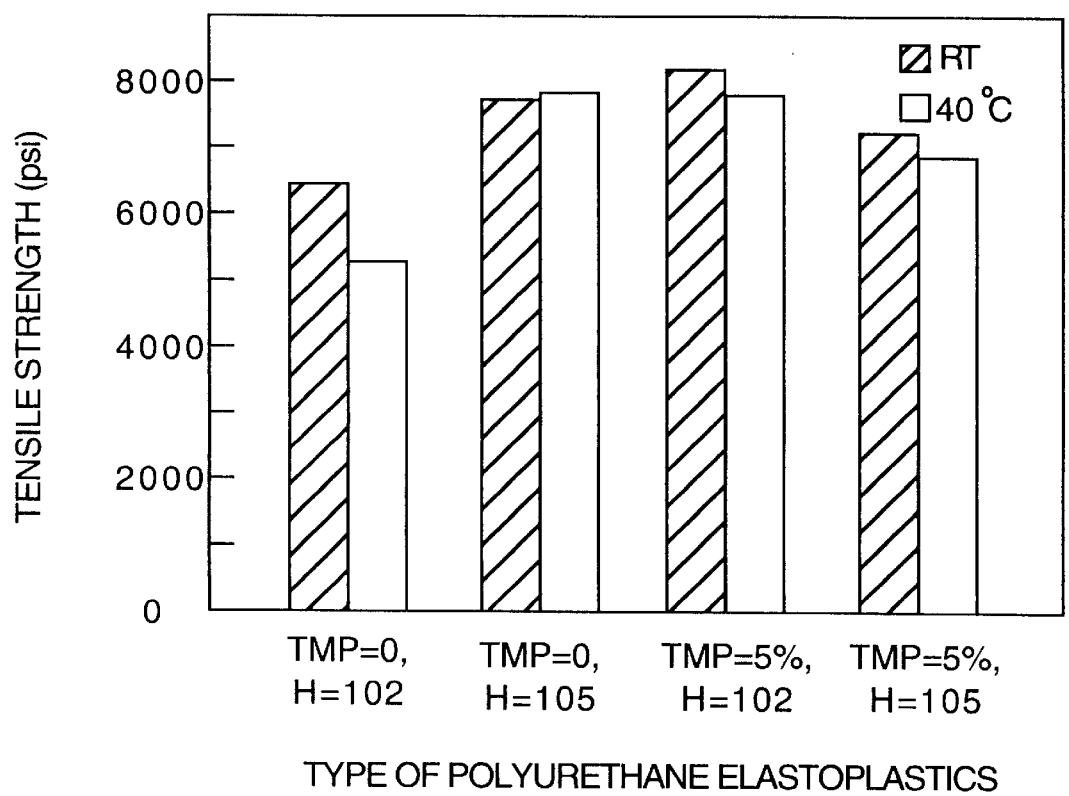
FIG. 10 is a bar graph of the tensile strength of polyurethane elastoplastics based on a PPDI prepolymer mixture of fifty weight percent PTMO-650 and fifty weight percent PTMO-1000 of and/or employed in the invention.
Figure 11:
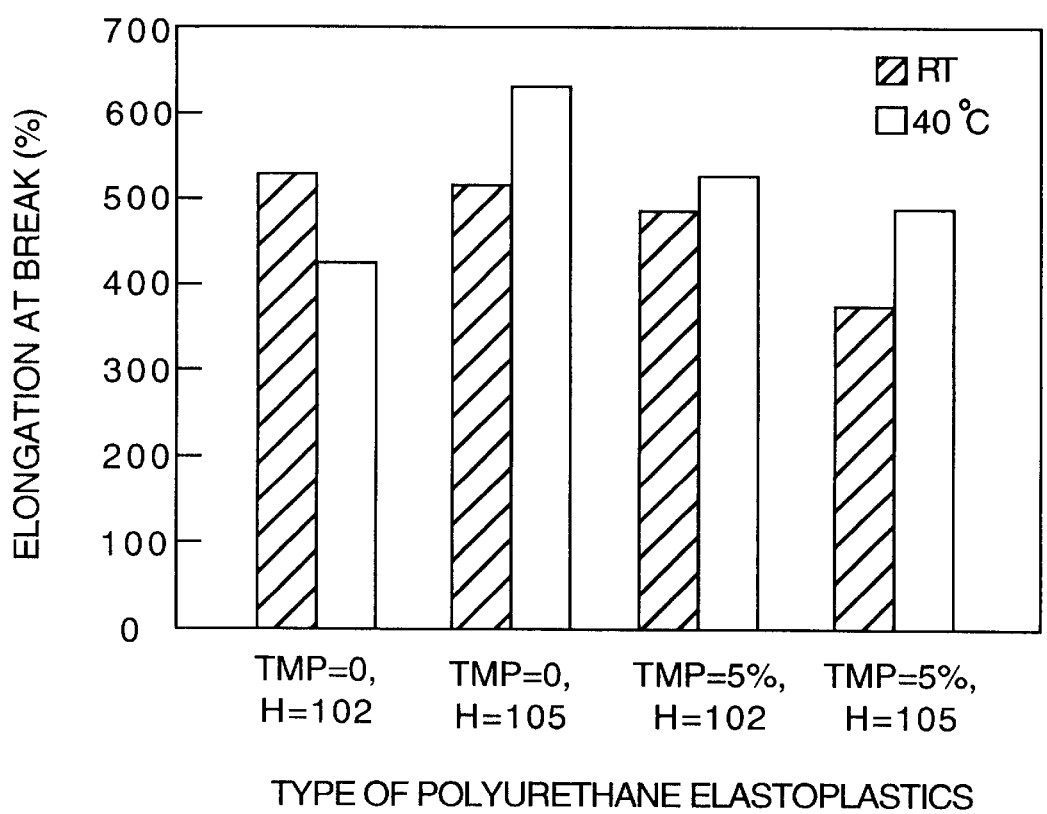
FIG. 11 is a bar graph of the elongation of polyurethane elastoplastics based on a PPDI prepolymer mixture of fifty weight percent PTMO-650 and fifty weight percent PTMO-1000 of and/or employed in the invention.
Figure 12:
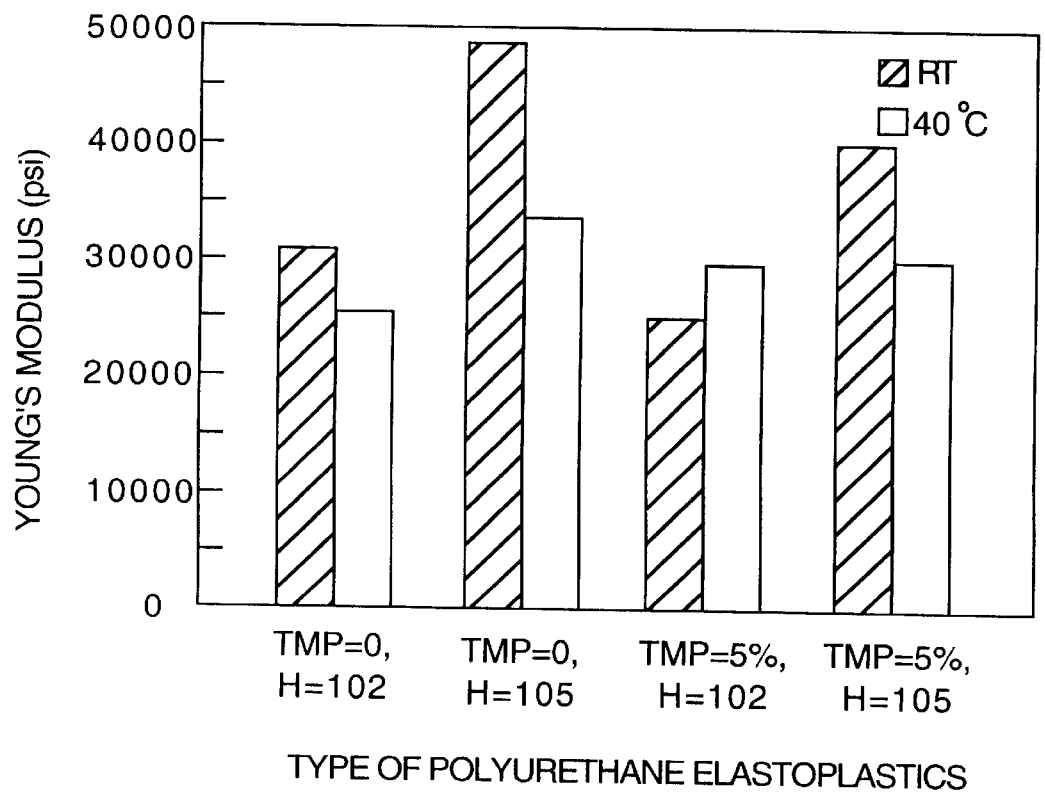
FIG. 12 is a bar graph of Young's Modulus of polyurethane elastoplastics based on a PPDI prepolymer mixture of fifty weight percent PTMO-650 and fifty weight percent PTMO-1000 of and/or employed in the invention.
Figure 13:
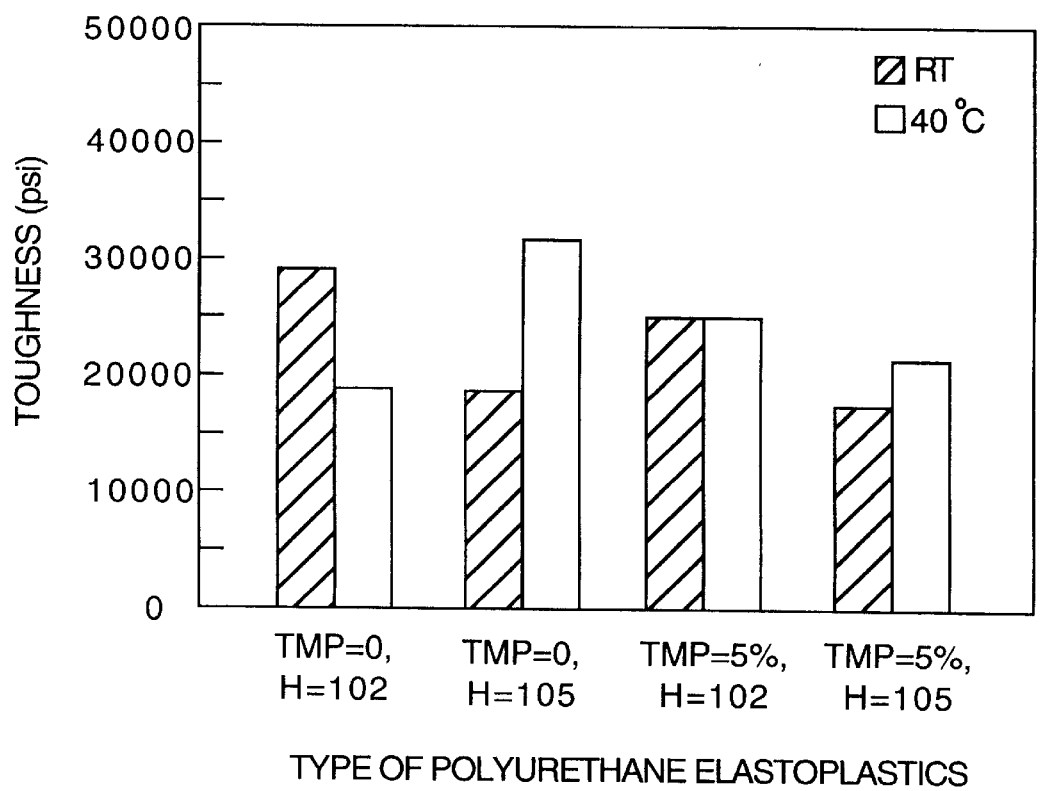
FIG. 13 is a bar graph of the toughness of polyurethane elastoplastics based on a PPDI prepolymer mixture of fifty weight percent PTMO-650 and fifty weight percent PTMO-1000 of and/or employed in the invention.
Figure 14:
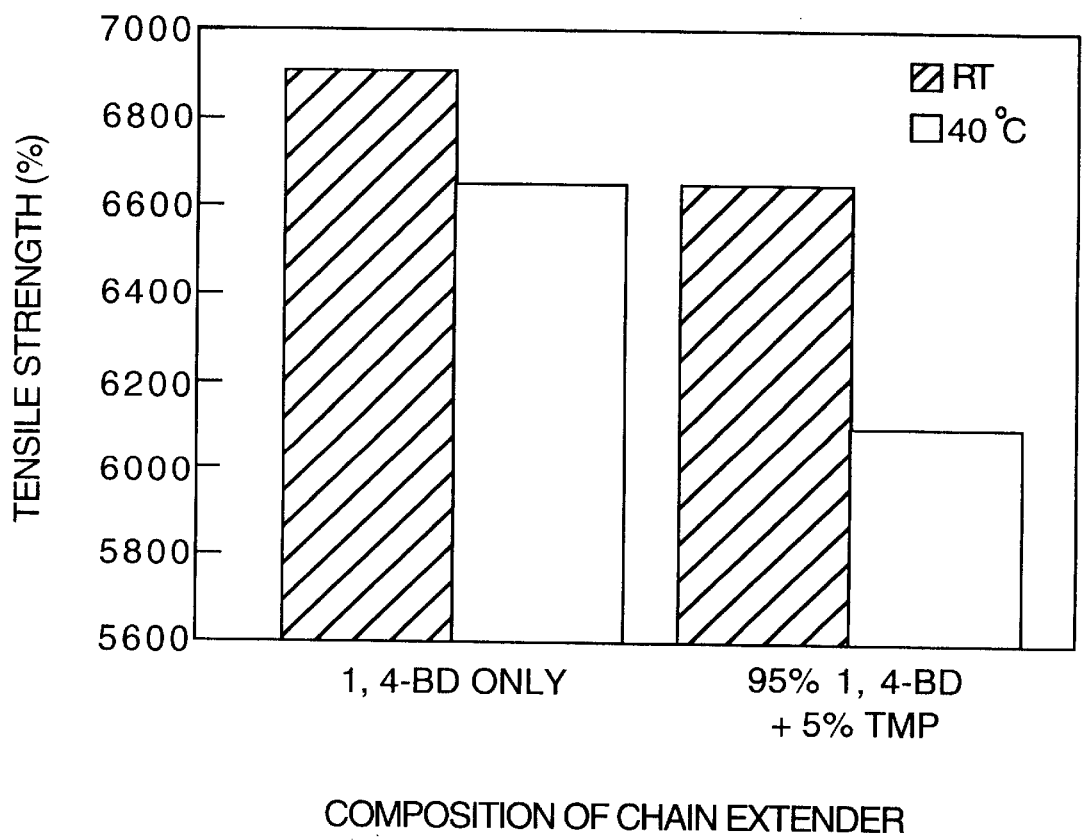
FIG. 14 is a bar graph of the effect of composition of chain extender on the tensile strength of a polyurethane elastoplastics based mixture of 1,4-BD+TMP, and Adiprene LFP X950A of and/or employed in the invention.
Figure 15:
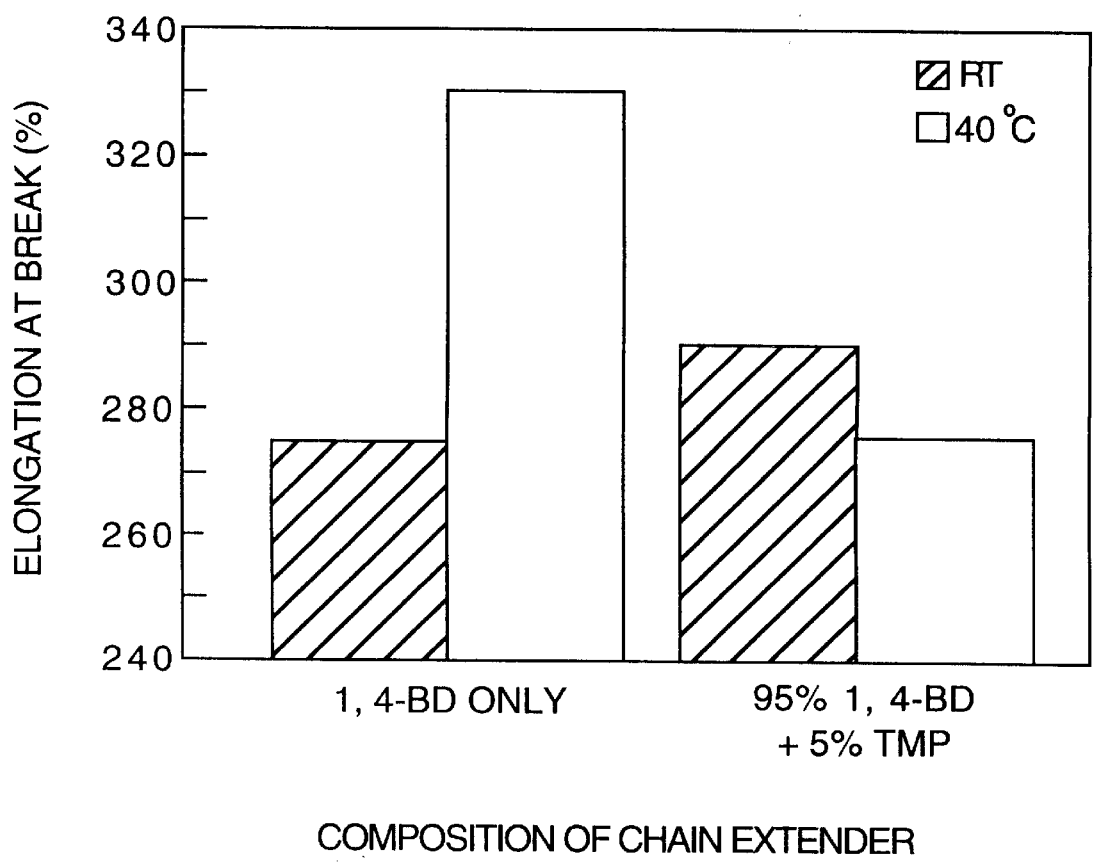
FIG. 15 is a bar graph of the effect of composition of chain extender on the elongation of a polyurethane elastoplastics based mixture of 1,4-BD+TMP, and Adiprene LFP X950A of and/or employed in the invention.
Figure 16:
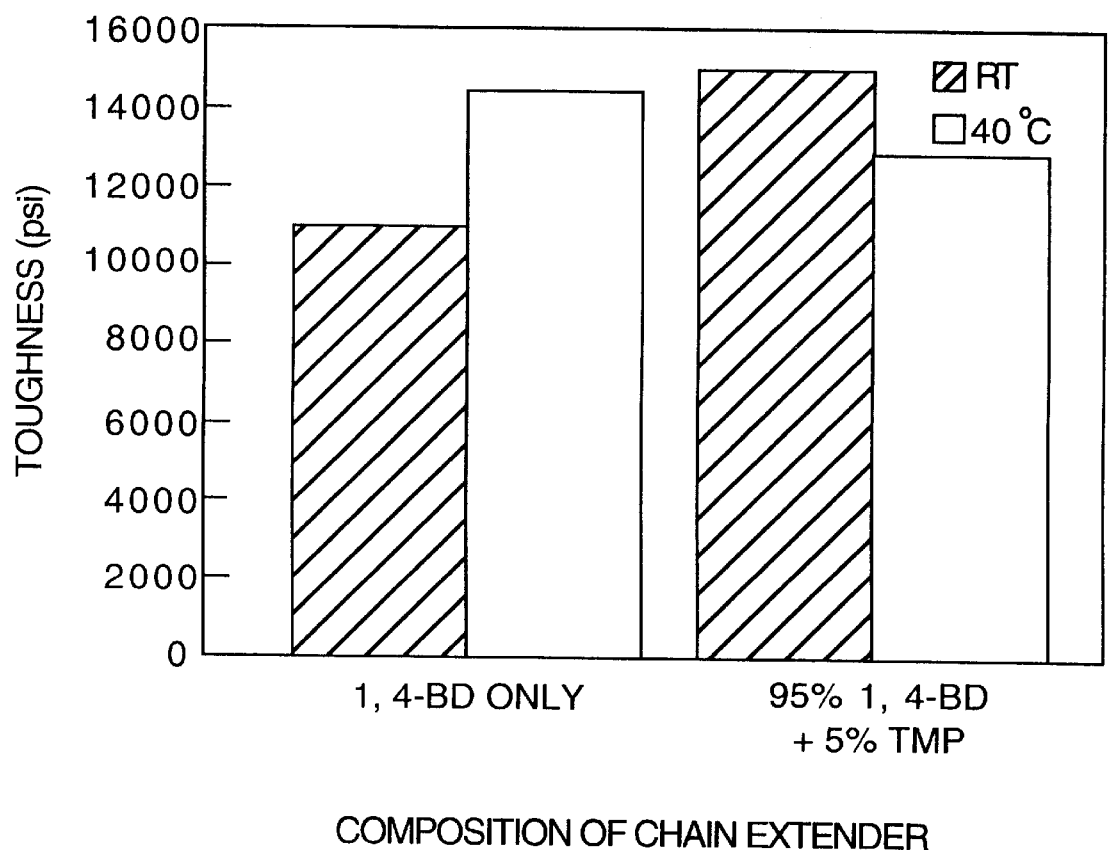
FIG. 16 is a bar graph of the effect of composition of chain extender of the Young's Modulus of a polyurethane elastoplastics based mixture of 1,4-BD+TMP, and Adiprene LFP X950A of and/or employed in the invention.
Figure 17:
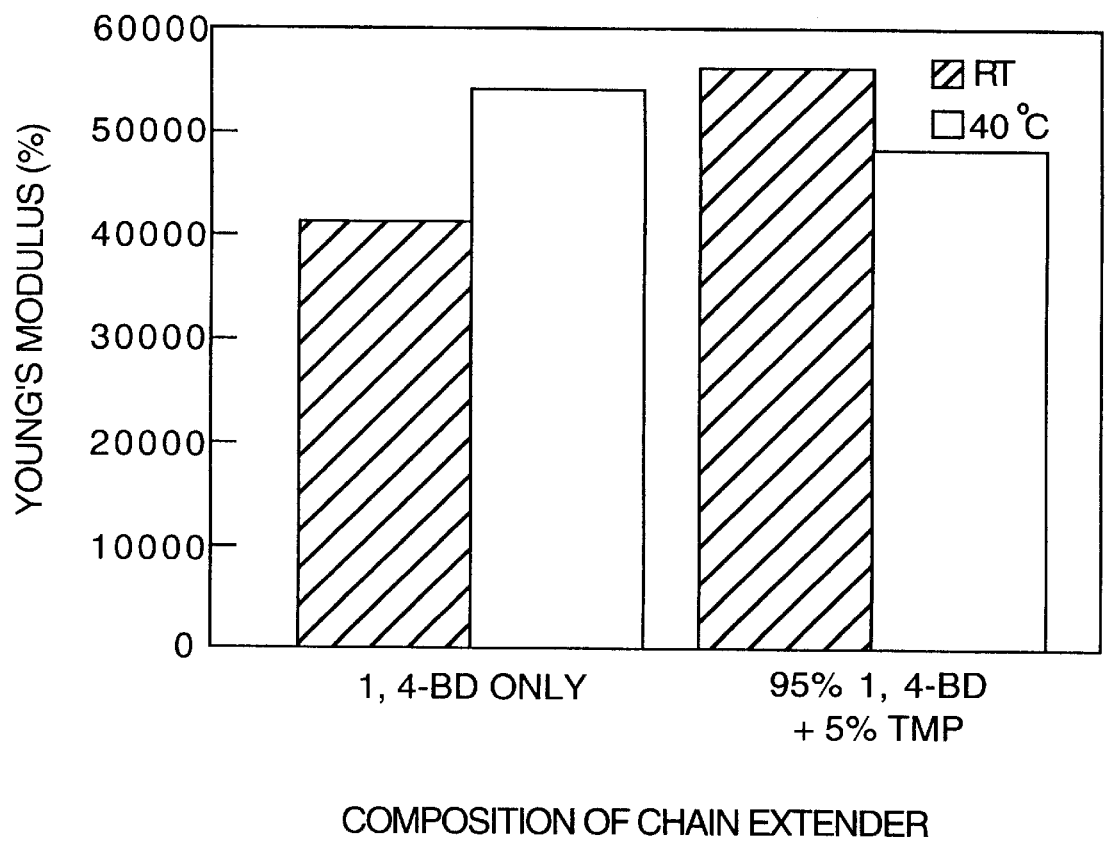
FIG. 17 is a bar graph of the effect of composition of chain extender on the toughness of a polyurethane elastoplastics based mixture of 1,4-BD+TMP, and Adiprene LFP X950A of and/or employed in the invention.

The resistance of different elastoplastics (polyurethane and UHMW-PE) was studied by immersing in a saline solution and measuring the weight change ofter 10, 20, and 33 days. Aromatic isocyanate elastoplastics exhibited a weight gain of 1–1.2%, but it leveled off after 10 days (FIG. 5). Surprisingly, the cycloaliphatic isocyanate-based elastoplastics exhibited somewhat higher weight gain. This could possibly be ascribed to the better ordered hard segments in the aromatic isocyanate-based elastoplastics as compared to Desmodur W which is a mixture of isomers. As expected, the UHMW-PE exhibited the lowest weight gain due to its nonpolar nature.

The properties of MDI-elastoplastics along with UHMW-PE were measured after immersion in saline solution for 30 days (Table 9). The properties of polyurethane elastoplastics changed slightly. It is interesting that the elongation at break of UHMW-PE decreased from 409% before swelling to 309% after swelling; a similar effect was observed when the properties of the UHMW-PE were measured at RT and 40° C.

Molded Elastoplastics

A cylindrical polyurethane elastoplastic sample was prepared by pouring the degassed resin system, A diprene LFP X950A/MDI/1,4-BD (65% hard segment concentration), into a cylindrical mold (FIG. 1, Table 8). The hardness of the cured elastoplatic measured at different spots was in the range of 66–70 Shore D. This sample may be utilized to machine artificial joints (FIG. 47).

TABLE 2

Properties of Polyurethane Elastoplastics Based on PTMO 650, 1,4-BD and MDI[a]

| Designation | 1 | 2 |
|---|---|---|
| Samples | PU by the One-shot method | PU by the Prepolymer method |
| Hard segment concentration (%) | 65 | 65 |
| Formulation (pbw) | | |
| Wt(PTMO 650) | 100 | |
| Wt(prepolymer)[b] | | 100 |
| Wt(1,4-BD) | 38.57 | 22.42 |
| Wt(MDI) | 147.14 | 42.92 |
| T-12 (%) | 0 | 0.002 |
| Remelting conditions | | |
| Properties | | |
| Hardness (Shore D) | 67 | 66 |
| Taber wear index[c] | 12.3 | 8.7 |
| Ultimate tensile strength (psi) | | |
| RT | 7348 | 6008 |
| 40° C. | 5926 | 6531 |
| Elongation at break (%) | | |
| RT | 642 | 489 |
| 40° C. | 555 | 508 |
| Toughness (psi) | | |
| RT | 25442 | 22996 |
| 40° C. | 30054 | 24897 |
| Young's Modulus (psi) | | |
| RT | 42370 | 37640 |

[a]Isocyanate index was 102; curing at 110° C. for 1 hr and postcuring at 110° C. for 24 hrs.
[b]NCO/OH = 2 for the prepolymer; the measured free NCO concentration = 6.91%.
[c]The abrading wheel was H-22, the wheel loading = 500 g and the test cycles = 4000.

TABLE 3

Effect of Equivalent Weight of PTMO-Diols on the Properties of Polyurethane Elastoplastics Based on 1,4-BD and MDI Prepared by One Shot Method[a]

| Designation | 1 | 2 | 3 | 4 |
|---|---|---|---|---|
| Samples | Polyurethane Elastomer | Polyurethane Elastomer | Polyurethane Elastomer | Ultrahigh molecular Weight polyethylene[b] |
| Hard segment concentration (%) | 65 | 65 | 70 | |
| Formulation (pbw) | | | | |
| Wt(PTMO 650) | 100 | | | |
| Wt(PTMO 1000) | | 100 | 100 | |
| Wt(1-4 BD) | 38.57 | 41.76 | 54.20 | |
| Wt(MDI) | 147.14 | 143.95 | 179.14 | |
| Remelting conditions | | | | 30 min. at 200° C. |
| Properties | | | | |
| Hardness (Shore D) | | | | |
| RT | 67 | 70 | 70 | 67 |
| Taber wear index[c] | 12.3 | | | 1.5 |
| Ultimate tensile strength (psi) | | | | |
| RT | 7340 | 5841 | 4898 | 7740 |
| 40° C. | 5920 | 6760 | 3370 | 6840 |
| Elongation at break (%) | | | | |
| RT | 642 | 500 | 269 | 409 |
| 40° C. | 555 | 603 | 85 | 211 |
| Young's Modulus (psi) | | | | |
| RT | 48390 | 48990 | 51100 | 74610 |
| 40° C. | 42370 | 31780 | 43100 | 53430 |

TABLE 3-continued

Effect of Equivalent Weight of PTMO-Diols on the Properties of
Polyurethane Elastoplastics Based on 1,4-BD and MDI Prepared by
One Shot Method[a]

| Designation | 1 | 2 | 3 | 4 |
|---|---|---|---|---|
| Yield strength (psi) | | | | |
| RT | 5695 | 4100 | 4898 | — |
| 40° C. | 2270 | 2232 | 1243 | 1909 |

[a]Isocyanate index was 102; curing at 110° C. for 1 hr and postcuring at 110° C. for 24 hrs.
[b]UHMW-PE was supplied by Bio Pro Inc.
[c]The abrading wheels are H-22, the wheel loading = 500 g and the test cycles = 4000.

TABLE 4

The Properties of Polyurethane Elastoplastics Based on PTMO 650,
1,4-BD and MDI, and Ultrahigh Molecular Weight Polyethylene
(UHMW-PE)[b]

| Designation | 1 | 2 | 3 |
|---|---|---|---|
| Samples | PU by the One-shot method | PU by the Prepolymer method | Ultrahigh molecular Weight polyethylene |
| Hard segment concentration (%) | 65 | 65 | |
| Formulation (pbw) | | | |
| Wt(PTMO 650) | 100 | | |
| Wt(prepolymer)[c] | | 100 | |
| Wt(1,4-BD) | 38.57 | 22.42 | |
| Wt(MDI) | 147.14 | 42.92 | |
| T-12 (%) | 0 | 0.002 | |
| Remelting conditions | | | 30 min. at 200° C. |
| Properties | | | |
| Hardness (Shore D) | 67 | 66 | 67 |
| Taber wear index[d] | 12.3 | 8.7 | 1.5 |
| Ultimate tensile strength (psi) | | | |
| RT | 7348 | 6008 | 7740 |
| 40° C. | 5926 | 6531 | 6840 |
| Elongation at break (%) | | | |
| RT | 642 | 489 | 409 |
| 40° C. | 555 | 508 | 211 |
| Young's Modulus (psi) | | | |
| RT | 42370 | 37640 | 74610 |
| 40° C. | 22810 | 18270 | 53430 |
| Yield Strength (psi) | | | |
| RT | 5695 | 5999 | — |
| 40° C. | 2270 | 924 | 1909 |
| Flexural Modulus (psi) | | | |
| RT | | | 53310 |
| Toughness (psi) | | | |
| RT | 25442 | 22996 | 18170 |
| 40° C. | 30054 | 24897 | 18933 |

[a]Isocyanate index was 102; curing at 110° C. for 1 hr and postcuring at 110° C. for 24 hrs.
[b]UHMW-PE was supplied by Bio Pro Inc.
[c]NCO/OH = 2 for the prepolymer; the measured free NCO concentration = 6.91%.
[d]The abrading wheels are H-22, the wheel loading = 500 g and the test cycles = 4000.

TABLE 5

The Properties of Polyurethane Elastoplastics Based on Adiprene LFP X950A[a], MDI and 1,4-BD[a]

| Designation | 1 | 2 | 3 |
|---|---|---|---|
| Samples | PU by the prepolymer method | PU by the prepolymer method | Ultrahigh molecular weight polyethylene[c] |
| Hard segment concentration (%) | 60 | 65 | |
| Formulation (pbw) | | | |
| Wt(Adiprene LFP X950A) | 100 | 100 | |
| Wt(MDI) | 68.15 | 89.05 | |
| Wt(1,4-BD) | 29.83 | 37.21 | |
| Remelting conditions | | | 30 min. at 200° C. |
| Properties | | | |
| Hardness (Shore D) | | | |
| RT | 67 | 68 | 67 |
| 40° C. | 64 | 62 | 64 |
| Taber wear index[d] | 9.3 | | 1.5 |
| Ultimate tensile strength (psi) | | | |
| RT | 7171 | 6292 | 7740 |
| 40° C. | 6575 | 6385 | 6840 |
| Elongation at break (%) | | | |
| RT | 565 | 492 | 409 |
| 40° C. | 645 | 600 | 211 |
| Young's Modulus (psi) | | | |
| RT | 36520 | 45010 | 74610 |
| 40° C. | 22770 | 31300 | 53430 |
| Yield strength (psi) | | | |
| RT | 1165 | 3902 | — |
| 40° C. | 2440 | 1299 | 1909 |

[a]The —NCO content in Adiprene FLP X950A was 5.46%
[b]The ratio of —NCO to —OH was 1.02; curing at 110° C. for 1 hr and postcuring at 110° C. for 24 hrs.
[c]UHMW-PE was supplied by Bio Pro Inc.
[d]The abrading wheels are H-22, the wheel loading = 500 g and the test cycles = 4000.

TABLE 6

Properties of Polyurethane Elastoplastics Based on 1,4-BD and PPDI Prepolymer[a]

| Designation | 1 | 2 | 3 | 4 |
|---|---|---|---|---|
| Samples | Prepolymer plus MDI | Prepolymer plus MDI | Prepolymer plus PPDI | Ultrahigh molecular Weight polyethylene[b] |
| Hard segment concentration (%) | 65 | 60 | 50 | |
| Formulation (pbw) | | | | |
| Wt(prepolymer) | 100 (NCO = 9.42%) | 100 (NCO = 9.42%) | 100 (NCO = 8.84%) | |
| Wt(MDI) | 61.01 | 43.18 | | |
| Wt(PPDI) | | | 16.32 | |
| Wt(1,4-BD) | 30.57 | 20.45 | 17.79 | |
| T-12 based on the amount of polyol (%) | 0 | 0 | 0.02 | |
| Remelting conditions | | | | 30 min. at 200° C. |
| Properties | | | | |
| Hardness (Shore D) | | | | |
| RT | 68 | 65 | 65 | 67 |
| 40° C. | 64 | 59 | | 64 |
| taber wear index[c] | | | | 1.5 |
| Ultimate tensile strength (psi) | | | | |
| RT | 9339 | 7769 | 4383 | 7740 |
| 40° C. | 8295 | 7661 | 3574 | 6840 |

TABLE 6-continued

Properties of Polyurethane Elastoplastics Based on 1,4-BD and PPDI Prepolymer[a]

| Designation | 1 | 2 | 3 | 4 |
|---|---|---|---|---|
| Elongation at break (%) | | | | |
| RT | 484 | 451 | 170 | 409 |
| 40° C. | 482 | 514 | 152 | 211 |
| Young's Modulus (psi) | | | | |
| RT | 48390 | 24920 | 20830 | 74610 |
| 40° C. | 43510 | 25720 | 28190 | 53430 |
| Yield strength (psi) | | | | |
| RT | 4375 | 4800 | 4376 | — |
| 40° C. | 3399 | 2902 | 387 | 1909 |
| Flexural Modulus (psi) | | | | |
| RT | 54680 | | | 53310 |
| Toughness (psi) | | | | |
| RT | 31642 | 28444 | 9365 | 18170 |
| 40° C. | 27120 | 23169 | 6756 | 18933 |

[a]Prepolymer of PPDI and PTMO 650, NCO/OH = 2.06.
[b]UHMW-PE was supplied by Bio Pro Inc.
[c]The abrading wheels are H-22, the wheel loading = 500 g and the test cycles = 4000.

TABLE 7

Properties of Polyurethane Elastoplastics Based on PTMO 650, $H_{12}$ MDI and 1,4-BD Prepared by One Shot Method

| Designation | 1 | 2 | 3 | 4 | 5 |
|---|---|---|---|---|---|
| Formulation (pbw) | | | | | |
| Wt(PTMO 650) | 100 | 100 | 100 | 100 | 100 |
| Wt(1,4-BD) | 48.79 | 48.79 | 48.79 | 48.79 | 48.79 |
| Wt($H_{12}$MDI) | 184.55 | 184.55 | 184.55 | 184.55 | 184.55 |
| Irganox 565 based on the amount of elastomer (%) | 0 | 0.03 | 0.03 | 0.03 | 0.3 |
| Curing conditions | 110° C. (1 hr) | 110° C. (1 hr) | 145° C. (1 hr) | 145° C. (2 hrs) | 145 ° C. (1 hr) |
| Post curing conditions | 110° C. (24 hrs) | 110° C. (24 hrs) | 110° C. (24 hrs) | 145° C. (20 hrs) | 145° C. (20 hrs) |
| Properties | | | | | |
| Hardness (Shore D) | 69 | 73 | 73 | 72 | 73 |
| Taber wear index[b] | | 6.3 | | 5.5 | 75 |
| Ultimate tensile strength (psi) | | | | | |
| RT | 7109 | 8298 | 6704 | 6899 | 7158 |
| 40° C. | 4866 | 5856 | 4795 | 5003 | 5630 |
| Elongation at break (%) | | | | | |
| RT | 374 | 413 | 348 | 372 | 362 |
| 40° C. | 395 | 475 | 363 | 391 | 443 |
| Toughness (psi) | | | | | |
| RT | | 19904 | | | |
| 40° C. | | 13681 | | | |
| Young's Modulus (psi) | | | | | |
| RT | 81720 | 84090 | 93330 | 86030 | 79100 |
| Yield strength (psi) | | | | | |
| RT | 4599 | 3126 | 1871 | 1798 | 679 |
| Flexural Modulus (psi) | | | | | |
| RT | | 89600 | | | |

[a]Hard segment was 70%; isocyanate index was 102 and T-12 content was 0.01% based on the amount of polyol.
[b]The abrading wheels are H-22, the wheel loading = 500 g and the test cycles = 4000.

TABLE 8

Formulation and Hardness of Cylindric Sample of Polyurethane Elastoplastics Based on Adiprene LFP X950A[a], MDI and 1,4-BD[b]

| Designation | 1 |
|---|---|
| Formulation (pbw) | |
| Wt(Adiprene LFP X950A) | 100 |
| Wt(MDI) | 88.52 |
| Wt(1,4-BD) | 37.09 |
| Hard segment concentration (%) | 65 |
| Isocyanate Index | 102 |
| Properties | |
| Hardness (Shore D) | |
| RT | 66 ≈ 70 |
| 40° C. | 63 ≈ 68 |

[a]The —NCO content in Adiprene FLP X950A was 5.52%
[b]The ratio of —NCO to —OH was 1.02. Adiprene was first mixed with MDI at 80° C., then the mixture was dried under a vacuum of 1–3 mmHg at ≈70° C. for at least 2 hours. Finally, the mixture of Adiprene and MDI was mixed with 1,4-BD at 60° C. under stirring and vacuum. Curing at 125° C. for 1 hr and postcuring at 125° C. for 16 hrs.

TABLE 9

Effect of Saline Immersion at 40° C. for 30 days on the Properties of Elastoplastics[a]

| Designation | 1 | 2 | 3 |
|---|---|---|---|
| Samples | PU by the one-shot method[b] | PU by the prepolymer method[b] | Ultrahigh molecular weight polyethylene[c] |
| Hard segment concentration (%) | 65 | 65 | |
| Formulation (pbw) | | | |
| Wt(PTMO 650) | 100 | | |
| Wt(prepolymer)[d] | | 100 | |
| Wt(1,4-BD) | 38.57 | 22.42 | |
| Wt(MDI) | 147.14 | 42.91 | |
| T-12 (%) | 0 | 0.002 | |
| Remelting conditions | | | 30 min. at 200° C. |
| Properties | | | |
| Hardness (Shore D) | | | |
| Before immersion | 67 | 66 | 67 |
| After immersion | 67 | 67 | 67 |
| Ultimate tensile strength (psi) | | | |
| Before immersion | 7348 | 6008 | 7740 |
| After immersion | 6844 | 5533 | 7649 |
| Elongation at break (%) | | | |
| Before immersion | 642 | 489 | 409 |
| After immersion | 598 | 515 | 309 |
| Young's Modulus (psi) | | | |
| Before immersion | 42370 | 37640 | 74610 |
| After immersion | 22320 | 15090 | 41310 |
| Yield strength (psi) | | | |
| Before immersion | 5695 | 5999 | — |
| After immersion | 7635 | — | 1909 |

[a]Immersion test was carried out at 40° C. for 30 days
[b]Isocyanate index was 102; curing condition was 105° C. (1 hr) and postcuring condition was 105° C. (24 hrs).
[c]UHMW-PE was supplied by BioPro Inc.
[d]NCO/OH = 2 for the prepolymer; the measured free NCO concentration = 6.91%.

EXAMPLE SET 2

Analogous to that which is set forth in Example Set 1, chemicals employed in Example Set 2 are listed in Table 10. Polyols and chain extenders were dried under a vacuum, and the isocyanates were employed as received from the suppliers. The isocyanate content, again, was determined by the di-n-butylamine method.

TABLE 10

Materials

| Designation | Chemical Identification | Eq. Wt. | Supplier |
|---|---|---|---|
| PTMO 650 | Poly(oxytetramethylene) glycol | 335.5 | DuPont |
| PTMO 1000 | Poly(oxytetramethylene) glycol | 494.5 | DuPont |
| UHMW-PE | Ultrahigh Molecular Weight Polyethylene (1050 LOT 332831 Extruded) | | Bio Pro Inc. |
| Adiprene LFP X950A | Prepolymers of polyether polyol with PPDI ($C_{NCO}$ = 5.46 ≈ 5.52%) | | Uniroyal Chemical |
| 1,4-BD | 1,4-Butanediol, 99% | 45 | GAF Corporation |
| TMP | Trimethylolpropane, 97% | 44.7 | Eastman Kodak Co. |
| MDI (Mondur M) | 4,4'-Diphenylmethane diisocyanate | 125 | Bayer AG |
| $H_{12}$ MDI (Desmodur W) | Methylene Bis(4-cyclohexyl isocyanate) | 131 | Bayer Co. |
| PPDI | Para-phenylene diisocyanate | | DuPont |
| T-12 | Dibutyltin dilaurate | | Air Products |
| Irganox 565 | Antioxidant | | Ciba Geigy Corporation |

Prepolymer methods were employed, in general, which can use pressures about from 5,000–30,000 psi for curing test sheets, e.g., 20,000 psi. Results are reported in Tables 11–14. Mixtures of two polyols were effectively employed. Cross-linking (slight) was also effectively employed (e.g., Table 2, cols. 2 & 4). Compare, FIGS. 6–17.

TABLE 11

Properties of Polyurethane Elastoplastics Based on Mixture of 1,4-BD + TMP, and PPDI Prepolymer of Mixture of PTMO650 + PTMO1000

| Designation | 1 | 2 | 3 | 4 | 5 |
|---|---|---|---|---|---|
| Samples | PU | PU | PU | PU | UHMW-PE |
| Formulation of mixture of polyols (pbw) | | | | | |
| Wt(PTMO 650, 50% by equivalent) | 100 | 100 | | | |
| Wt(PTMO 1000, 50% by equivalent) | 147.39 | 147.39 | | | |
| Wt(PTMO 650, 80% by equivalent) | | | 100 | 100 | |
| Wt(PTMO 1000, 20% by equivalent) | | | 36.85 | 36.85 | |
| Formulation of prepolymer (pbw) | | | | | |
| Wt(PTMO650 + PTMO1000) | 100 | 100 | 100 | 100 | |
| Wt(PPDI) | 39.72 | 39.72 | 44.88 | 44.88 | |
| Formulation of mixture of extenders (pbw) | | | | | |
| Wt(1,4-BD, 95% by equivalent) | | 100 | | 100 | |
| Wt(TMP, 5% by equivalent) | | 5.28 | | 5.28 | |
| Formulation of elastomer[a] (pbw) | | | | | |
| Wt(Prepolymer) | 100 | 100 | 100 | 100 | |
| Wt(MDI) | 70.90 | 70.89 | 65.11 | 65.11 | |
| Wt(1,4-BD only) | 33.59 | | 32.09 | | |
| Wt(1,4-BD + TMP) | | 33.59 | | 32.10 | |
| T-12 based on the amount of polyol (%) | 0.002 | 0.002 | 0.002 | 0.002 | |
| Remelting conditions | | | | | 30 min. at 200° C.) |
| Properties | | | | | |
| Hardness (Shore D) | 70 | 69 | 69 | 69 | 66 |
| Table wear index[a] | 11.0 | 10.8 | 7.3 | 7.3 | |
| Ultimate tensile strength (psi) | | | | | |
| RT | 7497 | 8345 | 7401 | 7755 | 8179 |
| 40° C. | 5291 | 7708 | 7671 | 8073 | 6622 |
| Elongation at break (%) | | | | | |
| RT | 540 | 458 | 520 | 562 | 460 |

TABLE 11-continued

Properties of Polyurethane Elastoplastics Based on Mixture of 1,4-BD + TMP, and PPDI Prepolymer of Mixture of PTMO650 + PTMO1000

| Designation | 1 | 2 | 3 | 4 | 5 |
|---|---|---|---|---|---|
| 40° C. | 437 | 530 | 710 | 569 | 524 |
| Young's Modulus (psi) | | | | | |
| RT | 31720 | 25770 | 39980 | 40580 | 23520 |
| 40° C. | 25400 | 29820 | 31650 | 37880 | 36350 |
| Yield strength (psi) | | | | | |
| RT | 3649 | 3818 | 1945 | 2506 | |
| 40° C. | 2198 | 2871 | 2238 | 3276 | |
| Toughness (psi) | | | | | |
| RT | 29343 | 25917 | 26628 | 33237 | 24200 |
| 40° C. | 19003 | 25432 | 35914 | 28203 | 20482 |

[a]Isocyanate index = 102
[b]The abrading wheels are H-22, the wheel loading = 500 g and the test cycles = 4000.

TABLE 12

Effect of Isocyanate Index on the Properties of Polyurethane Elastoplastics Based on Mixture of 1,4-BD + TMP), and PPDI Prepolymer of Mixture of 50% PTMO650 + 50% PTMO1000

| Designation | 1 | 2 | 3 | 4 | 5 |
|---|---|---|---|---|---|
| Samples | PU (TMP = 0) | PU (TMP = 0) | PU (TMP = 5%) | PU (TMP = 5%) | UHMW-PE |
| Isocyanate Index | 102 | 105 | 102 | 105 | |
| Formulation of mixture of polyols (pbw) | | | | | |
| Wt(PTMO 650, 50% by equivalent) | 100 | 100 | 100 | 100 | |
| Wt(PTMO 1000, 50% by equivalent) | 147.39 | 147.39 | 147.39 | 147.39 | |
| Formulation of prepolymer (pbw) | | | | | |
| Wt(PTMO650 + PTMO1000) | 100 | 100 | 100 | 100 | |
| Wt(PPDI) | 39.72 | 39.72 | 39.72 | 39.72 | |
| Formulation of mixture of extenders (pbw) | | | | | |
| Wt(1,4-BD, 95% by equivalent) | | | 100 | 100 | |
| Wt(TMP, 5% by equivalent) | | | 5.28 | 5.28 | |
| Formulation of elastomer (pbw) | | | | | |
| Wt(Prepolymer) | 100 | 100 | 100 | 100 | |
| Wt(MDI) | 70.90 | 71.61 | 70.89 | 71.61 | |
| Wt(1,4-BD only) | 33.59 | 32.87 | | | |
| Wt(1,4-BD + TMP) | | | 33.59 | 32.88 | |
| T-12 based on the amount of polyol (%) | 0.002 | 0.002 | 0.002 | 0.002 | |
| Remelting conditions | | | | | 30 min. at 200° C.) |
| Properties | | | | | |
| Hardness (Shore D) | 70 | 69 | 69 | 70 | 66 |
| Taber wear index[a] | 11.0 | 13.3 | 10.8 | 6.8 | |
| Ultimate tensile strength (psi) | | | | | |
| RT | 7497 | 7689 | 8345 | 7351 | 8179 |
| 40° C. | 5291 | 7779 | 7708 | 7018 | 6622 |
| Elongation at break (%) | | | | | |
| RT | 540 | 534 | 485 | 375 | 460 |
| 40° C. | 437 | 644 | 530 | 478 | 524 |
| Young's Modulus (psi) | | | | | |
| RT | 31720 | 48880 | 25770 | 40510 | 23520 |
| 40° C. | 25400 | 33160 | 29820 | 30690 | 36350 |

TABLE 12-continued

Effect of Isocyanate Index on the Properties of Polyurethane
Elastoplastics Based on Mixture of 1,4-BD + TMP), and PPDI
Prepolymer of Mixture of 50% PTMO650 + 50% PTMO1000

| Designation | 1 | 2 | 3 | 4 | 5 |
|---|---|---|---|---|---|
| Yield strength (psi) | | | | | |
| RT | 3649 | 1865 | 3813 | 1886 | |
| 40° C. | 2198 | 2312 | 2871 | 2326 | |
| Toughness (psi) | | | | | |
| RT | 29343 | 19514 | 25917 | 17900 | 24200 |
| 40° C. | 19003 | 32521 | 25432 | 21125 | 20482 |

[a]The abrading wheels are H-22, the wheel loading = 500 g and the test cycles = 4000.

TABLE 13

Properties of Polyurethane Elastoplastics Based on Mixture of 1,4-BD +
TMP, and Adiprene LFP X950A[a]

| Designation | | 1 | |
|---|---|---|---|
| Chain extender | | 1,4-BD only | 95% of 1,-BD + 5% of TMP by equivalent |
| Formulation of mixture of extenders (pbs) | | | |
| Wt (1,4-BD) | | 100 | |
| Wt (TMP) | | | 5.28 |
| Formulation of elastomer[b] (pbw) | | | |
| Wt (Prepolymer) | | 100 | 100 |
| Wt (MDI) | | 92.52 | 92.52 |
| Wt (1,4-BD only) | | 33.09 | |
| Wt (1,4-BD + TMP) | | | 33.09 |
| T-12 based on the amount of polyol (%) | | 0.002 | 0.002 |
| Properties | | | |
| Hardness (Shore D) | | 70 | 69 |
| Taber wear index[c] | | | 9.3 |
| Ultimate tensile strength (psi) | RT | 6899 | 6656 |
| | 40° C. | 6640 | 6093 |
| Elongation at break (%) | RT | 276 | 291 |
| | 40° C. | 331 | 278 |
| Young's Modulus (psi) | RT | 50340 | 38620 |
| | 40° C. | 34210 | 32850 |
| Yield strength (psi) | RT | 2098 | 2730 |
| | 40° C. | 2458 | 2514 |
| Flexural Modulus (psi) | RT | | |
| Toughness (psi) | RT | 11189 | 15203 |
| | 40° C. | 14490 | 12945 |

[a]The —NCO content in adiprene FLP X950A was 5.52%
[b]Isocyanate index = 102
[c]The abrading wheels are II-22, the wheel loading = 500 g and the test cycles = 4000.

TABLE 14

Properties of Ultrahigh Molecular Polyethylene

| Designation | | 1 | |
|---|---|---|---|
| Samples | | Ultrahigh molecular weight polyethylene (1050 LOT 332831 Extruded) | Ultrahigh molecular weight polyethylene |
| Remelting conditions Properties | | 30 min. at 200° C. | 30 min. at 200° C. |
| Hardness (Shore D) | | 66 | 67 |
| Taber wear index[c] | | | 1.5 |
| Ultimate tensile | RT | 8179 | 7740 |

TABLE 14-continued

Properties of Ultrahigh Molecular Polyethylene

| Designation | | 1 | |
|---|---|---|---|
| strength (psi) | 40° C. | 6622 | 6840 |
| Elongation at break (%) | RT | 460 | 409 |
| | 40° C. | 524 | 211 |
| Young's Modulus (psi) | RT | 23520 | 74610 |
| | 40° C. | 36350 | |
| Flexural Modulus (psi) | RT | | 53310 |
| Toughness (psi) | RT | 24200 | 18170 |
| | 40° C. | 20482 | 18933 |

Results, accordingly, as persons skilled in the art would appreciate, were highly favorable, especially in comparison to UHMW-PE (which is compared at approximately the same hardness values, e.g., 66–69).

Figure 47A:
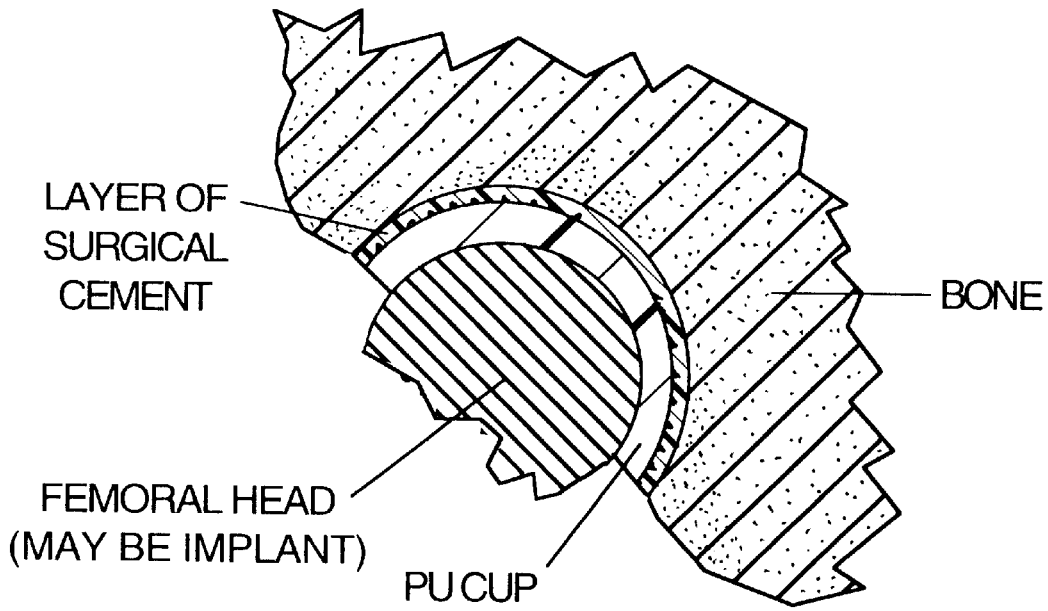
Figure 47B:
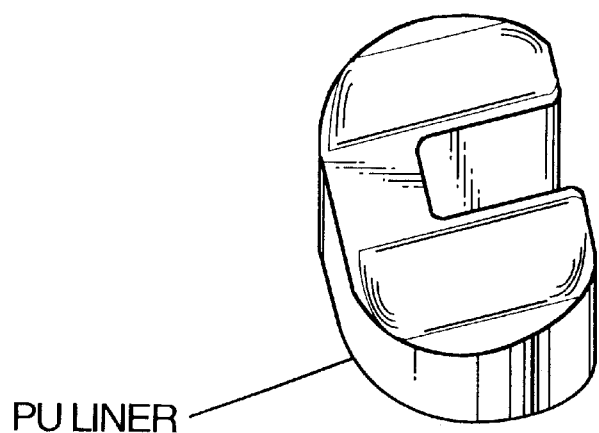

Such samples may be utilized to machine artificial joints such as depicted with FIG. 47. In particular, acetabular cups FIG. 47A and tibial tray liners FIG. 47B, for example, may be machined therefrom and further tested.

Accordingly, polyurethane elastoplastics in the hardness range of Shore D 65–70 were prepared, tested and compared to ultrahigh density polyethylene. Both aromatic (MDI and PPDI) and cycloaliphatic (H12MDI) isocyanate-based electroplastics were prepared. Poly(oxytetramethylene) glycols of 650 and 100 MW were utilized as the flexible segment and 1,4-BD as the chain extender. Of the materials studied, the electroplastic PPDI/MDI/1,4-BD/PTMO650 exhibited very good physico-mechanical properties. The tensile strength, elongation at break, and toughness, both at RT and 40° C., were equivalent to, and in some cases exceeded, the values obtained for the UHMW-PE.

EXAMPLE SET 3

I. EXPERIMENTAL

Materials

The chemicals utilized in the elastoplastics preparation are shown in Table 15:

TABLE 15

Materials

| Designation | Chemical Identification | Eq. Wt. | Supplier |
|---|---|---|---|
| PTMO 650 | Poly(oxytetramethylene) glycol | 335.5 | DuPont |
| PTMO 1000 | Poly(oxytetramethylene) glycol | 494.5 | DuPont |
| PC 1733 | Polycarbonate diol | 441.4 | Stahl USA |
| UHMW-PE (Unfilled) | Ultra High Molecular Weight Polyethylene (Unfilled) | | BioPro |
| UHMW-PE (Filled) | Ultra High Molecular Weight Polyethylene (Filled) | | BioPro |
| 1,4-BD | 1,4-Butanediol, 99% | 45 | GAF Corporation |
| TMP | Trimethylolpropane, 97% | 44.7 | Eastman Kodak Co. |
| HQEE | Hydroquinone di-(β-hydroxyethyl) ether | 99.1 | Aldrich Chemical Co. |
| MDI (Mondur M) | 4,4'-Diphenylmethane diisocyanate | 125 | Bayer AG |
| PPDI | Para-phenylene diisocyanate | 80 | DuPont |
| T-12 | Dibutyltin dilaurate | | Air Products |
| Irganox 565 | Antioxidant | | Ciba Geigy Corporation |

Preparation of Elastoplastics Based on PPDI/MDI/1,4-BD/PTMO-Diols

Polyurethane elastoplastics were prepared using the two step prepolymer procedure. In the first step, PPDI-based NCO-prepolymers were prepared using a mixture of PTMO-1000 and PTMO650 polyols at 20/80 and 50/50 weight ratios. The prepolymer was prepared using the following procedure: PPDI(flaked) was placed in a 1-L glass reaction kettle which was equipped with a stirrer under a continuous flow of nitrogen. The PTMO-1000/PTMO-650 polyol mixture (50/50 and 20/80 weight ratio) was heated to 60° C. and added under mixing to the PPDI. The reaction exotherm temperature rose to 90° C. and stayed there for about one hour. The theoretical NCO% was reached at that time. Afterwards, the temperature of the prepolymer started to decrease. In the second step, a specified amount of the prepolymer and free isocyanate (MDI) were mixed and heated to 110° C. for homogenization. The mixture was transferred to a reactor and degassed for two hours under vacuum at 80° C. Afterwards, the temperature was decreased to 60° C., 1,4-BD or a mixture of 1,4-BD/TMP (previously degassed) was added and the reaction mixture degassed quickly before transferring to the mold. The mold, covered with Teflon sheets, was placed in a Carver press which was preheated at 125° C. When gelation occurred (as determined by string formation), the mold was compressed to ~20,000 psi at 125° C. for one hour. Finally, the mold was placed in an oven at 125° C. for 24 hours postcuring.

Preparation of Elastoplastics Based on PPDI/Desmophen C-200

Elastoplastics based on polycarbonate diol (Desmophen C-200 or PC-1733) were prepared by reacting a mixture of NCO-terminated prepolymer and free isocyanate with a mixture of OH-terminated prepolymer and HQEE chain extender. This synthetic procedure was developed due to the high reactivity of the polycarbonate polyol. By using pre-reacted adducts it was possible to control the polymerization of polyurethane in the preparation procedure. The NCO-terminated prepolymers were prepared by reacting PPDI and polyol at an equivalent NCO/OH ratio of 2/1. The OH-terminated prepolymer was prepared by reacting polycarbonate diols and PPDI at an OH/NCO equivalent ratio 2/1. The prepolymers were prepared as described above.

UHMW-PE Sheets

The sheet samples of ultrahigh density polyethylene were prepared by remelting a cylindrical slice cut from a UHMW-PE bar (provided by Biopro Co.) in a Carver press at 200° C.

Evaluation of the Properties of Elastoplastics

The following properties of the polyurethane elastoplastics and ultrahigh molecular weight polyethylene were tested:

Shore D hardness (ASTM D-2240-75)
Stress-strain properties at RT and 40° C.
Tear resistance, Graves die C(ASTM D-624-72)
Compressive strength and modulus (ASTM D-695)
Flexural modulus (ASTM D-79084)
Shear strength (ASTM D 732-85)
Abrasion resistance (Taber Abrader)

Most of the physico-mechanical properties were measured at both RT and 400° C. The glass transition temperature (Tg) was measured by differential scanning calorimetry (DSC) and/or by using dynamic mechanical analysis, with softening by using thermo-mechanical analysis (TMA).

The hydrolytic resistance of the polyurethanes was studied by immersion in saline solution. The weight changes were measured periodically as well as the retention of properties after one month of immersion.

II. RESULTS AND DISCUSSIONS

Properties of PPDI/MDI/1,4-BD/PTMO Elastoplastics

Figure 18:
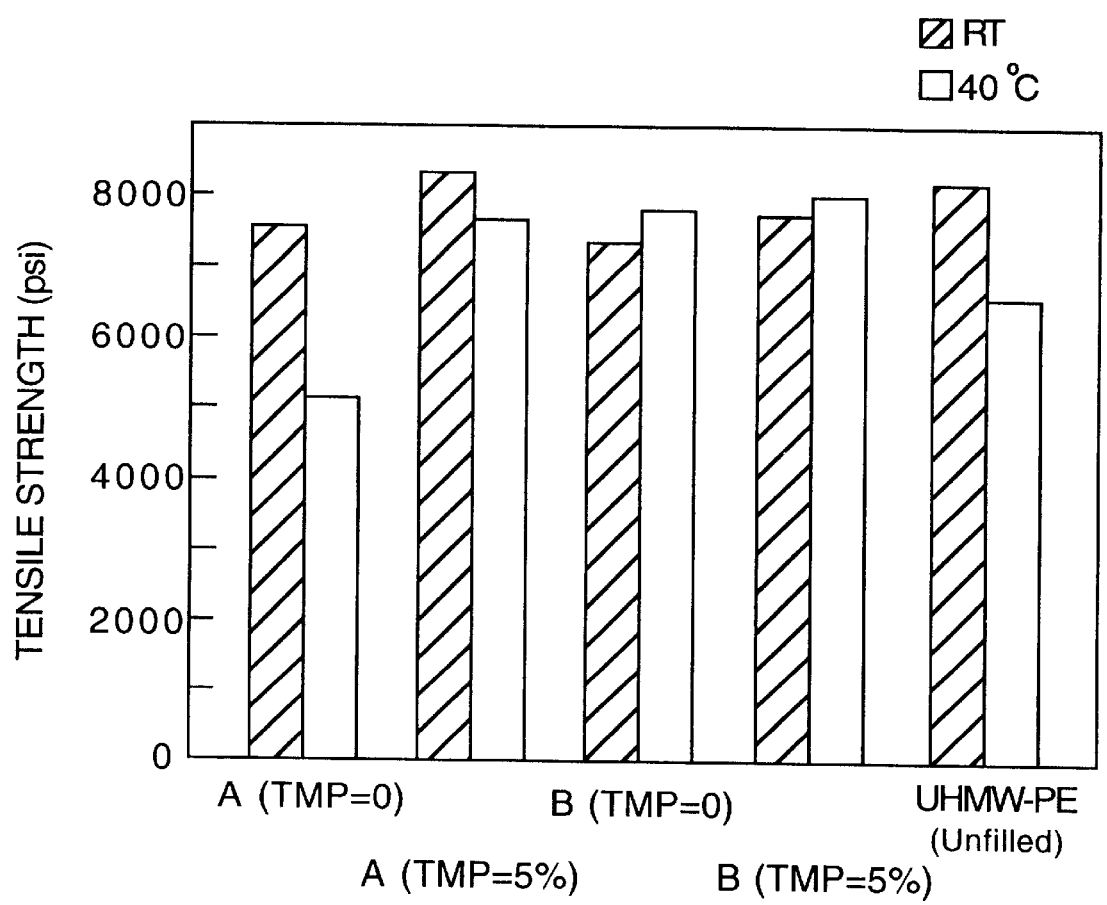
FIG. 18 is a bar graph of tensile strength of certain polyurethane elastoplastics, with a control (unfilled UHMW-PE).
Figure 19:
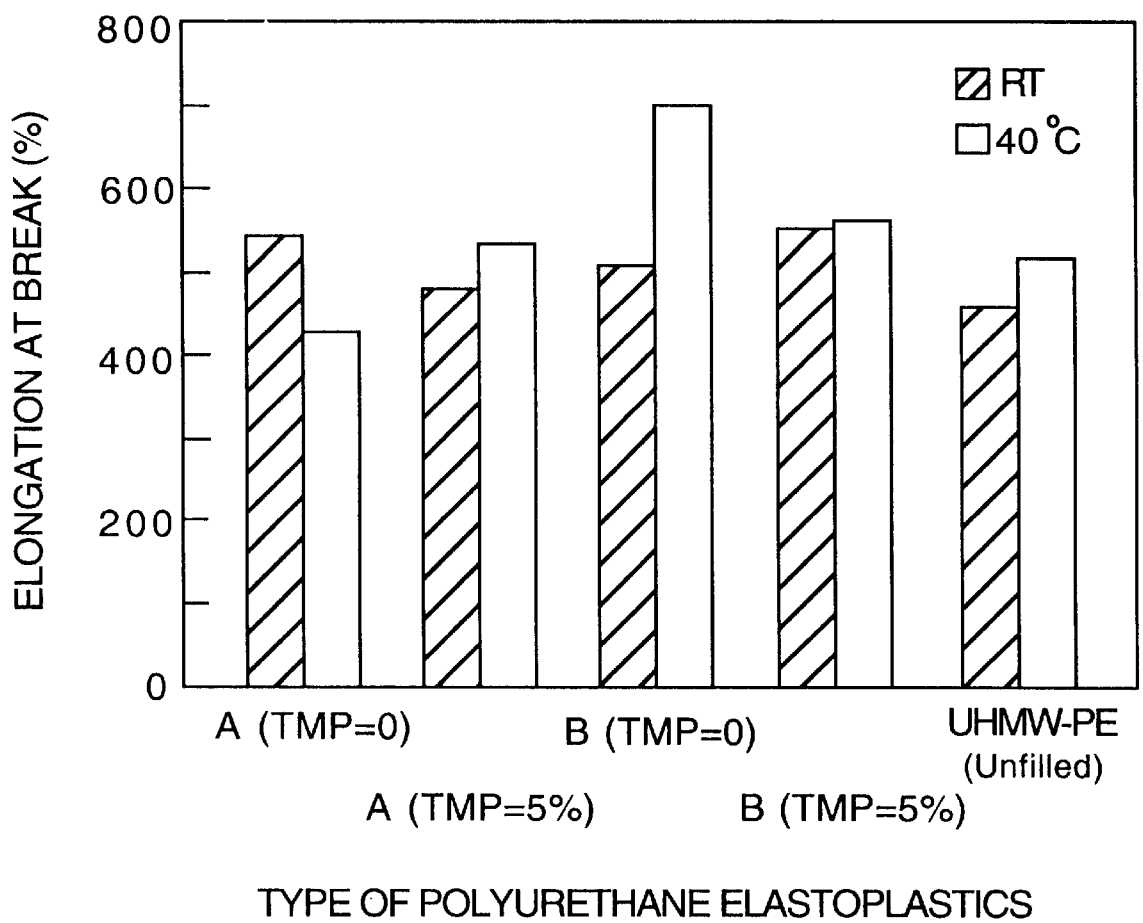
FIG. 19 is a bar graph of elongation of certain polyurethane elastoplastics, with a control (unfilled UHMW-PE).
Figure 20:
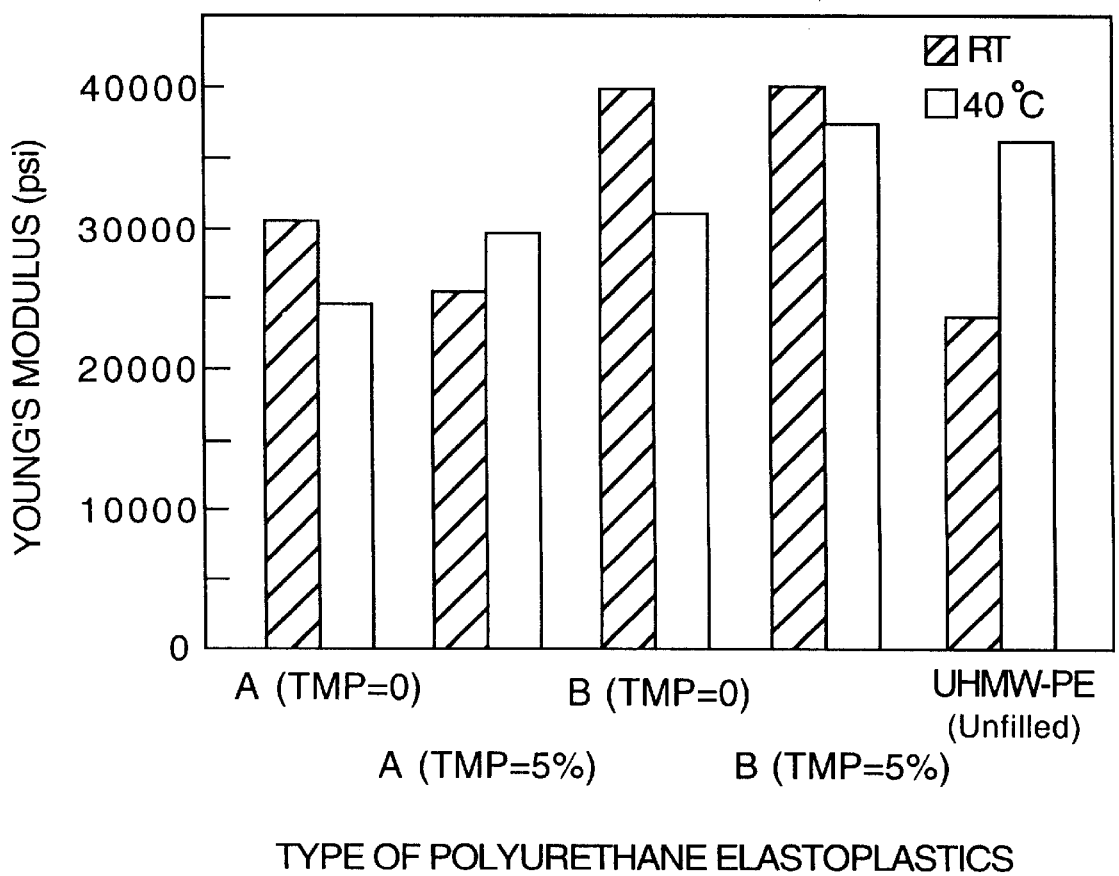
FIG. 20 is a bar graph of Young's modulus of certain polyurethane elastoplastics, with a control (unfilled UHMW-PE).
Figure 21:
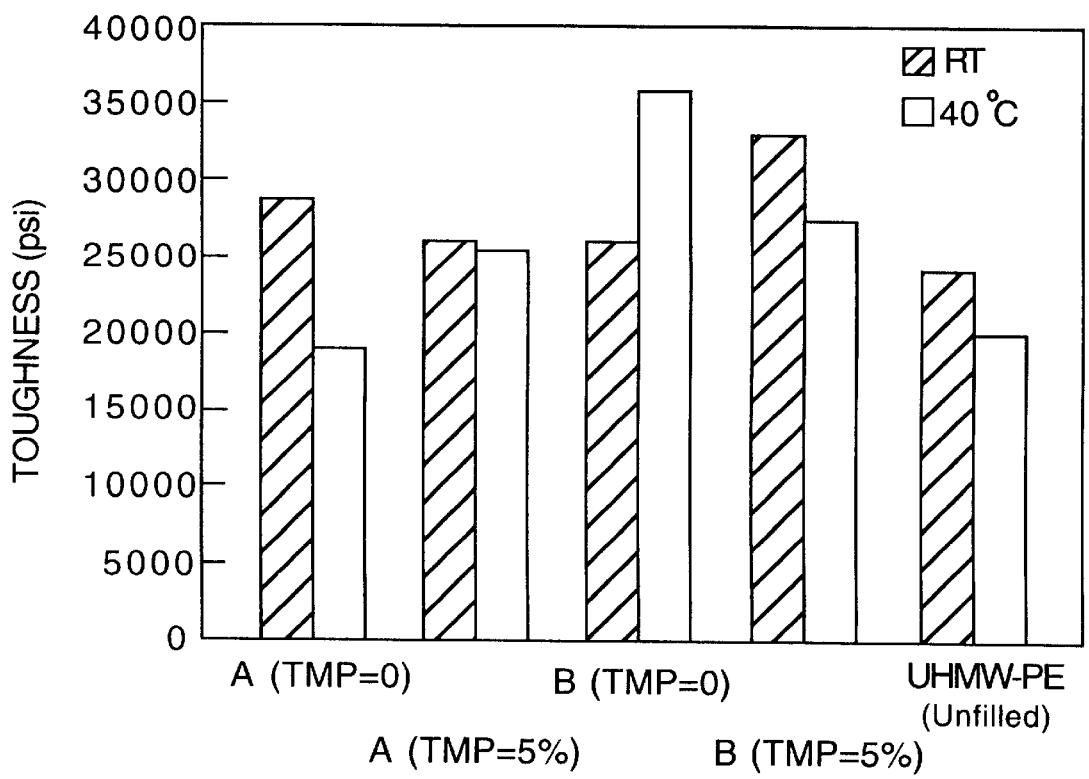
FIG. 21 is a bar graph of Young's modulus of certain polyurethane elastoplastics, with a control (unfilled UHMW-PE).
Figure 22:
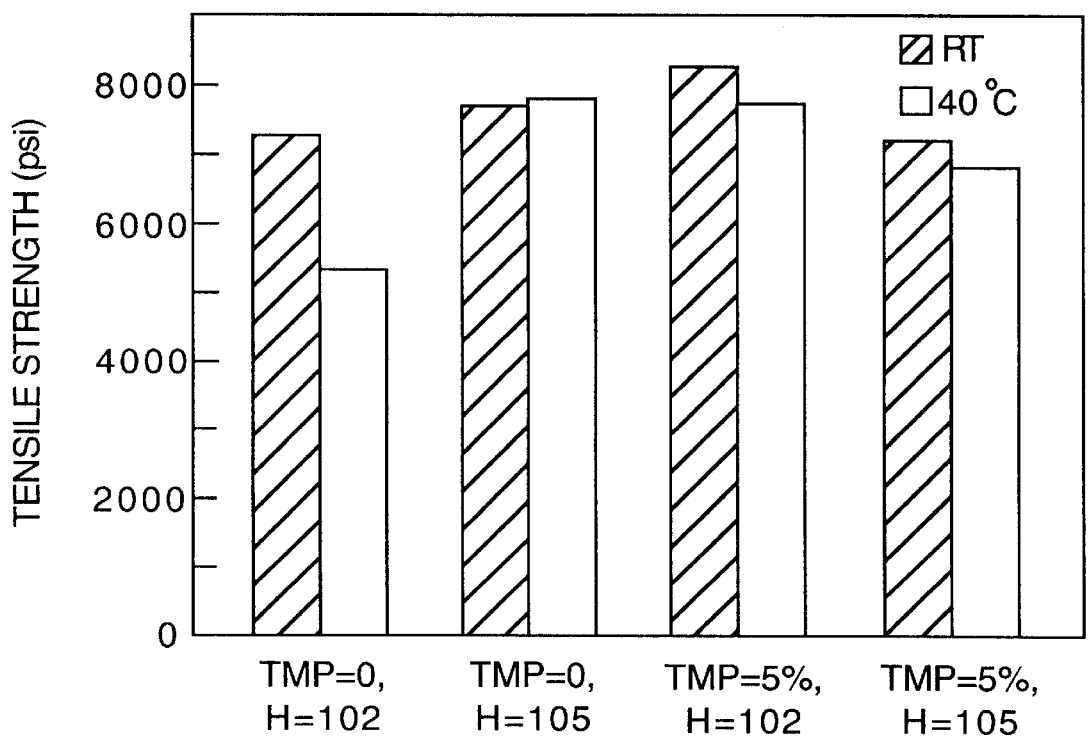
FIG. 22 is a bar graph of the effect of isocyanate index on tensile strength of polyurethane elastoplastic based on PPDI prepolymer of 50% PTMO-650 and 50% PTMO-1000.
Figure 23:
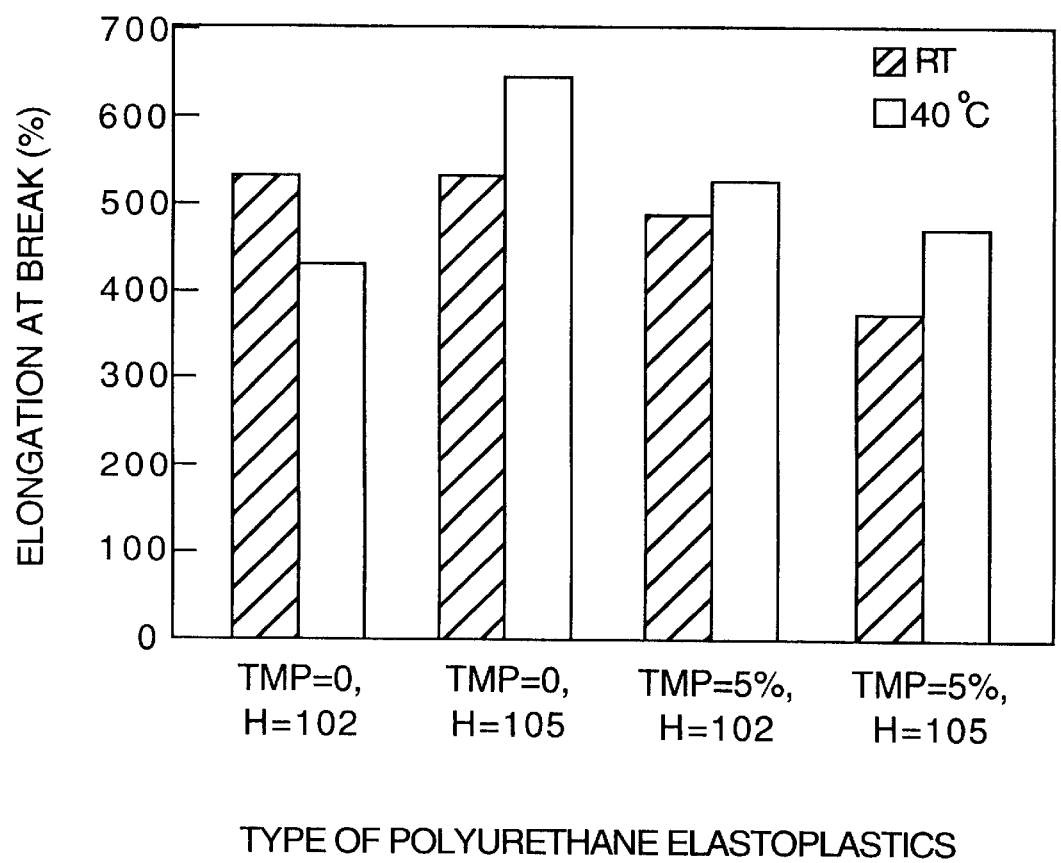
FIG. 23 is a bar graph of the effect of isocyanate index on elongation of polyurethane elastoplastic based on PPDI prepolymer of 50% PTMO-650 and 50% PTMO-1000.
Figure 24:
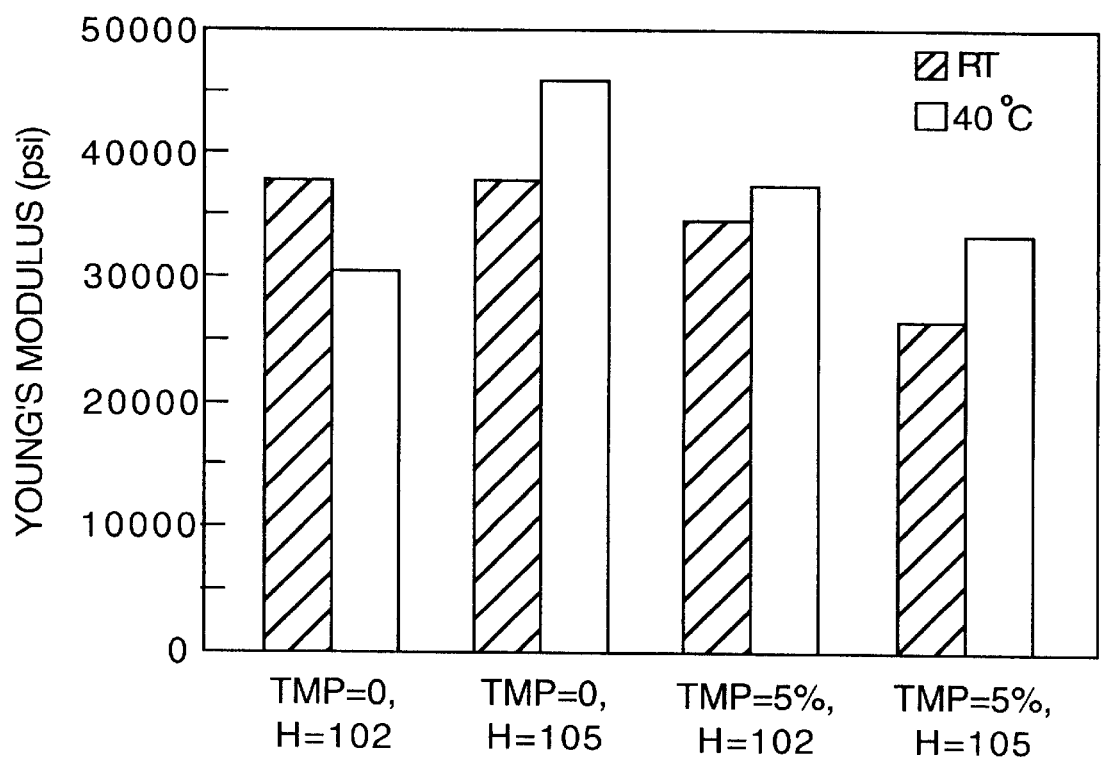
FIG. 24 is a bar graph of the effect of isocyanate index on Young's modulus of polyurethane elastoplastic based on PPDI prepolymer of 50% PTMO-650 and 50% PTMO-1000.
Figure 25:
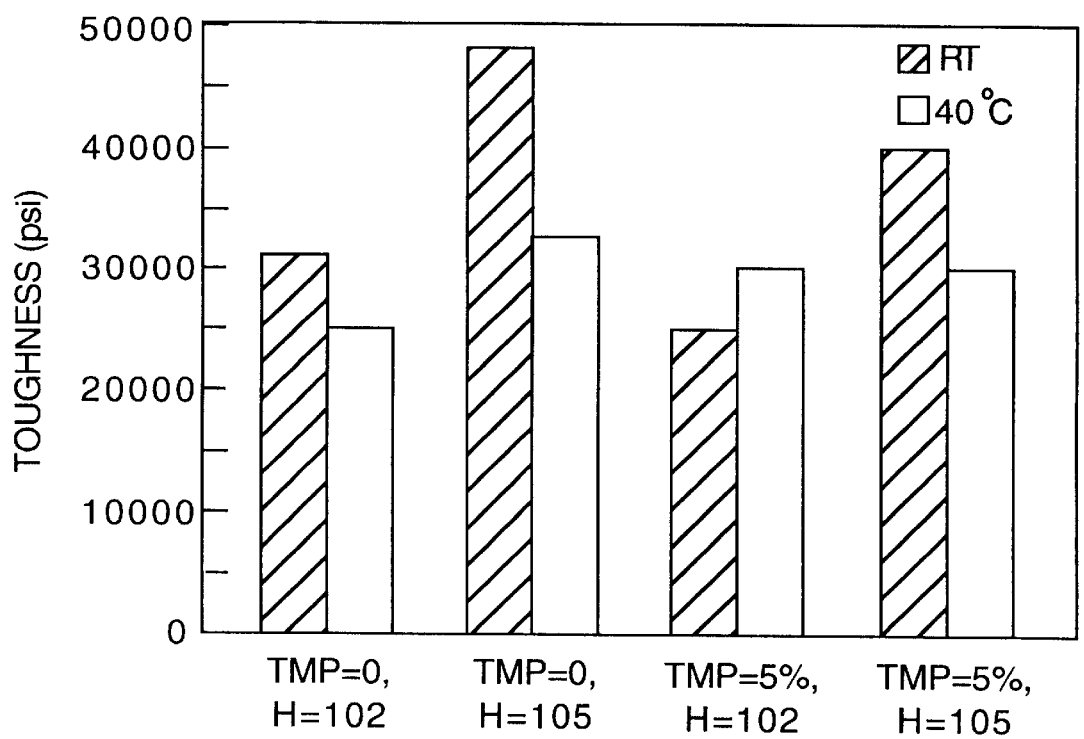
FIG. 25 is a bar graph of the effect of isocyanate index on toughness of polyurethane elastoplastic based on PPDI prepolymer of 50% PTMO-650 and 50% PTMO-1000.

The properties of the PPDI-based elastoplastics prepared using a mixture of poly(oxytetramethylene)glycols (PTMO650 and PTMO1000) are shown in Table 16. The elastoplastics 1 and 2 were prepared with a 50/50 PTMO1000/PTMO650 blend and samples 3 and 4 using an 20/80 PTMO1000/PTMO650 blend. Thermoplastic elastoplastics were prepared by extending the prepolymers with 1,4-BD and slightly crosslinked elastoplastics by using a 5/95 blend of TMP/1,4-BD at an isocyanate index of 102. These elastoplastics exhibited very good tensile strengths (7400 psi–8350 psi) and the elongation at break was still very good (460–560). The tensile strength of the polyurethane elastoplastics changed slightly at 40° C. (except sample 1), while the tensile strength of UHMW-PE(unfilled) decreased more, especially in the case of unfilled material (from 8179 psi at RT to 6622 psi at 40° C.) FIG. 18). The Young's moduli of the polyurethane elastoplastics were similar or higher than the unfilled UHMW-PE (FIG. 20). The Young's modulus of the filled UHMW-PE was much higher than that of the unfilled type, as expected (Table 17). The tear strength of some PTMO-based polyurethane elastoplastics was found to be 911 and 1099 psi, exceeding significantly the 694 psi measured for UHMW-PE (filled) (Table 18). The toughness of the polyurethane elastoplastics, which is the area under the stress-strain curve was higher than that of UHMW-PE (FIG. 21).

The flexural modulus for the elastoplastics based on the polyol blends (80/20 PTMO650/PTMO1000 mixture) was significantly higher than that based on PTMO650 only (Table 18) and UHMW-PE (filled). The compressive strength and modulus of the slightly crosslinked elastoplastics was somewhat higher than that of linear polyurethane elastoplastic.

The average shear strength of polyurethane elastoplastics and UHMW-PE were similar.

The effect of isocyanate index on the properties of polyurethane elastoplastic based on the PPDI/(PTMO1000/ PTMO650, 50/50) prepolymer was studied (Table 19). Increased isocyanate index is expected to impart some crosslinking to the polyurethanes, due to the selfpolymerization or addition reactions of isocyanates. The Young's modulus increased with the isocyanate index, as could be expected. The ultimate tensile strength, elongation at break, toughness and heat resistance were dependant on the isocyanate index, whether initial polyurethane was linear or slightly crosslinked with TMP/1,4-BD (5/95 weight ratio) FIGS. 22–25).

Some morphology properties of the elastoplastics were measured by means of differential scanning calorimetry (DSC), dynamic-mechanical analysis (DMA) and thermomechanical analysis (TMA). The phase transition of the polyurethane elastoplastics at 170 to 185° C. as measured by the DSC is associated with the melting of the hard segment. DMA analysis indicated that the glass transition of the flexible segment of the PTMO elastoplastics was about −20° C., as measured by the maximum of E" (FIG. 40); thus the material is elastomeric at RT. The DMA of unfilled UHMW-PE exhibited a weak transition at −8° C. and a strong transition with a maximum at 67° C. (FIG. 41). The DSC analysis of UHMW-PE exhibited a sharp endothermic transition at 141° C., as measured by DSC (FIG. 32). TMA demonstrated the high expansion of the UHMWE-PE at about the same temperature and higher. The softening/ melting temperature of the polyurethane elastoplastics as measured by TMA was in the range of 150 to 230° C. (depending on the formulation). The coefficient of thermal expansion of UHMW-PE was 88.8 γm/m° C. (from RT to 45° C.) and for the polyurethane elastoplastics in the same temperature range 49.4–136 γm/m° C.

Properties of PPDI/MDI/HQEE/.Polycarbonate Diols

The formulations and properties of polyurethane elastoplastics based on polycarbonate diols are shown in Tables 20 & 21. These materials were prepared by reacting a NCO-prepolymer with an OH-prepolymer and HQEE chain extender. HQEE was compatible with Desmophen C-200 while phase separation was observed with 1,4-DB at the weight ratio of components required for 60–70% hard segment concentration. At similar hard segment concentration (58–60%), polycarbonate elastoplastics based on lower molecular weight diol exhibited higher tensile strength, Young's modulus and heat resistance. The compressive strength and modulus of these elastoplastics were excellent, especially for the slightly crosslinked type. The tear strength of crosslinked polycarbonate polyurethane was about 40% higher than that of thermoplastic PU and UHMW-PE. The shear strength of polycarbonate elastoplastics was similar to UHMW-PE and the values seems to correlate with flexural modulus.

Saline Resistance of Polyurethane Elastoplastics

Saline resistance of polyurethane elastoplastic, both PTMO and thermoplastic polycarbonate along with UHMW-PE was evaluated by measuring the weight change and retention of physico-mechanical properties (Tables 22 & 23; FIGS. 42–46). Polyurethane elastoplastics exhibited higher weight increase than did UHMW-PE, which is due to their polar nature; the weight did not increase after 10 days of. The weight increase of polycarbonate elastoplastics was nearly 50% less than that of PTMO. The hydrolytic resistance of polycarbonate polyurethanes was reported elsewhere. The retention of the physico-mechanical of polyurethanes, especially the polycarbonate type, was good, while UHMWE-PE exhibited a significant decrease of tensile strength and Young's modulus.

These, and further, correlations and properties can be determined from data reported on Tables 16–23, which follow, and from FIGS. 18–46, which are appended hereto (and par thereof).

TABLE 16

Properties of Polyurethane Elastoplastics Based on Prepolymer of PPDI and Mixtures of PTMO 650 + PTMO 1000

| Designation | 1 | 2 | 3 | 4 |
|---|---|---|---|---|
| Formulation of mixture of polyols (pbw) | | | | |
| Wt (PTMO 650, 50% by equivalent) | 100 | 100 | | |
| Wt (PTMO 1000, 50% by equivalent) | 147.39 | 147.39 | | |
| Wt (PTMO 650, 80% by equivalent) | | | 100 | 100 |
| Wt (PTMO 1000, 20% by equivalent) | | | 36.85 | 36.85 |
| Formulation of prepolymer (pbw) | | | | |
| Wt (PTMO 650 + PTMO 1000) | 100 | 100 | 100 | 100 |
| Wt (PPDI) | 39.72 | 39.72 | 44.88 | 44.88 |
| Formulation of mixture of extenders (pbw) | | | | |
| Wt (1,4-BD, 95% by equivalent) | | 100 | | 100 |
| Wt (TMP, 5% by equivalent) | | 5.28 | | 5.28 |
| Formulation of elastomer[a] (pbw) | | | | |
| Wt (Prepolymer) | 100 | 100 | 100 | 100 |
| Wt (MDI) | 70.90 | 70.89 | 65.11 | 65.11 |
| Wt (1,4-BD only) | 33.59 | | 32.09 | |
| Wt (1,4-BD + TMP) | | 33.59 | | 32.10 |
| T-12 based on the amount of polyol (%) | 0.002 | 0.002 | 0.002 | 0.002 |

TABLE 16-continued

Properties of Polyurethane Elastoplastics Based on Prepolymer of PPDI and Mixtures of PTMO 650 + PTMO 1000

| Designation | | 1 | 2 | 3 | 4 |
|---|---|---|---|---|---|
| Remelting conditions Properties | | | | | |
| Hardness (Shore D) | | 70 | 69 | 69 | 69 |
| Taber wear index[a] | | 11.0 | 10.8 | 7.3 | 7.3 |
| Ultimate tensile strength (psi) | RT | 7497 | 8345 | 7401 | 7755 |
| | 40° C. | 5291 | 7708 | 7671 | 8073 |
| Elongation at break (%) | RT | 540 | 458 | 520 | 562 |
| | 40° C. | 437 | 530 | 710 | 569 |
| Young's Modulus (psi) | RT | 31720 | 25770 | 39980 | 40580 |
| | 40° C. | 25400 | 29820 | 31650 | 37880 |
| Yield strength (psi) | RT | 3649 | 3818 | 1945 | 2506 |
| | 40° C. | 2198 | 2871 | 2238 | 3276 |
| Toughness (psi) | RT | 29343 | 25917 | 26628 | 33237 |
| | 40° C. | 19003 | 25432 | 35914 | 28203 |

[a]Isocyanate index = 102; Hard segment concentration = 65%
[b]The abrading wheels are H-22, the wheel loading = 500 g and the test cycles = 4000.

TABLE 17

Properties of Ultrahigh Molecular Polyethylene

| Designation | | 1 | |
|---|---|---|---|
| Samples | | Ultrahigh molecular weight polyethylene (Unfilled) | Ultrahigh molecular weight polyethylene (Filled) |
| Remelting conditions Properties | | 30 min. at 200° C. | 30 min. at 200° C. |
| Hardness (Shore D) | | 66 | 67 |
| Taber wear index[c] | | 3 | 1.5 |
| Ultimate tensile strength (psi) | RT | 8179 | 7740 |
| | 40° C. | 6622 | 6840 |
| Elongation at break (%) | RT | 460 | 409 |
| | 40° C. | 524 | 211 |
| Young's Modulus (psi) | RT | 23520 | 74610 |
| | 40° C. | 36350 | 54430 |
| Flexural Modulus (psi) | RT | | 53310 |
| Toughness (psi) | RT | 24200 | 18170 |
| | 40° C. | 20482 | 18933 |

TABLE 18

Properties of Polyurethane Elastoplastics Based on PPDI, MDI and PTMO Diols

| Designation | 1 | 2 | 3 | 4 |
|---|---|---|---|---|
| Samples | PU | PU | PU | UHMW-PE (Filled) |
| Formulation of polyols (pbw) | | | | |
| Wt (PTMO 650, 80% by equivalent) | | 100 | 100 | |
| Wt (PTMO 1000, 20% by equivalent) | | 36.85 | 36.85 | |
| Formulation of prepolymer (pbw) | | | | |
| Wt (PTMO 650) | 100 | | | |
| Wt (PTMO 650 + PTMO 1000) | | 100 | 100 | |
| Wt (PPDI) | 49.14 | 44.88 | 44.88 | |
| Formulation of extenders (pbw) | | | | |
| Wt (1,4-BD, 95% by equivalent) | | | 100 | |
| Wt (TMP, 5% by equivalent) | | | 5.28 | |
| Formulation of elastomer[a] (pbw) | | | | |
| Wt (Prepolymer) | 100 | 100 | 100 | |
| Wt (MDI) | 61.01 | 65.11 | 65.11 | |
| Wt (1,4-BD only) | 30.57 | 32.09 | | |
| Wt (1,4-BD + TMP) | | | 32.10 | |
| T-12 based on the amount of polyol (%) | 0 | 0.002 | 0.002 | |
| Remelting conditions Properties | | | | 30 min. at 200° C.) |
| Hardness (Shore D) | 68 | 69 | 69 | 67 |
| Taber wear index[b] | | 7.3 | 7.3 | 1.5 |
| Compression set at 40° C. (%) | | 14.5 | 10.2 | |
| Ultimate tensile strength (psi) RT | 9339 | 7401 | 7755 | 7740 |
| 40° C. | 8295 | 7671 | 8073 | 6840 |

TABLE 18-continued

Properties of Polyurethane Elastoplastics Based on PPDI, MDI and PTMO Diols

| Designation | | 1 | 2 | 3 | 4 |
|---|---|---|---|---|---|
| Elongation at break (%) | RT | 484 | 520 | 562 | 409 |
| | 40° C. | 482 | 710 | 569 | 211 |
| Young's modulus (psi) | RT | 48390 | 39980 | 40580 | 74610 |
| | 40° C. | 43510 | 31650 | 37880 | 53430 |
| Yield strength (psi) | RT | 4375 | 1945 | 2506 | 3147 |
| | 40° C. | 3399 | 2238 | 3276 | 1909 |
| Toughness (psi) | RT | 31642 | 26628 | 33237 | 18170 |
| | 40° C. | 27120 | 35914 | 28203 | 18933 |
| Flexural modulus (psi) | | 54680 | 77310 | 74630 | 53310 |
| Tear resistance (split) (lbs/in) | | | 1099 | 911 | 694 |
| Average shear strength (psi) | | | 601 | 608 | |
| Compressive strength (psi) | | | 3523 | 3943 | 3520 |
| Compressive modulus (psi) | | | 140700 | 168000 | 148100 |

[a]Isocyanate index = 102 and hard segment concentration = 65%.
[b]The abrading wheels are H-22, the wheel loading = 500 g and the test cycles = 4000.

TABLE 19

Effect of Isocyanate Index on the Properties of Polyurethane Elastoplastics Based on Prepolymer of PPDI and Mixture of 50% PTMO 650 + 50% PTMO 1000

| Designation | | 1 | 2 | 3 | 4 |
|---|---|---|---|---|---|
| Samples | | TMP = 0 | TMP = 0 | TMP = 5% | TMP = 5% |
| Isocyanate Index | | 102 | 105 | 102 | 105 |
| Formulation of mixture of polyols (pbw) | | | | | |
| Wt (PTMO 650, 50% by equivalent) | | 100 | 100 | 100 | 100 |
| Wt (PTMO 1000, 50% by equivalent) | | 147.39 | 147.39 | 147.39 | 147.39 |
| Formulation of prepolymer (pbw) | | | | | |
| Wt (PTMO 650 + PTMO 1000) | | 100 | 100 | 100 | 100 |
| Wt (PPDI) | | 39.72 | 39.72 | 39.72 | 39.72 |
| Formulation of mixture of extenders (pbw) | | | | | |
| Wt (1,4-BD, 95% by equivalent) | | | | 100 | 100 |
| Wt (TMP, 5% by equivalent) | | | | 5.28 | 5.28 |
| Formulation of elastomer (pbw) | | | | | |
| Wt (prepolymer) | | 100 | 100 | 100 | 100 |
| Wt (MDI) | | 70.90 | 71.61 | 70.89 | 71.61 |
| Wt (1,4-BD only) | | 33.59 | 32.87 | | |
| Wt (1,4-BD + TMP) | | | | 33.59 | 32.88 |
| T-12 based on the amount of polyol (%) | | 0.002 | 0.002 | 0.002 | 0.002 |
| Remelting conditions | | | | | |
| Properties | | | | | |
| Hardness (Shore D) | | 70 | 69 | 69 | 70 |
| Taber wear index[a] | | 11.0 | 13.3 | 10.8 | 6.8 |
| Ultimate tensile strength (psi) | RT | 7497 | 7689 | 8345 | 7351 |
| | 40° C. | 5291 | 7779 | 7708 | 7018 |
| Elongation at break (%) | RT | 540 | 534 | 485 | 375 |
| | 40° C. | 437 | 644 | 530 | 478 |

TABLE 19-continued

Effect of Isocyanate Index on the Properties of Polyurethane Elastoplastics Based on Prepolymer of PPDI and Mixture of 50% PTMO 650 + 50% PTMO 1000

| Designation | | 1 | 2 | 3 | 4 |
|---|---|---|---|---|---|
| Young's Modulus (psi) | RT | 31720 | 48880 | 25770 | 40510 |
| | 40° C. | 25400 | 33160 | 29820 | 30690 |
| Yield strength (psi) | RT | 3649 | 1865 | 3813 | 1886 |
| | 40° C. | 2198 | 2312 | 2871 | 2326 |
| Toughness (psi) | RT | 29343 | 19514 | 25917 | 17900 |
| | 40° C. | 19003 | 32521 | 25432 | 21125 |

[a] The abrading wheels are H-22, the wheel loading = 500 g and the test cycles = 4000.

TABLE 20

Properties of Polyurethane Elastoplastics Based on OH— and NCO— Terminated Prepolymer of PPDI and Desmophen C200

| Designation | | 1 | 2 |
|---|---|---|---|
| Formulation of OH-prepolymer (pbw) | | | |
| Wt (Desmophen C200) | | 100 | 100 |
| Wt (PPDI) | | 4.00 | 4.00 |
| Formulation of NCO-prepolymer (pbw) | | | |
| Wt (Desmophen C200) | | 100 | 100 |
| Wt (PPDI) | | 16.01 | 16.01 |
| Formulation of component-A (pbw) | | | |
| Wt (OH-prepolymer) | | 100 | 100 |
| Wt (HQEE) | | 112.09 | 112.09 |
| Benzol chloride based on the amount of polyol (%) | | 0.01 | 0.01 |
| Formulation of component-B (pbw) | | | |
| Wt (NCO-prepolyme) | | 100 | 100 |
| Wt (MDI) | | 172.66 | 172.66 |
| Formulation of elastomer[a] (pbw) | | | |
| Wt (component-A) | | 100 | 100 |
| Wt (component-B) | | 100 | 100 |
| Curing conditions | | 125° C. (1 hr) | 125° C. (1 hr) |
| Postcuring conditions | | 125° C. (16 hrs) | 135° C. (16 hrs) |
| Properties | | | |
| Hardness (Shore D) | | 70 | 70 |
| Taber wear index[a] | | 5.25 | 10.5 |
| Ultimate tensile strength (psi) | RT | 7251 | 6899 |
| | 40° C. | 5529 | 5360 |
| Elongation at break (%) | RT | 468 | 454 |
| | 40° C. | 378 | 416 |
| Young's Modulus (psi) | RT | 41080 | 53950 |
| | 40° C. | 23730 | 31660 |
| Yield strength (psi) | RT | 5257 | 3833 |
| | 40° C. | 1883 | 784 |
| Toughness (psi) | RT | 24534 | 25595 |
| | 40° C. | 17676 | 21851 |

[a] Hard segment concentration = 60% and Isocyanate index = 102.
[b] The abrading wheels are H-22, the wheel loading = 500 g and the test cycles = 4000.

TABLE 21

Properties of Polyurethane Elastoplastics Based on the OH— & NCO-Terminated Prepolymers of PPDI and PC1733[a]

| Designation | | 1 | 2 | 3 | |
|---|---|---|---|---|---|
| Samples | | PU | PU | UHMW-PE | |
| Formulation of OH-prepolymer (pbw) | | | | | |
| Wt (PC1733) | | 100 | 100 | | |
| Wt (PPDI) | | 9.07 | 9.07 | | |
| Formulation of NCO-prepolymer (pbw) | | | | | |
| Wt (PC1733) | | 100 | 100 | | |
| Wt (PPDI) | | 36.26 | 36.26 | | |
| Formulation of component-A (pbw) | | | | | |
| Wt (OH-prepolymer) | | 100 | 100 | | |
| Wt (HQEE) | | 81.83 | 77.76 | | |
| Wt (TMP) | | 0 | 1.83 | | |
| Wt (Irganox 565 based on amount elastomer) (%) | | 0.3 | 0.3 | | |
| Formulation of component-B (pbw) | | | | | |
| Wt (NCO-prepolymer, NCO = 6.84%) | | 100 | 100 | | |
| Wt (Free MDI) | | 123.16 | 122.77 | | |
| Formulation of elastomer (pbw) | | | | | |
| Wt (component-A) | | 100 | 100 | | |
| Wt (component-B) | | 99.40 | 99.40 | | |
| Remelting conditions | | | | 30 min. at 200° C. | |
| Properties | | | | Filled | Unfilled |
| Hardness at RT (Shore D) | | 71 | 74 | 67 | 66 |
| Taber wear index[b] | | 11.6 | 4.6 | 1.5 | |
| Ultimate tensile strength (psi) | RT | 7792 | 8437 | 7740 | 8179 |
| | 40° C. | 7771 | 7875 | 6840 | 6622 |
| Elongation at break (%) | RT | 448 | 398 | 409 | 460 |
| | 40° C. | 454 | 480 | 211 | 524 |

TABLE 21-continued

Properties of Polyurethane Elastoplastics Based on the OH— & NCO-Terminated Prepolymers of PPDI and PC1733[a]

| Designation | | 1 | 2 | 3 | |
|---|---|---|---|---|---|
| Young's modulus (psi) | RT | 51400 | 69260 | 74610 | 23520 |
| | 40° C. | 38470 | 45370 | 53430 | 36350 |
| Toughness (psi) | RT | 26357 | 20235 | 18170 | 24200 |
| | 40° C. | 22560 | | 18933 | 20480 |
| Flexural modulus (psi) | RT | 78850 | 80530 | 53310 | |
| | 40° C. | 55750 | 59650 | | |
| Tear Resistance (lbs/in) | RT | 695 | 1039 | 694 | |
| | 40° C. | 591 | 738 | | |
| Average shear strength (psi) | RT | 582 | 717 | 522 | 865 |
| | 40° C. | 665 | 544 | | |
| Compression set at 40° C. (%) | | 16.6 | 15.6 | | |
| Compressive strength at RT (psi) | | 4216 | 4215 | 3520 | |
| Compressive modulus at RT (psi) | | 184800 | 223500 | 148100 | |

[a]Isocyanate index = 102 and hard segment concentration = 58%.
[b]The abrading wheels are H-22, the wheel loading = 500 g and the test cycles = 4000.

TABLE 22

Effect of Saline Immersion at 40° C. on Properties of Polyurethane Elastoplastics Based on Prepolymer of PPDI and Mixtures of PTMO 650 + PTMO 1000

| Designation | | 1 | 2 | 3 | 4 | 5 |
|---|---|---|---|---|---|---|
| Samples | | PU | PU | PU | PU | UHMW-PE (Unfilled) |
| Formulation of polyols (pbw) | | | | | | |
| Wt (PTMO 650, 50% by equivalent) | | 100 | 100 | | | |
| Wt (PTMO 1000, 50% by equivalent) | | 147.39 | 147.39 | | | |
| Wt (PTMO 650, 80% by equivalent) | | | | 100 | 100 | |
| Wt (PTMO 1000, 20% by equivalent) | | | | 36.85 | 36.85 | |
| Formulation of prepolymer (pbw) | | | | | | |
| Wt (PTMO 650 + PTMO 1000) | | 100 | 100 | 100 | 100 | |
| Wt (PPDI) | | 39.72 | 39.72 | 44.88 | 44.88 | |
| Formulation of extenders (pbw) | | | | | | |
| Wt (1,4-BD, 95% by equivalent) | | | 100 | | 100 | |
| Wt (TMP, 5% by equivalent) | | | 5.28 | | 5.28 | |
| Formulation of elastomer[a] (pbw) | | | | | | |
| Wt (Prepolymer) | | 100 | 100 | 100 | 100 | |
| Wt (MDI) | | 70.90 | 70.89 | 65.11 | 65.11 | |
| Wt (1,4-BD only) | | 33.59 | | 32.09 | | |
| Wt (1,4-BD + TMP) | | | 33.59 | | 32.10 | |
| T-12 based on the amount of polyol (%) | | 0.002 | 0.002 | 0.002 | 0.002 | |
| Remelting conditions | | | | | | 30 min. at 200° C.) |
| Properties | | | | | | |
| Hardness (Shore D) | Before immersion | 70 | 69 | 69 | 69 | 66 |
| | After immersion | 70 | 65 | 70 | 70 | 65 |
| Taber wear index[b] | Before immersion | 11.0 | 10.8 | 7.3 | 7.3 | 3 |
| | After immersion | 24.3 | 28.4 | 25.2 | | 0.6 |
| Ultimate tensile strength (psi) | Before immersion | 7497 | 8345 | 7401 | 7755 | 8179 |
| | After immersion | 5384 | 8209 | 7988 | 7294 | 4499 |
| Elongation at break (%) | Before immersion | 540 | 458 | 520 | 562 | 460 |
| | After immersion | 358 | 496 | 631 | 451 | 481 |
| Young's Modulus (psi) | Before immersion | 31720 | 35770 | 39980 | 40580 | 23520 |
| | After immersion | 36250 | 24900 | 40930 | 28500 | 15740 |
| Yield strength (psi) | Before immersion | 3649 | 3818 | 1945 | 2506 | 3192 |
| | After immersion | 1670 | — | 2595 | 4162 | 4518 |
| Toughness (psi) | Before immersion | 29343 | 25917 | 26628 | 33237 | 24200 |
| | After immersion | 15966 | 23446 | 34848 | 25329 | 15069 |
| Average shear strength (psi) | Before immersion | 434 | 834 | 601 | 608 | 865 |
| | After immersion | 921 | 347 | 806 | 723 | 1199 |

[a]Isocyanate index = 102 and hard segment concentration = 65%
[b]The abrading wheels are H-22, the wheel loading = 500 g and the test cycles = 4000.

TABLE 23

Effect of Saline Immersion at 40° c. on Properties of Polyurethane Elastoplastics Based on the OH— & NCO-Terminated Prepolymers of PPDI and PC1733[a]

| Designation | 1 | 2 |
|---|---|---|
| Samples | PU | UHMW-PE (Unfilled) |
| Formulation of OH-prepolymer (pbw) | | |
| Wt (PC1733) | 100 | |
| Wt (PPDI) | 9.07 | |
| Formulation of NCO-prepolymer (pbw) | | |
| Wt (PC1733) | 100 | |
| Wt (PPDI) | 36.26 | |
| Formulation of component-A (pbw) | | |
| Wt (OH-prepolymer) | 100 | |
| Wt (HQEE) | 81.83 | |
| Wt (TMP) | 0 | |

TABLE 23-continued

Effect of Saline Immersion at 40° c. on Properties of Polyurethane Elastoplastics Based on the OH— & NCO-Terminated Prepolymers of PPDI and PC1733[a]

| Designation | | 1 | 2 |
|---|---|---|---|
| Wt (Irganox 565 based on amount elastomer) (%) | | 0.3 | |
| Formulation of compoent-B (pbw) | | | |
| Wt (NCO-prepolymer, NCO = 6.84%) | | 100 | |
| Wt (Free MDI) | | 123.16 | |
| Formulation of elastomer (pbw) | | | |
| Wt (component-A) | | 100 | |
| Wt (component-B) | | 99.40 | |
| Remelting conditions | | | 30 min. at 200° C. |
| Properties | | | |
| Hardness at RT (Shore D) | Before immersion | 71 | 66 |
| | After immersion | 66 | 65 |
| Taber wear index[b] | Before immersion | 11.6 | 3 |
| | After immersion | 13.3 | 0.6 |
| Ultimate tensile strength (psi) | Before immersion | 7792 | 8179 |
| | After immersion | 8125 | 4499 |
| Elongation at break (%) | Before immersion | 448 | 460 |
| | After immersion | 404 | 481 |
| Young's modulus (psi) | Before immersion | 51400 | 23520 |
| | After immersion | 62350 | 15740 |
| Yield strength (psi) | Before immersion | 1543 | — |
| | After immersion | 1498 | 4518 |
| Toughness (psi) | Before immersion | 26357 | 24200 |
| | After immesion | 22759 | 15069 |
| Flexural modulus (psI) | Before immersion | 78850 | — |
| | After immersion | 56120 | — |
| Tear Resistance (lbs/in) | Before immersion | 695 | — |
| | After immersion | 594 | — |
| Average shear strength (psi) | Before immersion | 582 | 865 |
| | After immersion | 597 | 1199 |
| Compression set at 40° C. (%) | Before immersion | 16.6 | — |
| | After immersion | 12.0 | — |

[a]Isocyanate index = 102 and hard segment concentration = 58%.
[b]The abrading wheels are H-22, the wheel loading = 500 g and the test cycles = 4000.

Thus, at least the two types of polyurethane elastoplastic materials, PPDI/MDI/PTMO650/PTMO1000 and PPDI/MDI/PC1000/HQEE, among others, exhibited very good combination of properties required for hip implant applications, as well as knee and other load-bearing joints.

EXAMPLE SET 4

From the foregoing monolithic, unreinforced (as by fiber) polyurethane elastomers of Example Sets 1–3, elastomeric plastic bars were prepared (FIG. 1). Machining trials demonstrated good machining property behavior of the polyurethane elastoplastics.

In particular, a set of demonstration knee tibial tray liners were machined by known methods (FIG. 47). Nothing out of the ordinary was encountered in the machining, and these knee joint component demonstration models performed in evaluations with satisfaction.

CONCLUSION

The present invention is thus provided. Numerous and sundry adaptations and modifications can be effected in the spirit of the invention, with various features, subcombinations and combinations able to be practiced with or without reference to other features, subcombinations or combinations, the literal claim scope of which is particularly pointed out as follows:

We claim:

1. An article of manufacture comprising a polyurethane-containing, load-bearing prosthetic joint implant or component therefor, suitable for use in total joint replacement arthroplasty, said joint implant or component being monolithic with respect to polyurethane-containing component(s); and having requisite structural integrity for long-term load-bearing joint implant application; wherein said joint is structurally an articulated joint, and the polyurethane component provides a surface for articulation with the polyurethane.

2. The article of claim 1, wherein the polyurethane contains at least one of an aliphatic, cycloaliphatic and aromatic polyol residue.

3. The article of claim 1, which includes said polyurethane component and another hard, structural component for articulation with said polyurethane component in a total replacement joint implant.

4. An article of manufacture comprising a component for a load-bearing prosthetic joint implant, being a material selected from at least one of a polyurethaneurea, polyurea and polyisocyanurate, and analog(s) thereof, wherein said joint is structurally an articulated joint, and said component provides a surface for articulation with said material.

5. The article of claim 4, wherein said analog is a halogenated composition.

6. The article of claim 4, wherein said analog is a thio composition.

7. The article of claim 4, wherein said surface is concave.

8. The article of claim 7, which is selected from the group consisting of a tibial tray liner, and an acetabular cup.

9. The article of claim 4, further comprising said prosthetic joint.

10. An article of manufacture comprising a component for a load-bearing prosthetic joint implant, the component being at least one of a polyurethane-containing material and an analog thereof, suitable to use in total joint replacement arthroplasty, being monolithic with respect to itself, and having requisite structural integrity for long-term load-=bearing joint implant application, wherein said joint is structurally an articulated joint, and the component provides a surface for articulation.

11. The article of claim 10, which embraces a reaction product of at least one of an aliphatic, cycloaliphatic and aromatic isocyanate, and a polyol, with said reaction product being at least one of elastomeric and elastoplastic in nature.

12. The article of claim 11, wherein
said isocyanate embraces an isocyanate selected from at least one of the group consisting of 2,4-methylene diisocyanate; 4,4-methylene diisocyanate; a mixture of 2,2-, 2,4- and 4,4-methylene diisocyanate; 1,6-hexamethylene diisocyanate; 4,4'-methylene bis(cyclohexyl isocyanate); isophorene diisocyanate; 1,4-cyclohexyl diisocyanate; 2,4-toluene diisocyanate; mixture of 2,4- and 2,6-toluene diisocyanate; 4,4'-methylene bis(phenyl isocyanate); a mixture of 4,4'- and 2,4'-methylene bis(phenyl isocyanate); a mixtures of 4,4'-, 2,4'- and 2,2'-methylene bis(phenyl isocyanate); para-phenylene diisocyanate; 1,5-naphthalene diisocyanate; poly(methylene)poly(phenylene) polyisocyanate; carbodiimide-modified methylene diisocyanate; a quasi-prepolymer containing a methylene diisocyanate; a polymeric methylene diisocyanate with NCO-functionality about from 2.1–3.0; an adduct of an isocyanate to a polyol; a trimerization product of an isocyanate; and a biuret adduct of 1,6-methylene diisocyanate (with R being C(=O)—O(CH2)6—NCO):

OCN—(CH2)6—NCO+H2O→RHN—C(=O)—NR—C(=O)—NHR; and said polyol embraces a polyol selected from at least one of the group consisting of a polyether; a polyester; a polyadipate; a polysuccinate; a product of a glycol with a dibasic acid; a polycaprolactone; a polycarbonate, which is not a poly(carbonate) diol; a poly(carbonate) diol; an acrylic-based glycol; an acrylate-based polyol; an epoxy-based glycol; an epoxy-based polyol; a poly(oxyalkylene) glycol; a poly(oxyalkylene) polyol; glycerol; trimethylolpropane; penteretythritol; sorbitol; sucrose; an adduct of propylene oxide; and an adduct of propylene oxide and ethylene oxide.

13. The article of claim 11, wherein a chain extender is present.

14. The article of claim 12, wherein a chain extender is present.

15. The article of claim 10, wherein said analog is a halogenated composition.

16. The article of claim 10, wherein said analog is a thio composition.

17. The article of claim 10, wherein said surface is concave so as to receive a convex part.

18. The article of claim 11, which is selected from the group consisting of a tibial tray liner, and an acetabular cup.

19. The article of claim 15, further comprising said prosthetic joint.

20. The article of claim 11, wherein a mixture of hard segments and flexible segments are employed to make said component, and said component is slightly crosslinked.

* * * * *

UNITED STATES PATENT AND TRADEMARK OFFICE
CERTIFICATE OF CORRECTION

PATENT NO. : 6,302,916 B1 Page 1 of 1
DATED : October 16, 2001
INVENTOR(S) : Townley et al.

It is certified that error appears in the above-identified patent and that said Letters Patent is hereby corrected as shown below:

Column 6,
Lines 59-61, replace that paragraph with the following paragraph:

-- FIG. 47 presents views of some joint components of the invention, containing (acetabular cup, FIG. 47A) or being (tibial tray liner, FIG. 47B) a monolithic load-bearing joint implant component. --.

Column 30,
Lines 41-44, replace that paragraph with the following paragraph:
-- Such samples may be utilized to machine artificial joints such as depicted within FIG. 47. In particular, acetabular cups (FIG. 47A) and tibial tray liners (FIG. 47B), for example, may be machined therefrom and further tested. --.

Signed and Sealed this

Third Day of December, 2002

JAMES E. ROGAN
*Director of the United States Patent and Trademark Office*